US009663814B2

(12) United States Patent
Farrell et al.

(10) Patent No.: US 9,663,814 B2
(45) Date of Patent: May 30, 2017

(54) PROXIMITY ASSAY FOR IN SITU DETECTION OF TARGETS

(71) Applicant: Ventana Medical Systems, Inc., Tucson, AZ (US)

(72) Inventors: Michael Farrell, Tucson, AZ (US); Rui Hong, Oro Valley, AZ (US); Zeyu Jiang, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 0 days.

(21) Appl. No.: 14/769,892

(22) PCT Filed: Mar. 11, 2014

(86) PCT No.: PCT/EP2014/054634
§ 371 (c)(1),
(2) Date: Aug. 24, 2015

(87) PCT Pub. No.: WO2014/139980
PCT Pub. Date: Sep. 18, 2014

(65) Prior Publication Data
US 2016/0002701 A1    Jan. 7, 2016

Related U.S. Application Data

(60) Provisional application No. 61/777,738, filed on Mar. 12, 2013.

(51) Int. Cl.
*C12Q 1/25* (2006.01)
*G01N 33/535* (2006.01)
*G01N 33/58* (2006.01)

(52) U.S. Cl.
CPC ............. *C12Q 1/25* (2013.01); *G01N 33/535* (2013.01); *G01N 33/581* (2013.01); *G01N 2333/9015* (2013.01); *G01N 2440/32* (2013.01)

(58) Field of Classification Search
None
See application file for complete search history.

(56) References Cited

U.S. PATENT DOCUMENTS

| 4,711,955 A | 12/1987 | Ward et al. |
| 5,306,518 A | 4/1994 | Chablaix et al. |
| (Continued) | | |

FOREIGN PATENT DOCUMENTS

WO    2012003476 A2    1/2012

OTHER PUBLICATIONS

Altschul, S.F., et al., "Basic Local Alignment Search Tool," J. Mol. Biol., (1990) 215, pp. 403-410.

(Continued)

*Primary Examiner* — Jacob Cheu
(74) *Attorney, Agent, or Firm* — Ventana Medical Systems, Inc.

(57) ABSTRACT

A proximity detection method is described that utilizes enzymatic biotinylation to detect targets in a sample, particularly formalin fixed paraffin embedded samples using automated staining platforms. One disclosed embodiment comprises contacting the sample with a first conjugate comprising a biotin ligase and a first specific binding moiety that binds proximally to the first target; contacting the sample with a second conjugate comprising a biotin ligase substrate and a second specific binding moiety that binds proximally to the second target; subjecting the sample to conditions that allow biotinylation of the biotin ligase substrate by the biotin ligase when the first target and the second target have a proximal arrangement; and detecting biotinylation of the biotin ligase substrate. The conditions that allow biotinylation of the substrate include addition of biotin (Continued)

and ATP. The method also may comprise contacting the sample with a streptavidin-enzyme conjugate. Signal amplification also can be used.

21 Claims, 10 Drawing Sheets

(56) References Cited

U.S. PATENT DOCUMENTS

| | | |
|---|---|---|
| 5,661,028 A | 8/1997 | Foote |
| 5,707,804 A | 1/1998 | Mathies et al. |
| 5,733,523 A | 3/1998 | Kuijpers et al. |
| 5,734,018 A | 3/1998 | Rutter et al. |
| 5,741,713 A | 4/1998 | Brown et al. |
| 5,851,829 A | 12/1998 | Marasco et al. |
| 5,965,371 A | 10/1999 | Marasco et al. |
| 6,921,496 B2 | 7/2005 | Anderson et al. |
| 7,410,753 B2 | 8/2008 | Hopkins et al. |
| 7,615,371 B2 | 11/2009 | Kram |
| 7,695,929 B2 | 4/2010 | Kosmeder et al. |
| 2006/0246524 A1 | 11/2006 | Bauer et al. |
| 2009/0176253 A1 | 7/2009 | Bieniarz et al. |
| 2010/0136652 A1 | 6/2010 | Bieniarz et al. |
| 2013/0260379 A1 | 10/2013 | Alexander et al. |

OTHER PUBLICATIONS

Arribas, J. et al., "p95HER2 and Breast Cancer," Cancer Research, 71(5) Mar. 1, 2011, pp. 1515-1519 (published online first Feb. 22, 2011).
Mayer, G. and Bendayan M., "Immunogold Signal Amplification: Application of the CARD Approach to Electron Microscopy," The Journal of Histochemistry & Cytology, vol. 47(4): pp. 421-420, 1999.
Bobrow, M.N., et al., "Catalyzed reporter deposition, a novel method of signal amplification," Journal of Immunological Methods, 125 (1989), pp. 279-285.
Herbst, R.S., "Review of epidermal growth factor receptor biology," Int. J. Radiation Oncology Biol. Phys., vol. 59, No. 2, Supplement, pp. 21-26, 2004.
Molina, M.A., et al., "Trastuzumab (Herceptin), a Humanized Anti-HER2 Receptor Monoclonal Antibody, Inhibits Basal and Activated HER2 Ectodomain Cleavage in Breast Cancer Cells," Cancer Research, 61, Jun. 15, 2001, pp. 4744-4749.
Santin, A.D., et al., "Trastuzumab treatment in patients with advanced or recurrent endometrial carcinoma overexpressing HER2/neu," International Journal of Gynecology and Obstetrics (2008) 102, pp. 128-131.
Shen, Z., et al., "Engineered Recombinant Single-Chain Fragment Variable Antibody for Immunosensors," Anal. Chem. 2005, 77, pp. 6834-6842.
Zahnd, C., et al., "A Designed Ankyrin Repeat Protein Evolved to Picomolar Affinity to Her2," J. Mol. Biol., (2007) 369, pp. 1015-1028.
Zhang, H., et al., "ErbB receptors: from oncogenes to targeted cancer therapies," The Journal of Clinical Investigation, vol. 117, No. 8, Aug. 2007, pp. 2051-2058.
Hinner, M.J., and Johnsson K., "How to obtain labeled proteins and what to do with them," Current Opinion in Biotechnology 2010, 21, pp. 766-776.
Lowder, M.A., et al., "Visualizing protein partnerships in living cells and organisms," Current Opinion in Chemical Biology, 2011, 15, pp. 781-788.
Roux, K.J., et al., "A promiscuous biotin ligase fusion protein identifies proximal and interacting proteins in mammalian cells," J.Cell Biol., vol. 196, No. 6, pp. 801-810 (2012).
Kulyyassov, A., et al., "PUB-MS: A Mass Spectrometry-based Method to Monitor Protein—Protein Proximity in vivo," Journal of Proteome Research, 2011, 10, pp. 4416-4427.

Fernandez-Suarez, M., et al., "Protein-Protein Interaction Detection in Vitro and In Cells by Proximity Biotinylation," J. Am. Chem. Soc., 2008, 130, pp. 9251-9253.
Conrad, R.C., et al., "In Vitro Selection of Nucleic Acid Aptamers That Bind Proteins," Methods in Enzymology, vol. 267, (1996) pp. 336-367.
Amin, D.N., et al., "The role of HER3, the unpretentious member of the HER family, in cancer biology and cancer therapeutics," Seminars in Cell & Developmental Biology, 21 (2010), pp. 944-950.
Choi, B-K., et al., "ERBB3 (HER3) is a key sensor in the regulation of ERBB-mediated signaling in both low and high ERBB2 (HER2) expressing cancer cells," Cancer Medicine 2013, 1(1), pp. 28-38.
Ishiyama, N., et al., Dynamic and Static Interactions between p120 Catertin and E-Cadherin Regulate the Stability of Cell-Cell Adhension, Cell 141, Apr. 2, 2010, pp. 117-128.
Lamers, M.H., et al., "The crystal structure of DNA mismatch repair protein MutS binding to a G-T mismatch," Nature., vol. 407, Oct. 12, 2000, pp. 711-717.
Wood, Z.A., et al., "Co-repressor Induced Order and Biotin Repressor Dimerization: A Case for Divergent Followed by Convergent Evolution," J. Mol. Biol. (2006), 357, pp. 509-523.
KEEG entry http://www.genome.jp/dbget-bin/www_bget?ec:6.3.4. 15 retrieved on Aug. 11, 2015, 1 pp.
Fischer, D.S., Knobf, M.F., Duhvage, H.J. (eds): The Cancer Chemotherapy Handbook, 4th ed. St. Louis, Mosby—Year Book, 1993, Cover, Edition Notice and Table of Contents, 5 pages.
Bonadonna et al., (eds), Texbook of Breast Cancer: A clinical Guide the Therapy, 3rd; London, Taylor & Francis, 2006, Cover, Edition Notice and Table of Contents: 3 pages.
Harlow & Lane, Antibodies, A Laboratory Manual, Cold Spring Harbor Publications, New York (1988), Cover, Edition Notice and Table of Contents, 9 pages.
Slapak and Kufe, Principles of Cancer Therapy, Chapter 86 in Harrison's Principles of Internal Medicine, 14th edition, 1998, Cover, Edition Notice, Table of Contents, and Chapter 86, 27 pages.
Sambrook et al., Molecular Cloning: A Laboratory Manual, Cold Spring Harbor Laboratory Press (1989), Cover, Edition Notice, Table of Contents, 30 pages.
Robert A. Meyers (ed.), Molecular Biology and Biotechnology: a Comprehensive Desk Reference, published by VCH Publishers, Inc., 1995 (ISBN 1-56081-569-8), Cover, Edition Notice, and Table of Contents, 9 pages.
Benjamin Lewin, Genes V, published by Oxford University Press, 1994 (ISBN 0-19-854287-9), Cover, Edition Notice, and Table of Contents, 20 pages.
Kendrew et al. (eds.), The Encyclopedia of Molecular Biology, published by Blackwell Science Ltd., 1994 (ISBN 0-632-02182-9), Cover, Edition Notice, and Table of Contents, 6 pages.
Hermanson, "Bioconjugate Techniques," Academic Press, San Diego, 1996, Cover, Edition Notice, and Table of Contents, 15 pages.
Chabner and Longo, Cancer Chemotherapy and Biotherapy: Principles and Practice (4th ed.), Philadelphia: Lippincott Williams & Wilkins, 2005, Cover, Edition Notice, and Table of Contents, 4 pages.
Ausubel et al., Current Protocols in Molecular Biology, Greene Publishing Associates and Wiley—Intersciences (1987), Cover, Edition Notice, and Table of Contents, 8 pages.
Sambrook et al.; and Tijssen, Hybridization With Nucleic Acid Probes, Part I: Theory and Nucleic Acid Preparation, Laboratory Techniques in Biochemistry and Molecular Biology, Elsevier Science Ltd., 1993, Cover, Edition Notice, and Table of Contents, 7 pages.
Baltzer, L., Berkery, R. (eds): Oncology Pocket Guide to Chemotherapy, 2nd ed. St. Louis, Mosby—Year Book, 1995, Cover, Edition Notice, Table of Contents, 8 pages.
Soderberg, O. et al., "Direct observation of individual endogenous protein complexes in situ by proximity ligation," Nature Methods, vol. 3, No. 12, Dec. 2006, published online Oct. 29, 2008, pp. 995-1000.

(56) References Cited

OTHER PUBLICATIONS

Application Notes—Olink Bioscience, "Analyzing human epidermal growth factor receptor family dimerization and activation using Duolink," Nature Methods, Dec. 2010, 2 pages.
Perry, M.C et al., Chemotherapy, Ch. 17 in Abeloff, Clinical Oncology 2nd ed., 2000 Churchill Livingstone, Inc., Cover, Edition Notice, Table of Contents, Chapter 17, 48 pages.

SEQUENCE LISTING

```
<160> NUMBER OF SEQ ID NOS: 16

<210> SEQ ID NO 1
<211> LENGTH: 97
<212> TYPE: DNA
<213> ORGANISM: Escherichia coli
```

<400> SEQUENCE: 1

```
catatgggaa gcggccatca ccaccaccat cacggaggcg gaggttcagg ctgcagcaac    60
ctgtctacct gtgtgttgaa ggataacacc gtgccac                             97
```

<210> SEQ ID NO 2
<211> LENGTH: 35
<212> TYPE: DNA
<213> ORGANISM: Escherichia coli

<400> SEQUENCE: 2

```
gctgtcgact tattttctg cactacgcag ggata                                35
```

<210> SEQ ID NO 3
<211> LENGTH: 345
<212> TYPE: PRT
<213> ORGANISM: Artificial Sequence
<220> FEATURE:
<223> OTHER INFORMATION: fusion protein

<400> SEQUENCE: 3

```
Met Gly Ser Gly His His His His His Gly Gly Gly Ser Gly
1               5                   10                  15

Cys Ser Asn Leu Ser Thr Cys Val Leu Lys Asp Asn Thr Val Pro Leu
            20                  25                  30

Lys Leu Ile Ala Leu Leu Ala Asn Gly Glu Phe His Ser Gly Glu Gln
        35                  40                  45

Leu Gly Glu Thr Leu Gly Met Ser Arg Ala Ala Ile Asn Lys His Ile
    50                  55                  60

Gln Thr Leu Arg Asp Trp Gly Val Asp Val Phe Thr Val Pro Gly Lys
65                  70                  75                  80

Gly Tyr Ser Leu Pro Glu Pro Ile Gln Leu Leu Asn Ala Lys Gln Ile
                85                  90                  95

Leu Gly Gln Leu Asp Gly Gly Ser Val Ala Val Leu Pro Val Ile Asp
            100                 105                 110

Ser Thr Asn Gln Tyr Leu Leu Asp Arg Ile Gly Glu Leu Lys Ser Gly
        115                 120                 125

Asp Ala Cys Ile Ala Glu Tyr Gln Gln Ala Gly Arg Gly Arg Arg Gly
    130                 135                 140

Arg Lys Trp Phe Ser Pro Phe Gly Ala Asn Leu Tyr Leu Ser Met Phe
145                 150                 155                 160

Trp Arg Leu Glu Gln Gly Pro Ala Ala Ala Ile Gly Leu Ser Leu Val
                165                 170                 175

Ile Gly Ile Val Met Ala Glu Val Leu Arg Lys Leu Gly Ala Asp Lys
            180                 185                 190

Val Arg Val Lys Trp Pro Asn Asp Leu Tyr Leu Gln Asp Arg Lys Leu
        195                 200                 205

Ala Gly Ile Leu Val Glu Leu Thr Gly Lys Thr Gly Asp Ala Ala Gln
    210                 215                 220

Ile Val Ile Gly Ala Gly Ile Asn Met Ala Met Arg Arg Val Glu Glu
225                 230                 235                 240

Ser Val Val Asn Gln Gly Trp Ile Thr Leu Gln Glu Ala Gly Ile Asn
                245                 250                 255

Leu Asp Arg Asn Thr Leu Ala Ala Met Leu Ile Arg Glu Leu Arg Ala
            260                 265                 270

Ala Leu Glu Leu Phe Glu Gln Glu Gly Leu Ala Pro Tyr Leu Ser Arg
        275                 280                 285
```

Trp Glu Lys Leu Asp Asn Phe Ile Asn Arg Pro Val Lys Leu Ile Ile
            290                 295                 300

Gly Asp Lys Glu Ile Phe Gly Ile Ser Arg Gly Ile Asp Lys Gln Gly
305                 310                 315                 320

Ala Leu Leu Glu Gln Asp Gly Ile Ile Lys Pro Trp Met Gly Gly
                325                 330                 335

Glu Ile Ser Leu Arg Ser Ala Glu Lys
            340                 345

<210> SEQ ID NO 4
<211> LENGTH: 232
<212> TYPE: PRT
<213> ORGANISM: Artificial Sequence
<220> FEATURE:
<223> OTHER INFORMATION: Thermococcus kodakarensis KOD1

<400> SEQUENCE: 4

Met Glu Trp Asn Val Ile Arg Leu Asp Glu Val Asp Ser Thr Asn Glu
1               5                   10                  15

Tyr Ala Lys Lys Leu Ile Pro Asp Val Ser Glu Gly Thr Val Val Val
            20                  25                  30

Ala Lys Arg Gln Thr Ser Gly Arg Gly Arg Lys Gly Arg Ala Trp Ala
        35                  40                  45

Ser Pro Glu Gly Gly Leu Trp Met Ser Val Ile Leu Lys Pro Pro Met
    50                  55                  60

Ile Asp Pro Arg Leu Val Phe Val Gly Ala Leu Ala Val Ser Asp Thr
65                  70                  75                  80

Leu Arg Asp Phe Gly Ile Gly Ala Trp Ile Lys Trp Pro Asn Asp Val
                85                  90                  95

Trp Val Gly Asn Arg Lys Ile Ser Gly Val Leu Thr Glu Val Lys Gly
            100                 105                 110

Asp Phe Val Ile Met Gly Val Gly Leu Asn Val Asn Asn Glu Ile Pro
        115                 120                 125

Asp Gly Leu Lys Glu Thr Ala Thr Ser Met Met Glu Ala Leu Gly Glu
    130                 135                 140

Pro Val Asp Ile Gly Glu Val Leu Glu Arg Leu Leu Glu Tyr Leu Gly
145                 150                 155                 160

Arg Trp Tyr Lys Thr Phe Leu Glu Asn Pro Pro Leu Val Glu Glu
                165                 170                 175

Val Arg Gly Arg Thr Met Leu Ile Gly Lys Glu Val Arg Val Leu Leu
            180                 185                 190

Asp Gly Asn Asp Leu Val Gly Arg Val Ile Thr Ile Ser Asp Asp Gly
        195                 200                 205

Ser Leu Ile Leu Asp Val Asp Gly Gln Thr Val Lys Val Val Tyr Gly
    210                 215                 220

Asp Val Ser Val Arg Ile Asn Arg
225                 230

<210> SEQ ID NO 5
<211> LENGTH: 231
<212> TYPE: PRT
<213> ORGANISM: Thermococcus sp. AN1

<400> SEQUENCE: 5

Met Trp Lys Ile Ile His Leu Asp Glu Val Asp Ser Thr Asn Asp Tyr
1               5                   10                  15

Ala Lys Ser Ile Ala Glu Glu Ser Pro Glu Gly Thr Val Val Ile Ala
            20                  25                  30

Lys Arg Gln Thr Ala Gly Lys Gly Arg Lys Gly Arg Ser Trp Ala Ser
        35                  40                  45

Pro Glu Gly Gly Leu Trp Met Ser Val Ile Leu Lys Pro Glu Arg Thr
    50                  55                  60

Asp Pro Arg Leu Val Phe Val Gly Ala Leu Ala Val Val Asp Thr Leu
65                  70                  75                  80

Ala Asp Phe Gly Ile Lys Gly Trp Ile Lys Trp Pro Asn Asp Val Trp
                85                  90                  95

Val Glu Gly Lys Lys Ile Ala Gly Val Leu Thr Glu Gly Lys Ala Glu
            100                 105                 110

Lys Phe Val Val Met Gly Ile Gly Leu Asn Val Asn Asn Pro Val Pro
        115                 120                 125

Glu Gly Leu Glu Arg Glu Ala Thr Ser Met Ile Tyr His Thr Gly Met
    130                 135                 140

Glu Leu Pro Leu Asp Ser Val Leu Asp Arg Leu Leu Phe His Leu Gly
145                 150                 155                 160

Gly Trp Tyr Gly Val Tyr Lys Glu Arg Pro Glu Leu Leu Val Glu Lys
                165                 170                 175

Leu Arg Gln Arg Thr Phe Ile Leu Gly Lys Ala Val Arg Val Thr Glu
            180                 185                 190

Asp Asp Lys Thr Ile Ile Gly Arg Ala Leu Asp Val Leu Asp Asp Gly
        195                 200                 205

Ser Leu Leu Leu Glu Val Gly Gly Glu Leu Arg Arg Ile Leu Tyr Gly
    210                 215                 220

Asp Val Ser Val Arg Pro Leu
225                 230

<210> SEQ ID NO 6
<211> LENGTH: 237
<212> TYPE: PRT
<213> ORGANISM: Artificial Sequence
<220> FEATURE:
<223> OTHER INFORMATION: Thermococcus gammatolerans EJ3

<400> SEQUENCE: 6

Met Glu Trp Asn Ile Ile Thr Leu Asp Glu Val Asp Ser Thr Asn Glu
1               5                   10                  15

Tyr Ala Arg Arg Ile Ala Pro Thr Ala Pro Glu Gly Thr Val Val Val
            20                  25                  30

Ala Lys Arg Gln Thr Ala Gly Arg Gly Arg Lys Gly Arg Trp Ala
        35                  40                  45

Ser Pro Glu Gly Gly Leu Trp Met Thr Val Ile Leu Lys Pro Lys Ser
    50                  55                  60

Gly Pro Glu His Val Thr Lys Leu Val Phe Val Gly Ala Leu Ala Val
65                  70                  75                  80

Leu Asp Thr Leu His Glu Tyr Gly Ile Arg Gly Glu Leu Lys Trp Pro
                85                  90                  95

Asn Asp Val Leu Val Asp Gly Lys Lys Ile Ala Gly Ile Leu Ser Glu
            100                 105                 110

Cys Arg Leu Asn His Phe Ala Leu Leu Gly Ile Gly Leu Asn Val Asn
        115                 120                 125

Asn Glu Ile Pro Asp Glu Leu Arg Glu Ser Ala Val Ser Met Lys Glu
    130                 135                 140

```
Val Leu Gly Arg Ala Ile Asp Leu Glu Glu Val Leu Asn Arg Val Leu
145                 150                 155                 160

Arg Asn Leu Ser Arg Trp Tyr Gly Leu Phe Arg Asn Gly Arg His Gly
                165                 170                 175

Glu Ile Leu Lys Ala Val Lys Gly Ser Ser Ala Val Leu Gly Lys Arg
                180                 185                 190

Val Arg Ile Ile Glu Asp Gly Glu Ile Ile Ala Glu Gly Ile Ala Val
                195                 200                 205

Asp Ile Asp Asn Ser Gly Ala Leu Ile Leu Lys Gly Glu Glu Asn Thr
210                 215                 220

Val Arg Val Leu Tyr Gly Asp Val Ser Leu Arg Phe Ser
225                 230                 235

<210> SEQ ID NO 7
<211> LENGTH: 237
<212> TYPE: PRT
<213> ORGANISM: Pyrococcus abyssi

<400> SEQUENCE: 7

Met Leu Gly Leu Lys Thr Ser Val Ile Gly Arg Thr Ile Ile Tyr Phe
1               5                   10                  15

Gln Glu Val Ala Ser Thr Asn Asp Tyr Ala Lys Ala Glu Asn Leu Glu
                20                  25                  30

Glu Gly Thr Val Ile Val Ala Asp Arg Gln Ile Lys Gly His Gly Arg
            35                  40                  45

Leu Glu Arg Lys Trp Glu Ser Pro Glu Gly Gly Leu Trp Met Ser Val
    50                  55                  60

Val Leu Thr Pro Arg Val Ser Gln Glu Asp Leu Pro Lys Ile Val Phe
65                  70                  75                  80

Leu Gly Ala Leu Ala Val Val Glu Thr Leu Arg Glu Phe Ser Ile Asp
                85                  90                  95

Ala Arg Ile Lys Trp Pro Asn Asp Val Leu Val Asn Tyr Arg Lys Val
                100                 105                 110

Ala Gly Val Leu Val Glu Ala Lys Gly Glu Lys Val Ile Leu Gly Ile
            115                 120                 125

Gly Leu Asn Val Asn Asn Lys Val Pro Asp Gly Ala Thr Ser Met Lys
    130                 135                 140

Gln Glu Leu Gly Ser Glu Ile Pro Met Leu Asn Val Phe Lys Thr Leu
145                 150                 155                 160

Val Lys Thr Leu Asp Ser Leu Tyr Leu Lys Phe Leu Glu Ser Pro Gly
                165                 170                 175

Lys Ile Leu Glu Arg Ala Lys Arg Ser Met Ile Leu Gly Val Arg Val
                180                 185                 190

Lys Val Leu Ser Asp Gly Glu Val Glu Ala Glu Gly Ile Ala Glu Asp
            195                 200                 205

Val Asp Glu Phe Gly Arg Leu Ile Val Arg Leu Asp Asp Gly Arg Val
    210                 215                 220

Lys Lys Ile Leu Tyr Gly Asp Val Ser Leu Arg Phe Leu
225                 230                 235

<210> SEQ ID NO 8
<211> LENGTH: 235
<212> TYPE: PRT
<213> ORGANISM: Pyrococcus horikoshii

<400> SEQUENCE: 8
```

```
Met Leu Gly Leu Lys Thr Ser Ile Ile Gly Arg Arg Val Ile Tyr Phe
1               5                   10                  15

Gln Glu Ile Thr Ser Thr Asn Glu Phe Ala Lys Thr Ser Tyr Leu Glu
                20                  25                  30

Glu Gly Thr Val Ile Val Ala Asp Lys Gln Thr Met Gly His Gly Arg
            35                  40                  45

Leu Asn Arg Lys Trp Glu Ser Pro Glu Gly Gly Leu Trp Leu Ser Ile
50                  55                  60

Val Leu Ser Pro Lys Val Pro Gln Lys Asp Leu Pro Lys Ile Val Phe
65                  70                  75                  80

Leu Gly Ala Val Gly Val Val Glu Thr Leu Lys Glu Phe Ser Ile Asp
                85                  90                  95

Gly Arg Ile Lys Trp Pro Asn Asp Val Leu Val Asn Tyr Lys Lys Ile
            100                 105                 110

Ala Gly Val Leu Val Glu Gly Lys Gly Asp Lys Ile Val Leu Gly Ile
            115                 120                 125

Gly Leu Asn Val Asn Asn Lys Val Pro Asn Gly Ala Thr Ser Met Lys
130                 135                 140

Leu Glu Leu Gly Ser Glu Val Pro Leu Leu Ser Val Phe Arg Ser Leu
145                 150                 155                 160

Ile Thr Asn Leu Asp Arg Leu Tyr Leu Asn Phe Leu Lys Asn Pro Met
                165                 170                 175

Asp Ile Leu Asn Leu Val Arg Asp Asn Met Ile Leu Gly Val Arg Val
                180                 185                 190

Lys Ile Leu Gly Asp Gly Ser Phe Glu Gly Ile Ala Glu Asp Ile Asp
            195                 200                 205

Asp Phe Gly Arg Leu Ile Ile Arg Leu Asp Ser Gly Glu Val Lys Lys
            210                 215                 220

Val Ile Tyr Gly Asp Val Ser Leu Arg Phe Leu
225                 230                 235

<210> SEQ ID NO 9
<211> LENGTH: 328
<212> TYPE: PRT
<213> ORGANISM: Clostridium botulinum

<400> SEQUENCE: 9

Met Lys Glu Glu Ile Ile Ser Leu Leu Lys Glu Asn Lys Asp Asn Phe
1               5                   10                  15

Ile Ser Gly Glu Lys Ile Ser Glu Lys Phe Gly Ile Thr Arg Ala Ala
                20                  25                  30

Ile Trp Lys Tyr Met Lys Ala Ile Lys Asn Glu Gly Tyr Lys Ile Glu
            35                  40                  45

Ser Val Ser Arg Lys Gly Tyr Lys Leu Ile Ser Ser Pro Asp Leu Leu
50                  55                  60

Thr Phe Gln Glu Ile Asn Pro Tyr Leu Thr Thr Asn Tyr Ile Gly Lys
65                  70                  75                  80

Asn Ile Met Tyr Phe Asn Thr Ile Asp Ser Thr Asn Lys Ala Lys
                85                  90                  95

Glu Leu Gly Ala Lys Asp Ile Leu Glu Gly Thr Val Val Ile Ser Glu
            100                 105                 110

Glu Gln Thr Gly Gly Arg Gly Arg Leu Gly Arg Gln Trp Val Ser Pro
            115                 120                 125

Lys Phe Lys Gly Ile Trp Met Ser Ile Ile Leu Arg Pro Asn Ile Glu
130                 135                 140
```

```
Pro Met Glu Ala Ala Lys Ile Thr Gln Ile Ala Ala Ala Val Cys
145                 150                 155                 160

Ser Val Ile Lys Glu Leu Gly Ile Asp Val Tyr Ile Lys Trp Pro Asn
                165                 170                 175

Asp Ile Val Leu Asn Asn Lys Ile Cys Gly Ile Leu Thr Glu Met
            180                 185                 190

Ser Gly Glu Ile Asn Lys Ile Asn Tyr Ile Val Leu Gly Ile Gly Ile
        195                 200                 205

Asn Val Asn Ile Asp Lys Glu Asp Phe Pro Glu Tyr Ile Lys Asp Ile
    210                 215                 220

Ala Thr Ser Ile Lys Ile Glu Thr Gly Leu Asn Ile Gln Arg Lys Glu
225                 230                 235                 240

Leu Ile Ala Lys Ile Phe Asn Lys Phe Glu Ile Leu Tyr Asp Glu Phe
                245                 250                 255

Ile Asn Glu Gly Thr Ile Lys Lys Ser Ile Glu Ile Cys Lys Gly Asn
            260                 265                 270

Ser Ala Leu Leu Gly Lys Glu Val Lys Ile Ile Arg Lys Ser Thr Glu
        275                 280                 285

Val Phe Ala Lys Ala Leu Thr Ile Ala Glu Asp Gly Glu Leu Ile Val
    290                 295                 300

Glu Tyr Asp Asp Gly Lys Val Glu Lys Ile Val Ser Gly Glu Val Ser
305                 310                 315                 320

Ile Arg Gly Met Tyr Gly Tyr Val
                325

<210> SEQ ID NO 10
<211> LENGTH: 18
<212> TYPE: PRT
<213> ORGANISM: Artificial Sequence
<220> FEATURE:
<223> OTHER INFORMATION: peptide substrate biotin ligase target peptide
      sequence

<400> SEQUENCE: 10

Gly Gly Ser Gly Leu Asn Asp Ile Phe Glu Ala Gln Lys Ile Glu Trp
1               5                   10                  15

His Glu

<210> SEQ ID NO 11
<211> LENGTH: 1378
<212> TYPE: DNA
<213> ORGANISM: Artificial Sequence
<220> FEATURE:
<223> OTHER INFORMATION: made by a combination of gene synthesis, PCR
      and Gibson assembly

<400> SEQUENCE: 11
acatatgcgt ggtagccacc accaccatca tcacggtagc gatttgggta agaaattgct      60
ggaggcagca cgcgcaggtc aggatgacga agtgcgtatc ctgatggcga atggcgcgga    120
cgtgaacgct aaagacgaat acggcctgac gccgctgtat ctggcaaccg cccatggcca    180
cctggaaatc gttgaagtcc tgttgaaaaa cggtgccgac gttaatgctg ttgatgcgat    240
tggtttcacc ccgctgcatc tggccgcgtt tatcggtcac ctggagattg cggaggtgct    300
gctgaaacac ggtgcggatg tcaacgcaca ggataagttt ggcaccgcgt tcgacatcag    360
cattggcaac gcaatgagg acctggcgga gattctgcaa aagctgatga aggataacac    420
cgtgccactg aaattgattg ccctgttagc gaacggtgaa tttcactctg cgagcagtt    480
```

-continued

```
gggtgaaacg ctgggaatga gccgggcggc tattaataaa cacattcaga cactgcgtga      540
ctggggcgtt gatgtcttta ccgttccggg taaaggatac agcctgcctg agcctatcca      600
gttacttaat gctaaacaga tattgggtca gctggatggc ggtagtgtag ccgtgctgcc      660
agtgattgac tccacgaatc agtaccttct tgatcgtatc ggagagctta atcgggcga       720 tgcttgcatt gcagaatacc agcaggctgg ccgtggtcgc cggggtcgga atggttttc       780 gccttttggc gcaaacttat atttgtcgat gttctggcgt ctggaacaag cccggcggc       840 ggcgattggt ttaagtctgg ttatcggtat cgtgatggcg aagtattac gcaagctggg       900 tgcagataaa gttcgtgtta atggcctaa tgacctctat ctgcaggatc gcaagctggc       960
aggcattctg gtggagctga ctggcaaaac tggcgatgcg cgcaaatag tcattggagc      1020 cgggatcaac atggcaatgc ccgtgttga agagagtgtc gttaatcagg ggtggatcac      1080
gctgcaggaa gcggggatca atctcgatcg taatacgttg gcggccatgc taatacgtga      1140
attacgtgct gcgttggaac tcttcgaaca agaaggattg gcaccttatc tgtcgcgctg      1200
ggaaaagctg gataatttta ttaatcgccc agtgaaactt atcattggtg ataaagaaat      1260
atttggcatt tcacgcggaa tagacaaaca ggggctttta ttacttgagc aggatggaat      1320 aataaaccc tggatgggcg gtgaaatatc cctgcgtagt gcagaaaaat aactcgag        1378
```

<210> SEQ ID NO 12
<211> LENGTH: 455
<212> TYPE: PRT
<213> ORGANISM: Artificial Sequence
<220> FEATURE:
<223> OTHER INFORMATION: fusion protein

<400> SEQUENCE: 12

```
Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Glu Tyr Gly Leu
        35                  40                  45

Thr Pro Leu Tyr Leu Ala Thr Ala His Gly His Leu Glu Ile Val Glu
    50                  55                  60

Val Leu Leu Lys Asn Gly Ala Asp Val Asn Ala Val Asp Ala Ile Gly
65                  70                  75                  80

Phe Thr Pro Leu His Leu Ala Ala Phe Ile Gly His Leu Glu Ile Ala
                85                  90                  95

Glu Val Leu Leu Lys His Gly Ala Asp Val Asn Ala Gln Asp Lys Phe
            100                 105                 110

Gly Thr Ala Phe Asp Ile Ser Ile Gly Asn Gly Asn Glu Asp Leu Ala
        115                 120                 125

Glu Ile Leu Gln Lys Leu Met Lys Asp Asn Thr Val Pro Leu Lys Leu
    130                 135                 140

Ile Ala Leu Leu Ala Asn Gly Glu Phe His Ser Gly Glu Gln Leu Gly
145                 150                 155                 160

Glu Thr Leu Gly Met Ser Arg Ala Ala Ile Asn Lys His Ile Gln Thr
                165                 170                 175

Leu Arg Asp Trp Gly Val Asp Val Phe Thr Val Pro Gly Lys Gly Tyr
            180                 185                 190

Ser Leu Pro Glu Pro Ile Gln Leu Leu Asn Ala Lys Gln Ile Leu Gly
        195                 200                 205
```

Gln Leu Asp Gly Gly Ser Val Ala Val Leu Pro Val Ile Asp Ser Thr
    210                 215                 220

Asn Gln Tyr Leu Leu Asp Arg Ile Gly Glu Leu Lys Ser Gly Asp Ala
225                 230                 235                 240

Cys Ile Ala Glu Tyr Gln Gln Ala Gly Arg Gly Arg Gly Arg Gly Lys
                245                 250                 255

Trp Phe Ser Pro Phe Gly Ala Asn Leu Tyr Leu Ser Met Phe Trp Arg
                260                 265                 270

Leu Glu Gln Gly Pro Ala Ala Ile Gly Leu Ser Leu Val Ile Gly
            275                 280                 285

Ile Val Met Ala Glu Val Leu Arg Lys Leu Gly Ala Asp Lys Val Arg
            290                 295                 300

Val Lys Trp Pro Asn Asp Leu Tyr Leu Gln Asp Arg Lys Leu Ala Gly
305                 310                 315                 320

Ile Leu Val Glu Leu Thr Gly Lys Thr Gly Asp Ala Ala Gln Ile Val
                325                 330                 335

Ile Gly Ala Gly Ile Asn Met Ala Met Arg Arg Val Glu Glu Ser Val
                340                 345                 350

Val Asn Gln Gly Trp Ile Thr Leu Gln Glu Ala Gly Ile Asn Leu Asp
            355                 360                 365

Arg Asn Thr Leu Ala Ala Met Leu Ile Arg Glu Leu Arg Ala Ala Leu
370                 375                 380

Glu Leu Phe Glu Gln Glu Gly Leu Ala Pro Tyr Leu Ser Arg Trp Glu
385                 390                 395                 400

Lys Leu Asp Asn Phe Ile Asn Arg Pro Val Lys Leu Ile Ile Gly Asp
                405                 410                 415

Lys Glu Ile Phe Gly Ile Ser Arg Gly Ile Asp Lys Gln Gly Ala Leu
            420                 425                 430

Leu Leu Glu Gln Asp Gly Ile Ile Lys Pro Trp Met Gly Gly Glu Ile
            435                 440                 445

Ser Leu Arg Ser Ala Glu Lys
    450                 455

<210> SEQ ID NO 13
<211> LENGTH: 834
<212> TYPE: DNA
<213> ORGANISM: Artificial Sequence
<220> FEATURE:
<223> OTHER INFORMATION: exemplary DNA

<400> SEQUENCE: 13
atggctcaag tacaactgca gcaatctggt acagaggtag ttaaacctgg cgcctctgtc      60
aaattgagtt gcaaggctag tggttacatt ttcacctctt atgacattga ctgggttcgt     120
caaactccag aacaaggatt ggaatggatt gggtggatct ttcctggtga gggctctacg     180
gaatacaacg agaagtttaa gggtagagct cacttagtg tcgataagtc ctcctcaact      240
gcttacatgg agcttacgag acttacatca gaagattcag ccgtgtattt ctgtgctaga    300
ggagattact accgaaggta cttcgactta tggggccagg gtactactgt gacagtcagt    360
tccggaggag gaggttccgg gggtggtggt tctggcggtg gtggatctga tattgagttg    420
actcaatcac ccactatcat gtccgcttct cctggtgaaa gagttaccat gacatgttca    480
gcatctagtt caatcagata catctattgg taccagcaga agcccggctc ctccccacgt    540
ttactgatat acgacacctc aaatgttgca tctggtgttc catcaagatt ttctggatca    600

-continued

```
ggatccggaa caagttattc cctaaccata acaggatgg aagcagagga tgctgccacg    660
tattactgtc aagagtggtc tggctatcct tacacctttg gtggtgggac taagttggaa    720
ttgaaacagg ccgctgcagg gccccgtcaa aagggcgaca caaaatttat tctaaatgca    780
ggtggcggtc tgaacgacat cttcgaggct cagaaaatcg aatggcacga ataa          834
```

```
<210> SEQ ID NO 14
<211> LENGTH: 277
<212> TYPE: PRT
<213> ORGANISM: Artificial Sequence
<220> FEATURE:
<223> OTHER INFORMATION: fusion protein

<400> SEQUENCE: 14
```

```
Met Ala Gln Val Gln Leu Gln Gln Ser Gly Thr Glu Val Val Lys Pro
1               5                   10                  15

Gly Ala Ser Val Lys Leu Ser Cys Lys Ala Ser Gly Tyr Ile Phe Thr
            20                  25                  30

Ser Tyr Asp Ile Asp Trp Val Arg Gln Thr Pro Glu Gln Gly Leu Glu
        35                  40                  45

Trp Ile Gly Trp Ile Phe Pro Gly Glu Gly Ser Thr Glu Tyr Asn Glu
    50                  55                  60

Lys Phe Lys Gly Arg Ala Thr Leu Ser Val Asp Lys Ser Ser Ser Thr
65                  70                  75                  80

Ala Tyr Met Glu Leu Thr Arg Leu Thr Ser Glu Asp Ser Ala Val Tyr
                85                  90                  95

Phe Cys Ala Arg Gly Asp Tyr Tyr Arg Arg Tyr Phe Asp Leu Trp Gly
            100                 105                 110

Gln Gly Thr Thr Val Thr Val Ser Ser Gly Gly Gly Ser Gly Gly
        115                 120                 125

Gly Gly Ser Gly Gly Gly Ser Asp Ile Glu Leu Thr Gln Ser Pro
    130                 135                 140

Thr Ile Met Ser Ala Ser Pro Gly Glu Arg Val Thr Met Thr Cys Ser
145                 150                 155                 160

Ala Ser Ser Ser Ile Arg Tyr Ile Tyr Trp Tyr Gln Gln Lys Pro Gly
                165                 170                 175

Ser Ser Pro Arg Leu Leu Ile Tyr Asp Thr Ser Asn Val Ala Ser Gly
            180                 185                 190

Val Pro Ser Arg Phe Ser Gly Ser Gly Ser Gly Thr Ser Tyr Ser Leu
        195                 200                 205

Thr Ile Asn Arg Met Glu Ala Glu Asp Ala Ala Thr Tyr Tyr Cys Gln
    210                 215                 220

Glu Trp Ser Gly Tyr Pro Tyr Thr Phe Gly Gly Thr Lys Leu Glu
225                 230                 235                 240

Leu Lys Gln Ala Ala Ala Gly Pro Arg Gln Lys Gly Asp Thr Lys Phe
                245                 250                 255

Ile Leu Asn Ala Gly Gly Gly Leu Asn Asp Ile Phe Glu Ala Gln Lys
            260                 265                 270

Ile Glu Trp His Glu
        275
```

```
<210> SEQ ID NO 15
<211> LENGTH: 581
<212> TYPE: PRT
<213> ORGANISM: Artificial Sequence
<220> FEATURE:
<223> OTHER INFORMATION: fusion protein
```

<400> SEQUENCE: 15

```
Met Ala Gln Val Gln Leu Gln Gln Ser Gly Thr Glu Val Val Lys Pro
1               5                   10                  15

Gly Ala Ser Val Lys Leu Ser Cys Lys Ala Ser Gly Tyr Ile Phe Thr
            20                  25                  30

Ser Tyr Asp Ile Asp Trp Val Arg Gln Thr Pro Glu Gln Gly Leu Glu
        35                  40                  45

Trp Ile Gly Trp Ile Phe Pro Gly Glu Gly Ser Thr Glu Tyr Asn Glu
    50                  55                  60

Lys Phe Lys Gly Arg Ala Thr Leu Ser Val Asp Lys Ser Ser Ser Thr
65                  70                  75                  80

Ala Tyr Met Glu Leu Thr Arg Leu Thr Ser Glu Asp Ser Ala Val Tyr
                85                  90                  95

Phe Cys Ala Arg Gly Asp Tyr Tyr Arg Tyr Phe Asp Leu Trp Gly
            100                 105                 110

Gln Gly Thr Thr Val Thr Val Ser Ser Gly Gly Gly Ser Gly Gly
            115                 120                 125

Gly Gly Ser Gly Gly Gly Ser Asp Ile Glu Leu Thr Gln Ser Pro
130                 135                 140

Thr Ile Met Ser Ala Ser Pro Gly Glu Arg Val Thr Met Thr Cys Ser
145                 150                 155                 160

Ala Ser Ser Ser Ile Arg Tyr Ile Tyr Trp Tyr Gln Gln Lys Pro Gly
                165                 170                 175

Ser Ser Pro Arg Leu Leu Ile Tyr Asp Thr Ser Asn Val Ala Ser Gly
            180                 185                 190

Val Pro Ser Arg Phe Ser Gly Ser Gly Ser Gly Thr Ser Tyr Ser Leu
        195                 200                 205

Thr Ile Asn Arg Met Glu Ala Glu Asp Ala Ala Thr Tyr Tyr Cys Gln
    210                 215                 220

Glu Trp Ser Gly Tyr Pro Tyr Thr Phe Gly Gly Gly Thr Lys Leu Glu
225                 230                 235                 240

Leu Lys Gln Ala Ala Ala Gly Pro Arg Gln Lys Gly Asp Thr Lys Phe
                245                 250                 255

Ile Leu Asn Ala Met Lys Asp Asn Thr Val Pro Leu Lys Leu Ile Ala
            260                 265                 270

Leu Leu Ala Asn Gly Glu Phe His Ser Gly Glu Gln Leu Gly Glu Thr
        275                 280                 285

Leu Gly Met Ser Arg Ala Ala Ile Asn Lys His Ile Gln Thr Leu Arg
    290                 295                 300

Asp Trp Gly Val Asp Val Phe Thr Val Pro Gly Lys Gly Tyr Ser Leu
305                 310                 315                 320

Pro Glu Pro Ile Gln Leu Leu Asn Ala Lys Gln Ile Leu Gly Gln Leu
                325                 330                 335

Asp Gly Gly Ser Val Ala Val Leu Pro Val Ile Asp Ser Thr Asn Gln
            340                 345                 350

Tyr Leu Leu Asp Arg Ile Gly Glu Leu Lys Ser Gly Asp Ala Cys Ile
        355                 360                 365

Ala Glu Tyr Gln Gln Ala Gly Arg Gly Arg Gly Arg Lys Trp Phe
    370                 375                 380

Ser Pro Phe Gly Ala Asn Leu Tyr Leu Ser Met Phe Trp Arg Leu Glu
385                 390                 395                 400

Gln Gly Pro Ala Ala Ala Ile Gly Leu Ser Leu Val Ile Gly Ile Val
```

```
                         405                 410                 415
Met Ala Glu Val Leu Arg Lys Leu Gly Ala Asp Lys Val Arg Val Lys
            420                 425                 430

Trp Pro Asn Asp Leu Tyr Leu Gln Asp Arg Lys Leu Ala Gly Ile Leu
            435                 440                 445

Val Glu Leu Thr Gly Lys Thr Gly Asp Ala Ala Gln Ile Val Ile Gly
            450                 455                 460

Ala Gly Ile Asn Met Ala Met Arg Arg Val Glu Glu Ser Val Val Asn
465                 470                 475                 480

Gln Gly Trp Ile Thr Leu Gln Glu Ala Gly Ile Asn Leu Asp Arg Asn
                485                 490                 495

Thr Leu Ala Ala Met Leu Ile Arg Glu Leu Arg Ala Ala Leu Glu Leu
            500                 505                 510

Phe Glu Gln Glu Gly Leu Ala Pro Tyr Leu Ser Arg Trp Glu Lys Leu
            515                 520                 525

Asp Asn Phe Ile Asn Arg Pro Val Lys Leu Ile Ile Gly Asp Lys Glu
            530                 535                 540

Ile Phe Gly Ile Ser Arg Gly Ile Asp Lys Gln Gly Ala Leu Leu Leu
545                 550                 555                 560

Glu Gln Asp Gly Ile Ile Lys Pro Trp Met Gly Glu Ile Ser Leu
                565                 570                 575

Arg Ser Ala Glu Lys
            580

<210> SEQ ID NO 16
<211> LENGTH: 151
<212> TYPE: PRT
<213> ORGANISM: Artificial Sequence
<220> FEATURE:
<223> OTHER INFORMATION: fusion protein

<400> SEQUENCE: 16

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Met Ala Asn Gly Ala Asp Val Asn Ala Lys Asp Glu Tyr Gly Leu
            35                  40                  45

Thr Pro Leu Tyr Leu Ala Thr Ala His Gly His Leu Glu Ile Val Glu
            50                  55                  60

Val Leu Leu Lys Asn Gly Ala Asp Val Asn Ala Val Asp Ala Ile Gly
65                  70                  75                  80

Phe Thr Pro Leu His Leu Ala Ala Phe Ile Gly His Leu Glu Ile Ala
            85                  90                  95

Glu Val Leu Leu Lys His Gly Ala Asp Val Asn Ala Gln Asp Lys Phe
            100                 105                 110

Gly Thr Ala Phe Asp Ile Ser Ile Gly Asn Gly Asn Glu Asp Leu Ala
            115                 120                 125

Glu Ile Leu Gln Lys Leu Gly Gly Gly Leu Asn Asp Ile Phe Glu Ala
            130                 135                 140

Gln Lys Ile Glu Trp His Glu
145                 150
```

PROXIMITY ASSAY FOR IN SITU DETECTION OF TARGETS

FIELD

Disclosed embodiments concern detecting targets in a sample, typically targets located proximally in a sample, and even more particularly concern a proximity assay using a biotin ligase conjugate and a biotin ligase substrate conjugate. Reagents and kits useful for practicing the method also are described.

BACKGROUND

Networks of protein-protein interactions are the hallmarks of biological systems. Protein-protein interactions form signal pathways that regulate all aspects of cellular functions in normal and cancerous cells. Methods have been developed for detecting protein-protein interactions, such as transient receptor tyrosine kinase dimerization and complex formation after extracellular growth factor activation; however, these methods are not particularly designed to be used on formalin fixed paraffin embedded tissues.

A proximity ligation assay recently has been developed by OLink AB. This is the only known commercial product for in situ detection of protein-protein interactions on formalin fixed paraffin embedded tissue. Proximity ligation assay technology uses DNA ligases to generate a padlock circular DNA template, as well as Phi29 DNA polymerase for rolling circle amplification. These enzymes are expensive. Moreover, these enzymes are not amenable for use with automated systems and methods. For these reasons, proximity ligation assays are not considered generally useful for commercial applications.

As understanding disarrayed cellular pathway(s) becomes increasingly important to personalized diagnosis and treatment for cancer patients, in situ protein-protein detection in formalin fixed paraffin embedded tissue becomes an unmet medical need in tissue diagnosis.

SUMMARY

Disclosed is a proximity assay for tissue diagnostics. Certain disclosed embodiments of the present invention concern an in situ detection method that utilizes enzymatic biotinylation reactions to detect targets in a sample. Disclosed embodiments address the deficiencies noted above concerning proximity ligation assays for in situ use with formalin fixed paraffin embedded samples, particularly on automated staining platforms. The assay provides for the detection of target molecules and the proximity thereof while maintaining the cellular context of the sample.

Certain embodiments use biotin ligase, such as an enzyme from *E. coli*, and an appropriate peptide substrate (such as BTS, a 18 amino-acid long peptide) for sensitive and specific detection of protein-protein interactions in formalin fixed paraffin embedded tissue samples. Because biotin ligase can efficiently biotinylate an appropriate peptide substrate in the presence of biotin, and the reaction can only occur when the enzyme makes physical contact with the peptide substrate (See FIG. 1), biotin ligase and the substrate can be separately conjugated to two antibodies that recognize targets of interest (A and B) respectively. When targets of interest are in sufficiently close proximity, e.g. receptor dimerization on cell membrane that triggers a signaling relay, binding of antibody conjugates to their respective target protein brings biotin ligase and the peptide substrate in sufficiently close proximity to allow biotinylation of the substrate. Targets do not have to reside on the cell surface. Instead, targets can be in any cellular compartment. In addition, targets do not have to be proteins that are recognized by antibodies. Any other biomolecule e.g. lipid and nucleic acid, can be detected using the disclosed proximity detection embodiments.

One disclosed embodiment comprises contacting a sample with a first conjugate probe comprising a biotin ligase and a specific binding moiety for associating with a first target, and contacting the sample with a second conjugate probe comprising a biotin ligase substrate and a specific binding moiety for associating with a second target under conditions that allow biotinylation of the substrate. In some samples, the first target is located proximal to the second target. The sample may be contacted with the first probe and the second probe either sequentially or simultaneously. Although any specific binding moiety can be adapted for use with the present invention, working embodiments typically used antibodies, such as a primary antibody for the first target, the second target, or both. In certain embodiments, a primary antibody was used from a first species, and a second probe conjugate comprised a second species anti-primary antibody.

The conditions that allow biotinylation of the substrate include addition of biotin and ATP. The method may also comprise contacting the sample with a streptavidin-enzyme substrate that forms a specific binding pair with biotin. For certain working embodiments, the enzyme was horseradish peroxidase (HRP) and the method further comprised staining with diaminobenzidine (DAB)/$H_2O_2$. In other working embodiments, the enzyme was alkaline phosphatase and the method further comprised staining with alkaline phosphatase red (fast red).

The method can be adapted for detecting biological targets generally, such as nucleic acid targets and protein targets, with working embodiments exemplifying the invention using protein targets. Accordingly, in certain embodiments the first target was a protein, the second target was a protein, or both targets were proteins, such as p95, HER1, HER2, HER3 and HER4.

Disclosed embodiments can be used to qualitatively determine a distance between a first and second target. Alternatively, disclosed embodiments can be used to quantitatively determine a distance between the first and second targets. This embodiment comprises contacting proximally located targets on a first sample from a tissue with a first set of probes designed to be located at a first known distance when bound to the targets. The first distance does not allow for biotinylation. A second sample from the tissue is contacted with a second set of probes designed to be located at a second known distance between targets when bound to the targets under conditions for biotinylation, wherein the second distance allows biotinylation, thereby allowing a quantitative determination of distance between proximally located targets.

Signal amplification also can be used, if desired. For example, certain disclosed embodiments comprised using tyramide amplification. Accordingly, one disclosed embodiment comprised contacting the sample with a first primary antibody for the first target, and contacting the substrate with a second primary antibody for the second target. TSA was then performed. The sample was then contacted with a first conjugate probe comprising an anti-antibody for the first primary antibody and a biotin ligase, and with a second conjugate probe comprising an anti-hapten antibody and a biotin ligase substrate. Biotin and ATP were added, followed by a streptavidin:enzyme conjugate, such as horseradish peroxidase (HRP) and staining with diaminobenzidine (DAB)/$H_2O_2$.

A particular disclosed embodiment concerns a method for detecting HER2:HER3 dimers. One disclosed embodiment comprised contacting a tissue sample with a primary anti-HER2 antibody and with a primary anti-HER3 antibody. The sample was then contacted with a conjugate probe comprising an anti-antibody for the HER3 antibody and horseradish peroxidase. TSA was performed with hapten deposition. The sample was then contacted with a first conjugate probe comprising a biotin ligase and an anti-antibody for the HER2 primary antibody, and a second conjugate probe comprising a biotin ligase substrate and an anti-hapten antibody. Biotin and ATP were added, followed by a conjugate probe comprising streptavidin and an enzyme, and finally a substrate for the enzyme.

Conjugate probes for practicing the disclosed method, and methods for making the conjugate probes, also are described. A first disclosed conjugate probe comprises biotin ligase conjugated to a specific binding moiety, such as a hapten or an antibody, including a primary antibody for a selected target such as p95, HER1, HER2, HER3 or HER4, an anti-antibody, or an anti-hapten antibody. Biotin ligase can be obtained, for example, from *Escherichia Coli, Thermococcus kodakarensis, Thermococcus zilligii* AN1, *Thermococcus gammatolerans* EJ3, *Pyrococcus abyssi* GE5, *Pyrococcus horikoshii* OT3, and *Clostridium botulinum* C str. The biotin ligase may be directly conjugated to the specific binding moiety, conjugated to the specific binding moiety through a linker, with certain working embodiments using $PEG_2$ to $PEG_{20}$ linkers, and/or fusion proteins may be used. The conjugate may have one biotin ligase per specific binding moiety, but working embodiments typically included 1 to 5 biotin ligases per antibody.

Certain disclosed conjugates have a formula:

$$(SBM)\text{-}([linker]_m\text{-}(BL/BLS)]_n$$

where SBM is specific binding moiety, BL is biotin ligase and BLS is biotin ligase substrate, m is 0 to 5 and n is 1 to 10. Examples of biotin ligase conjugate probes include:

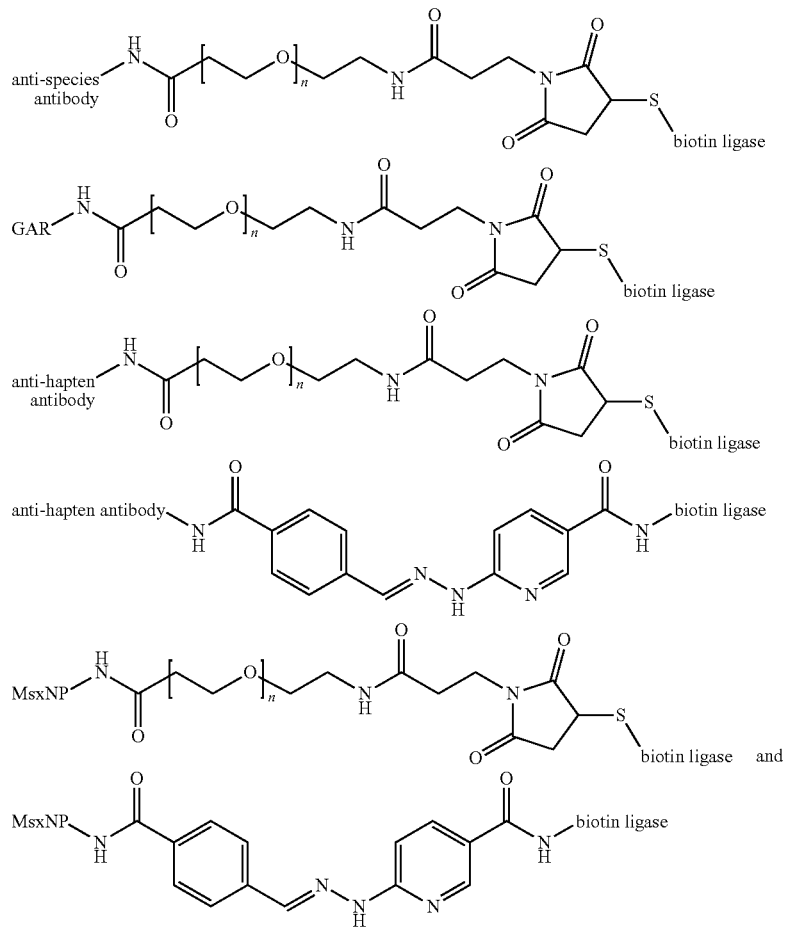

where n is 2 to 20.

A second disclosed conjugate probe comprises a biotin ligase substrate conjugated to a specific binding moiety. The biotin ligase substrate may be directly conjugated to the specific binding moiety, conjugated to the specific binding moiety through a linker, such as a $PEG_2$ to $PEG_{20}$ linker, and/or fusion proteins may be used. While a single biotin ligase substrate may be coupled to the specific binding moiety, more typically 2 to 5 biotin substrate molecules were coupled to antibody specific binding moieties in working embodiments. Exemplary biotin ligase substrate conjugate probes include

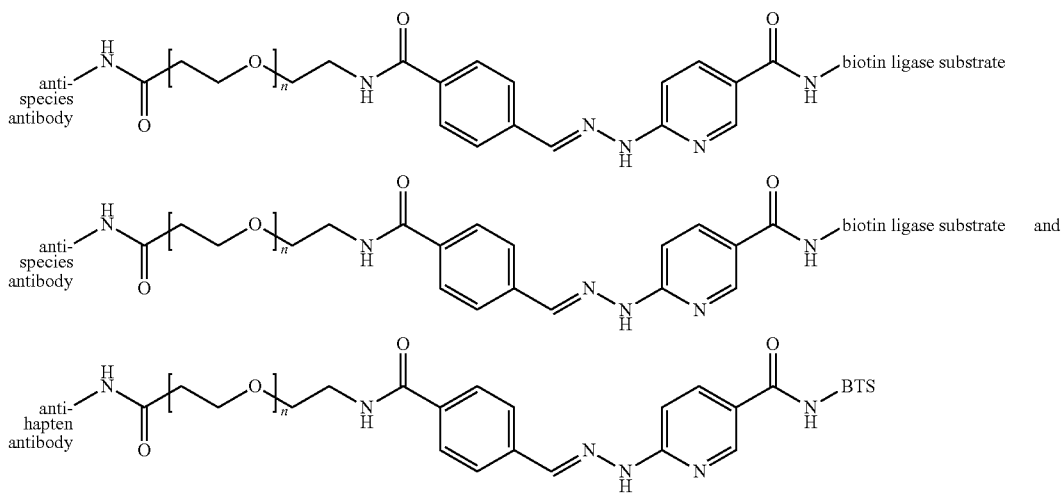

where n is 2-20.

Conjugates also can be described with respect to the sample. For example, disclosed conjugates also include a sample, a first probe comprising a biotin ligase and a specific binding moiety associated with a first target of the sample, and a second probe comprising a biotin ligase substrate and a second specific binding moiety associated with a second target of the sample. The conjugate may comprise a biotinylated substrate. The conjugate may further comprise streptavidin associated with biotin, wherein the streptavidin is coupled to a signal generating moiety, such as an enzyme, a hapten, a luminophore, and/or a fluorophore.

A method for treating a subject also is disclosed. One embodiment comprised obtaining a proximity assay according to disclosed embodiments of the present invention for two targets in a sample, wherein the assay is diagnostic for a malady. A therapeutic selected for treating the malady is administered to the subject upon obtaining positive proximity assay results. Obtaining an assay can comprise receiving assay results, or performing the assay. One embodiment of the method may comprise administering a therapeutically effective amount of an agent that disrupts a HER protein complex. For example, if a first HER protein is HER2 and a second HER protein is HER2, the therapeutic may be trastuzumab. If a first HER protein is HER3 and a second HER protein is HER2 or the first HER protein is HER2 and a second HER protein is HER3, the therapeutic may be pertuzumab.

Kits for practicing disclosed embodiments also are disclosed. An exemplary kit comprises at least one conjugate selected from a first conjugate comprising biotin ligase and a specific binding moiety and a second conjugate comprising a biotin ligase substrate and a specific binding moiety.

The foregoing and other objects, features, and advantages of the invention will become more apparent from the following detailed description, which proceeds with reference to the accompanying figures.

Additional features of the present disclosure will become apparent to those skilled in the art upon consideration of the following detailed description of illustrative embodiments exemplifying the best mode of carrying out the disclosure as presently perceived.

DESCRIPTION OF THE SEQUENCE LISTING

Figure 1:
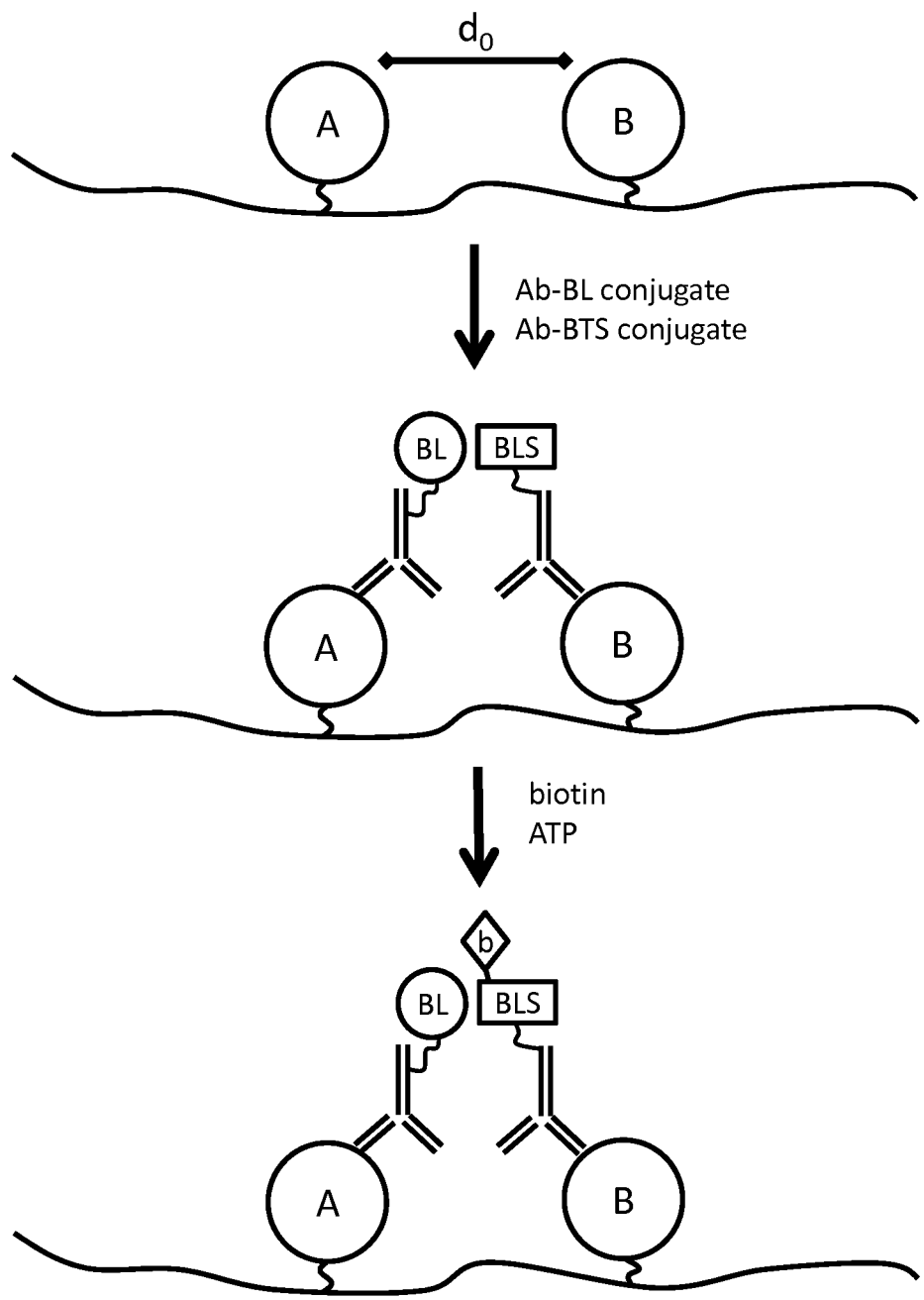
FIG. 1 is a schematic depiction of one embodiment of the present invention for in situ proximity detection of a first target A and a second target B using a biotin ligase (e.g. from BirA) and a peptide substrate (e.g. BTS), such that the biotinylated product can be subsequently detected using, for example, Streptavidin-HRP or Streptavidin-AP, with or without signal amplification.
Figure 2:
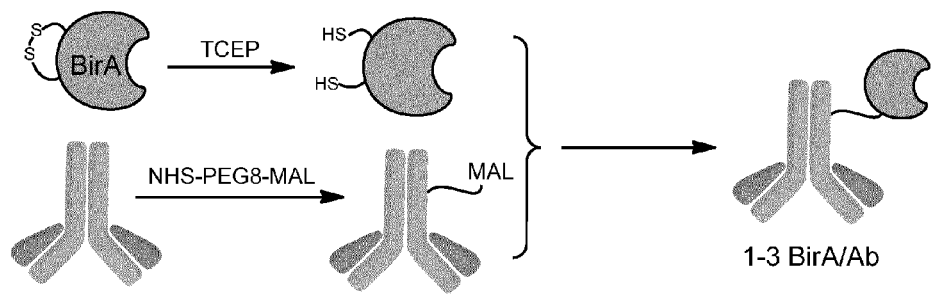
FIG. 2 schematically illustrates one embodiment of a method for chemically conjugating a biotin ligase to an antibody.

SEQ. ID Nos. 1-9 are sequences for, or sequences used to make, biotin ligase from various sources.

```
SEQ. ID No. 1:
CATATGGGAAGCGGCCATCACCACCACCATCACGGAGGCGGAGGTTCAGGCTGCA

GCAACCTGTCTACCTGTGTGTTGAAGGATAACACCGTGCCAC

SEQ. ID No. 2:
GCTGTCGACTTATTTTTCTGCACTACGCAGGGATA

SEQ. ID No. 3:
MGSGHHHHHHGGGGSGCSNLSTCVLKDNTVPLKLIALLANGEFHSGEQLGETLGMSR

AAINKHIQTLRDWGVDVFTVPGKGYSLPEPIQLLNAKQILGQLDGGSVAVLPVIDSTNQY

LLDRIGELKSGDACIAEYQQAGRGRRGRKWFSPFGANLYLSMFWRLEQGPAAAIGLSL

VIGIVMAEVLRKLGADKVRVKWPNDLYLQDRKLAGILVELTGKTGDAAQIVIGAGINMAM

RRVEESVVNQGWITLQEAGINLDRNTLAAMLIRELRAALELFEQEGLAPYLSRWEKLDN

FINRPVKLIIGDKEIFGISRGIDKQGALLLEQDGIIKPWMGGEISLRSAEK

SEQ. ID No. 4:
MEWNVIRLDEVDSTNEYAKKLIPDVSEGTVVVAKRQTSGRGRKGRAWASPEGGLWMS

VILKPPMIDPRLVFVGALAVSDTLRDFGIGAWIKWPNDVWVGNRKISGVLTEVKGDFVIM

GVGLNVNNEIPDGLKETATSMMEALGEPVDIGEVLERLLEYLGRWYKTFLENPPLVVEE

VRGRTMLIGKEVRVLLDGNDLVGRVITISDDGSLILDVDGQTVKVVYGDVSVRINR

SEQ. ID No. 5:
MWKIIHLDEVDSTNDYAKSIAEESPEGTVVIAKRQTAGKGRKGRSWASPEGGLWMSVIL

KPERTDPRLVFVGALAVVDTLADFGIKGWIKWPNDVWVEGKKIAGVLTEGKAEKFVVM

GIGLNVNNPVPEGLEREATSMIYHTGMELPLDSVLDRLLFHLGGWYGVYKERPELLVEK

LRQRTFILGKAVRVTEDDKTIIGRALDVLDDGSLLLEVGGELRRILYGDVSVRPL

SEQ. ID No. 6:
MEWNIITLDEVDSTNEYARRIAPTAPEGTVVVAKRQTAGRGRKGRRWASPEGGLWMT

VILKPKSGPEHVTKLVFVGALAVLDTLHEYGIRGELKWPNDVLVDGKKIAGILSECRLNHF

ALLGIGLNVNNEIPDELRESAVSMKEVLGRAIDLEEVLNRVLRNLSRWYGLFRNGRHGEI

LKAVKGSSAVLGKRVRIIEDGEIIAEGIAVDIDNSGALILKGEENTVRVLYGDVSLRFS

SEQ. ID No. 7:
MLGLKTSVIGRTIIYFQEVASTNDYAKAENLEEGTVIVADRQIKGHGRLERKWESPEGGL

WMSVVLTPRVSQEDLPKIVFLGALAVVETLREFSIDARIKWPNDVLVNYRKVAGVLVEAK

GEKVILGIGLNVNNKVPDGATSMKQELGSEIPMLNVFKTLVKTLDSLYLKFLESPGKILER

AKRSMILGVRVKVLSDGEVEAEGIAEDVDEFGRLIVRLDDGRVKKILYGDVSLRFL

SEQ. ID No. 8:
MLGLKTSIIGRRVIYFQEITSTNEFAKTSYLEEGTVIVADKQTMGHGRLNRKWESPEGGL

WLSIVLSPKVPQKDLPKIVFLGAVGVVETLKEFSIDGRIKWPNDVLVNYKKIAGVLVEGKG

DKIVLGIGLNVNNKVPNGATSMKLELGSEVPLLSVFRSLITNLDRLYLNFLKNPMDILNLV

RDNMILGVRVKILGDGSFEGIAEDIDDFGRLIIRLDSGEVKKVIYGDVSLRFL
```

SEQ. ID No. 9:
MKEEIISLLKENKDNFISGEKISEKFGITRAAIWKYMKAIKNEGYKIESVSRKGYKLISSPDL

LTFQEINPYLTTNYIGKNIMYFNTIDSTNNKAKELGAKDILEGTVVISEEQTGGRGRLGRQ

WVSPKFKGIWMSIILRPNIEPMEAAKITQIAAAAVCSVIKELGIDVYIKWPNDIVLNNKKICG

ILTEMSGEINKINYIVLGIGINVNIDKEDFPEYIKDIATSIKIETGLNIQRKELIAKIF-
NKFEILYD

EFINEGTIKKSIEICKGNSALLGKEVKIIRKSTEVFAKALTIAEDGELIVEYDDGKVEKIVSG

EVSIRGMYGYV

SEQ. ID No. 10 is an amino acid sequence for an exemplary biotin
ligase substrate:
GGSGLNDIFEAQKIEWHE SEQ. ID No. 11 is a DNA sequence that encodes a biotin ligase
fused to a specific binding moiety.
ACATATGCGTGGTAGCCACCACCACCATCATCACGGTAGCGATTTGGGTAAGAAAT

TGCTGGAGGCAGCACGCGCAGGTCAGGATGACGAAGTGCGTATCCTGATGGCGAA

TGGCGCGGACGTGAACGCTAAAGACGAATACGGCCTGACGCCGCTGTATCTGGCA

ACCGCCCATGGCCACCTGGAAATCGTTGAAGTCCTGTTGAAAAACGGTGCCGACGT

TAATGCTGTTGATGCGATTGGTTTCACCCCGCTGCATCTGGCCGCGTTTATCGGTCA

CCTGGAGATTGCGGAGGTGCTGCTGAAACACGGTGCGGATGTCAACGCACAGGAT

AAGTTTGGCACCGCGTTCGACATCAGCATTGGCAACGGCAATGAGGACCTGGCGG

AGATTCTGCAAAAGCTGATGAAGGATAACACCGTGCCACTGAAATTGATTGCCCTGT

TAGCGAACGGTGAATTTCACTCTGGCGAGCAGTTGGGTGAAACGCTGGGAATGAGC

CGGGCGGCTATTAATAAACACATTCAGACACTGCGTGACTGGGGCGTTGATGTCTT

TACCGTTCCGGGTAAAGGATACAGCCTGCCTGAGCCTATCCAGTTACTTAATGCTAA

ACAGATATTGGGTCAGCTGGATGGCGGTAGTGTAGCCGTGCTGCCAGTGATTGACT

CCACGAATCAGTACCTTCTTGATCGTATCGGAGAGCTTAAATCGGGCGATGCTTGC

ATTGCAGAATACCAGCAGGCTGGCCGTGGTCGCCGGGGTCGGAAATGGTTTTCGC

CTTTTGGCGCAAACTTATATTTGTCGATGTTCTGGCGTCTGGAACAAGGCCCGGCG

GCGGCGATTGGTTTAAGTCTGGTTATCGGTATCGTGATGGCGGAAGTATTACGCAA

GCTGGGTGCAGATAAAGTTCGTGTTAAATGGCCTAATGACCTCTATCTGCAGGATC

GCAAGCTGGCAGGCATTCTGGTGGAGCTGACTGGCAAAACTGGCGATGCGGCGCA

AATAGTCATTGGAGCCGGGATCAACATGGCAATGCGCCGTGTTGAAGAGAGTGTCG

TTAATCAGGGGTGGATCACGCTGCAGGAAGCGGGGATCAATCTCGATCGTAATACG

TTGGCGGCCATGCTAATACGTGAATTACGTGCTGCGTTGGAACTCTTCGAACAAGA

AGGATTGGCACCTTATCTGTCGCGCTGGGAAAAGCTGGATAATTTTATTAATCGCCC

AGTGAAACTTATCATTGGTGATAAAGAAATATTTGGCATTTCACGCGGAATAGACAA

ACAGGGGGCTTTATTACTTGAGCAGGATGGAATAATAAAACCCTGGATGGGCGGTG

AAATATCCCTGCGTAGTGCAGAAAAATAACTCGAG

SEQ. ID No. 12 is an amino acid sequence for a fusion protein
corresponding to that encoded by SEQ. ID NO. 11.
MRGSHHHHHHGSDLGKKLLEAARAGQDDEVRILMANGADVNAKDEYGLTPLYLATAH

GHLEIVEVLLKNGADVNAVDAIGFTPLHLAAFIGHLEIAEVLLKHGADVNAQDKFGTAFDI

SIGNGNEDLAEILQKLMKDNTVPLKLIALLANGEFHSGEQLGETLGMSRAAINKHIQTLR

DWGVDVFTVPGKGYSLPEPIQLLNAKQILGQLDGGSVAVLPVIDSTNQYLLDRIGELKS

-continued

GDACIAEYQQAGRGRRGRKWFSPFGANLYLSMFWRLEQGPAAAIGLSLVIGIVMAEV

LRKLGADKVRVKWPNDLYLQDRKLAGILVELTGKTGDAAQIVIGAGINMAMRRVEESV

VNQGWITLQEAGINLDRNTLAAMLIRELRAALELFEQEGLAPYLSRWEKLDNFINRPV

KLIIGDKEIFGISRGIDKQGALLLEQDGIIKPWMGGEISLRSAEK#

SEQ. ID No. 13 is a DNA sequence that encodes a fusion protein comprising a biotin ligase substrate.
ATGGCTCAAGTACAACTGCAGCAATCTGGTACAGAGGTAGTTAAACCTGGCGCCTC

TGTCAAATTGAGTTGCAAGGCTAGTGGTTACATTTTCACCTCTTATGACATTGACTG

GGTTCGTCAAACTCCAGAACAAGGATTGGAATGGATTGGGTGGATCTTTCCTGGTG

AGGGCTCTACGGAATACAACGAGAAGTTTAAGGGTAGAGCTACACTTAGTGTCGAT

AAGTCCTCCTCAACTGCTTACATGGAGCTTACGAGACTTACATCAGAAGATTCAGCC

GTGTATTTCTGTGCTAGAGGAGATTACTACCGAAGGTACTTCGACTTATGGGCCA

GGGTACTACTGTGACAGTCAGTTCCGGAGGAGGAGGTTCCGGGGGTGGTGGTTCT

GGCGGTGGTGGATCTGATATTGAGTTGACTCAATCACCCACTATCATGTCCGCTTCT

CCTGGTGAAAGAGTTACCATGACATGTTCAGCATCTAGTTCAATCAGATACATCTATT

GGTACCAGCAGAAGCCCGGCTCCTCCCCACGTTTACTGATATACGACACCTCAAAT

GTTGCATCTGGTGTTCCATCAAGATTTTCTGGATCAGGATCCGGAACAAGTTATTCC

CTAACCATAAACAGGATGGAAGCAGAGGATGCTGCCACGTATTACTGTCAAGAGTG

GTCTGGCTATCCTTACACCTTTGGTGGTGGGACTAAGTTGGAATTGAAACAGGCCG

CTGCAGGGCCCCGTCAAAAGGGCGACACAAAATTTATTCTAAATGCAGGTGGCGGT

CTGAACGACATCTTCGAGGCTCAGAAAATCGAATGGCACGAATAA

SEQ. ID No. 14 is an amino acid sequence for a fusion protein corresponding to that encoded by SEQ. ID NO. 13.
MAQVQLQQSGTEVVKPGASVKLSCKASGYIFTSYDIDWVRQTPEQGLEWIGWIFPGEG

STEYNEKFKGRATLSVDKSSSTAYMELTRLTSEDSAVYFCARGDYYRRYFDLWGQGTT

VTVSSGGGGSGGGGSGGGGSDIELTQSPTIMSASPGERVTMTCSASSSIRYIYWYQQK

PGSSPRLLIYDTSNVASGVPSRFSGSGSGTSYSLTINRMEAEDAATYYCQEWSGYPYT

FGGGTKLELKQAAAGPRQKGDTKFILNAGGGLNDIFEAQKIEWHE#

SEQ. ID No. 15 is an amino acid sequence for an SCFV fused to biotin ligase.
MAQVQLQQSGTEVVKPGASVKLSCKASGYIFTSYDIDWVRQTPEQGLEWIGWIFPGEG

STEYNEKFKGRATLSVDKSSSTAYMELTRLTSEDSAVYFCARGDYYRRYFDLWGQGTT

VTVSSGGGGSGGGGSGGGGSDIELTQSPTIMSASPGERVTMTCSASSSIRYIYWYQQK

PGSSPRLLIYDTSNVASGVPSRFSGSGSGTSYSLTINRMEAEDAATYYCQEWSGYPYT

FGGGTKLELKQAAAGPRQKGDTKFILNAMKDNTVPLKLIALLANGEFHSGEQLGETLG

MSRAAINKHIQTLRDWGVDVFTVPGKGYSLPEPIQLLNAKQILGQLDGGSVAVLPVIDS

TNQYLLDRIGELKSGDACIAEYQQAGRGRRGRKWFSPFGANLYLSMFWRLEQGPAA

AIGLSLVIGIVMAEVLRKLGADKVRVKWPNDLYLQDRKLAGILVELTGKTGDAAQIVIG

AGINMAMRRVEESVVNQGWITLQEAGINLDRNTLAAMLIRELRAALELFEQEGLAPYL

SRWEKLDNFINRPVKLIIGDKEIFGISRGIDKQGALLLEQDGIIKPWMGGEISLRSAEK

SEQ. ID No. 16 is an amino acid sequence for a fusion protein comprising a biotin ligase substrate fused to a DARPin.
MRGSHHHHHHGSDLGKKLLEAARAGQDDEVRILMANGADVNAKDEYGLTPLYLATAH

GHLEIVEVLLKNGADVNAVDAIGFTPLHLAAFIGHLEIAEVLLKHGADVNAQDKFGTAFDI

SIGNGNEDLAEILQKLGGGLNDIFEAQKIEWHE#

DETAILED DESCRIPTION

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8). Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes."

All publications, patent applications, patents, and other references mentioned herein are incorporated by reference in their entirety. All GenBank Accession numbers are herein incorporated by reference as they appeared in the database on Jun. 8, 2011. In case of conflict, the present specification, including explanations of terms, will control. In addition, the materials, methods, and examples are illustrative and not intended to be limiting.

In order to facilitate review of the various embodiments of this disclosure, the following explanations of specific terms are provided:

Administration: To provide or give a subject an agent, for example, a composition that includes a monoclonal antibody that specifically binds HER2, by any effective route. Exemplary routes of administration include, but are not limited to, oral, injection (such as subcutaneous, intramuscular, intradermal, intraperitoneal, and intravenous), sublingual, rectal, transdermal (e.g., topical), intranasal, vaginal and inhalation routes.

Agent: Any substance or any combination of substances that is useful for achieving an end or result; for example, a substance or combination of substances useful for decreasing or decreasing a protein-protein interaction. In some embodiments, the agent is a therapeutic agent, such as a therapeutic agent for the treatment of cancer.

Antibody: A polypeptide ligand including at least a light chain or heavy chain immunoglobulin variable region which specifically binds an epitope of an antigen or a fragment thereof. Antibodies include intact immunoglobulins and the variants of them well known in the art, such as Fab', F(ab)'$_2$ fragments, single chain Fv proteins (scFv), and disulfide stabilized Fv proteins (dsFv). A scFv protein is a fusion protein in which a light chain variable region of an antibody and a heavy chain variable region of an antibody are bound by a linker, while in dsFvs, the chains have been mutated to introduce a disulfide bond to stabilize the association of the chains. The term also includes genetically engineered forms such as chimeric antibodies (for example, humanized murine antibodies) and heteroconjugate antibodies (such as, bispecific antibodies). See also, *Pierce Catalog and Handbook*, 1994-1995 (Pierce Chemical Co., Rockford, Ill.); Kuby, J., *Immunology*, 3$^{rd}$ Ed., W.H. Freeman & Co., New York, 1997.

The antibodies disclosed herein specifically bind a defined target (or multiple targets, in the case of a bispecific antibody). Thus, an antibody that specifically binds to HER2 is an antibody that binds substantially to HER2, for example cells or tissue expressing HER2. It is, of course, recognized that a certain degree of non-specific interaction may occur between an antibody and a non-target (e.g., a cell that does not express HER2).

Typically, specific binding results in a much stronger association between the antibody and protein or cells bearing the antigen than between the antibody and protein or cells lacking the antigen. Specific binding typically results in greater than a 2-fold increase 4, such as greater than 5-fold, greater than 10-fold, or greater than 100-fold increase, in amount of bound antibody (per unit time) to a protein including the epitope or cell or tissue expressing the target epitope as compared to a protein or cell or tissue lacking this epitope. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select monoclonal antibodies specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

ATP: Adenosine triphosphate is a nucleoside triphosphate used in cells as a coenzyme.

Biological sample: A biological specimen containing biological molecules, including genomic DNA, RNA (including mRNA and microRNA), nucleic acids, proteins, peptides, and/or combinations thereof. In some examples, the biological sample is obtained from a subject. In other examples, the biological sample is a cell culture, including a cell culture grown from a biological sample obtained from a subject. Biological samples include all clinical samples useful for detecting disease (e.g., cancer) in subjects, including, but not limited to, cells, tissues, and bodily fluids, such as blood, derivatives and fractions of blood (such as serum); as well as biopsied or surgically removed tissue, for example tissues that are unfixed, frozen, or fixed in formalin or paraffin. In a particular example, a biological sample is obtained from a subject having or suspected of having a tumor; for example, a subject having or suspected of having breast cancer, ovarian cancer, stomach cancer or uterine cancer. In some embodiments, the subject has or is suspected of having a carcinoma.

Biotin Ligase: Certain disclosed embodiments use enzymes capable of biotinylating a substrate, such as biotin-[acetyl-CoA-carboxylase] ligase. Enzymes suitable for practicing the disclosed embodiments also are referred to by other names by persons of ordinary skill in the art, as indicated by the KEGG entry http://www.genome.ip/dbget-bin/www_bget?ec:6.3.4.15. All such enzymes are referred to herein collectively as biotin ligases. Enzymatic biotinylation using a biotin ligase allows biotin to be linked to a residue present in a protein. This biotinylation reaction can also go to completion, meaning that the product is generated with high uniformity and can be linked to streptavidin in a defined orientation. Enzymatic biotinylation is most often accomplished by targeting a particular substrate, with certain disclosed embodiments targeting a 15 amino acid peptide, such as AviTag or Acceptor Peptide (AP). One example of a suitable biotin ligase is from BirA. The biotin ligase gene of *Escherichia coli* produces a 35.3-kDal [321 amino acids] bifunctional protein containing a biotin-operon-repressor and biotin-holoenzyme-synthetase activities. Biotin ligase also has been produced from other species, including *Pseudomonas Mutabilis*. The biotin ligase Kd for BTS is no less than 25 µM. For certain disclosed embodiments, biotin ligase and BTS conjugates are used at about 30 µM, i.e. more than 800 fold less than the Kd. The potential target independent binding of biotin ligase to BTS using such conjugates therefore is very minimal.

Breast cancer: A neoplastic tumor of breast tissue that is or has potential to be malignant. Approximately 30% of breast cancers exhibit overexpression of HER2; overexpression of HER2 is associated with increased disease recurrence and worse prognosis. The most common type of breast cancer is breast carcinoma, such as ductal carcinoma. Ductal carcinoma in situ is a non-invasive neoplastic condition of the ducts. Lobular carcinoma is not an invasive disease but is an indicator that a carcinoma may develop. Infiltrating (malignant) carcinoma of the breast can be divided into stages (I, IIA, IIB, IIIA, IIIB, and IV). See, for example, Bonadonna et al, (eds), *Textbook of Breast Cancer: A clinical Guide the Therapy*, $3^{rd}$; London, Tayloy & Francis, 2006.

Buffers: Buffer solutions are commonly used to maintain correct pH levels for biological and chemical systems. Many of the exemplary embodiments disclosed herein include using a buffer solution. Representative buffering agents or salts that may be present in the buffer include, but are not limited to, Tris, Tricine, HEPES, MOPS, TAPS, Bicine, TAPSO, TES, PIPES, Cacodylate, SSC, MES, KCl, NaCl, potassium acetate, $NH_4$-acetate, potassium glutamate, $NH_4Cl$, ammonium sulphate, $MgCl_2$, magnesium acetate and the like. One preferred buffer solution is phosphate buffered saline (PBS). Another preferred buffer solution is biotin ligase reaction buffer (0.1 M KCl, 5.5 mM $MgCl_2$, 50 mM Tris-HCl (pH=8.0), 0.05% Brij-35, 0.1 mM dithiothreitol (DTT), 3 mM ATP, and 60 µM biotin). The amount of buffering agent will typically range from about 5 to 150 mM, usually from about 10 to 100 mM, and more usually from about 20 to 50 mM, where in certain preferred embodiments the buffering agent will be present in an amount sufficient to provide a pH ranging from about 6.0 to about 9.5, more typically a pH range of from about 6.5 to about 7.4 at room temperature. Other agents that may be present in the buffer medium include chelating agents, such as EDTA, EGTA and the like.

Chemotherapeutic agent: Any chemical agent with therapeutic usefulness in the treatment of diseases characterized by abnormal cell growth. For example, chemotherapeutic agents are useful for the treatment of cancer, including breast cancer. In one embodiment, a chemotherapeutic agent is a radioactive compound. Another example includes tyrosine kinase inhibitors, such as lapatinib. In particular examples, such chemotherapeutic agents are administered in combination with a treatment that decreases or reduces homo- or heterodimerization of HER proteins (for example before, during or after administration of a therapeutically effective amount of one or more antibodies that specifically bind to HER2 or conjugate thereof). One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy*, Ch. 17 in Abeloff, Clinical Oncology $2^{nd}$ ed., © 2000 Churchill Livingstone, Inc; Baltzer, L., Berkery, R. (eds): *Oncology Pocket Guide to Chemotherapy*, 2nd ed. St. Louis, Mosby-Year Book, 1995; Fischer, D. S., Knobf, M. F., Durivage, H. J. (eds): *The Cancer Chemotherapy Handbook*, 4th ed. St. Louis, Mosby-Year Book, 1993; Chabner and Longo, *Cancer Chemotherapy and Biotherapy: Principles and Practice* (4th ed.). Philadelphia: Lippincott Williams & Wilkins, 2005; Skeel, *Handbook of Cancer Chemotherapy* (6th ed.). Lippincott Williams & Wilkins, 2003). Combination chemotherapy is the administration of more than one agent to treat cancer.

Chromogenic Staining: Chromogenic substrates have been used widely for immunohistochemistry for many years and for in situ hybridization more recently. Chromogenic detection offers a simple and cost-effective detection method. Chromogenic substrates have traditionally functioned by precipitating when acted on by the appropriate enzyme. That is, the traditional chromogenic substance is converted from a soluble reagent into an insoluble, colored precipitate upon contacting the enzyme. The resulting colored precipitate requires no special equipment for processing or visualizing. There are several qualities that successful IHC or ISH chromogenic substrates share. First, the substance should precipitate to a colored substance, preferably with a very high molar absorptivity. The enzyme substrate should have high solubility and reagent stability, but the precipitated chromogen products should be very insoluble, preferably in both aqueous and alcohol solutions. Enzyme turnover rates should be very high so as to highly amplify the signal from a single enzyme in a short amount of time. Until now, a relatively small number of chromogenic substances have been identified that legitimately possess all of these qualities. Reference is made to U.S. Provisional Patent Applications Nos. 61/616,330 and 61/710,607, which are hereby incorporated herein by reference in their entirety for disclosure related to chromogenic staining.

Conjugate: Two or more molecules coupled together, for example, by a covalent bond or non-covalent interaction. The two components comprising the conjugate can be directly coupled or indirectly coupled using a linker. In one example, a conjugate comprises a specific binding moiety linked to a biotinylating enzyme, such as an antibody coupled to biotin ligase. Another example of a conjugate is a specific binding moiety coupled to a biotin ligase substrate, such as an antibody linked to BTS either directly or indirectly by a linker.

Conjugate(ing), join(ing), bond(ing) or link(ing): Coupling a first molecule to a second molecule. This includes, but is not limited to, covalently bonding one molecule to another molecule, non-covalently bonding one molecule to another (e.g., electrostatically bonding) (see, for example, U.S. Pat. No. 6,921,496), hydrogen bonding, van der Waals forces, and any and all combinations of such couplings.

Contacting: Placement in direct association, for example solid, liquid or gaseous forms.

Control: A sample or standard used for comparison with a test sample, such as a biological sample, e.g., a biological sample obtained from a patient (or plurality of patients) or a cell culture. In some embodiments, a cell culture that is not incubated with a test agent serves as a control for a cell culture that is incubated with a test agent. In some embodiments, the control is a sample obtained from a healthy patient (or plurality of patients) (also referred to herein as a "normal" control), such as a normal breast sample. In some embodiments, the control is a historical control or standard value (i.e. a previously tested control sample or group of samples that represent baseline or normal values). In some embodiments the control is a standard value representing the average value (or average range of values) obtained from a plurality of patient samples.

Coupled: Two or more molecules joined together, either directly or indirectly. A first atom or molecule can be directly coupled or indirectly coupled to a second atom or molecule. A secondary antibody is indirectly coupled to an antigen when it is bound to a primary antibody that is bound to the antigen.

Decrease or Reduce: To reduce the quality, amount, or strength of something; for example a reduction in a protein-protein interaction. In one example, an agent reduces homo- or hetero-dimerization of HER proteins in a biological sample (e.g. a biological sample obtained from a subject or cell culture) as compared to the homo- or hetero-dimerization of HER proteins in the absence of the agent. In a particular example, the agent decreases homo- or hetero-dimerization of HER proteins, such as a decrease of at least 10%, at least 20%, at least 30%, at least 40%, at least 50%, at least 60%, at least 70%, at least 80%, or at least 90%. Such decreases can be measured using the methods disclosed herein.

Detecting: To identify the existence, occurrence, presence, or fact of something. General methods of detecting are known to a person of ordinary skill in the art and may be supplemented with the protocols and reagents disclosed herein. For example, included herein are methods of detecting a first target proximal to a second target in a biological sample.

Diagnosis: The process of identifying a disease by its signs, symptoms and/or results of various tests. The conclusion reached through that process is also called "a diagnosis." Forms of testing commonly performed include blood tests, medical imaging, genetic analysis, urinalysis, biopsy and analysis of biological samples obtained from a subject.

Diagnostically significant amount: An increase or decrease of a measurable characteristic that is sufficient to allow one to distinguish one patient population from another (such as distinguishing a subject having a breast carcinoma with high expression of HER2 homo-dimers from a subject having a breast carcinoma with low or no expression of HER2 homo-dimers). The methods of detecting a first target proximal to a second target provided herein are one example of how hetero- and homo-dimerization of HER proteins can be detected.

Effective amount: The amount of an agent (such as a HER2 specific antibody or a conjugate including a HER2 specific antibody) that alone, or together with one or more additional agents, induces the desired response, such as formation of a detectable immune complex with HER2 or a decrease in HER2 homodimerization in a biological sample.

FFPE: Formalin fixed paraffin embedded sample.

Hapten: A hapten is a molecule, typically a small molecule that can combine specifically with an antibody, but typically is substantially incapable of being immunogenic except in combination with a carrier molecule. Many haptens are known and frequently used for analytical procedures, such as dinitrophenyl, biotin, digoxigenin, fluorescein, rhodamine, or combinations thereof. Other haptens have been specifically developed by Ventana Medical Systems, Inc., assignee of the present application, including haptens selected from oxazoles, pyrazoles, thiazoles, nitroaryls, benzofurans, triterpenes, ureas, thioureas, rotenoids, coumarins, cyclolignans, and combinations thereof, with particular hapten examples of haptens including benzofurazan, nitrophenyl, 4-(2-hydroxyphenyl)-1H-benzo[b] [1,4]diazepine-2(3H)-one, and 3-hydroxy-2-quinoxalinecarbamide. Plural different haptens may be coupled to a polymeric carrier. Moreover, compounds, such as haptens, can be coupled to another molecule using a linker, such as an NHS-PEG linker.

Human epidermal growth factor receptor (HER): A family of structurally related proteins, including at least HER1, HER2, HER3 and HER4 (a.k.a. EGFR1, EGFR2, EGFR3 and EGFR4, respectively, or ErbB-1, ErbB-2, ErbB-3 and ErbB-4, respectively). HER1, HER2 and HER4 are receptor tyrosine kinases; although HER3 shares homology with HER1, HER2 and HER4, HER3 is kinase inactive. Included in the HER family is p95, a truncated form of HER2 lacking portions of the HER2 extracellular domain (see, e.g., Arribas et al, *Cancer Res.*, 71:1515-1519, 2011; Molina et al, *Cancer Res.*, 61:4744-4749, 2001). "HER protein" or "a HER protein" refers to the family of HER proteins, including at least HER1, HER2, HER3, HER4 and p95.

HER proteins mediate cell growth and are disregulated in many types of cancer. For example HER1 and HER2 are upregulated in many human cancers, and their excessive signaling may be critical factors in the development and malignancy of these tumors. Receptor dimerization is essential for HER pathway activation leading to receptor phosphorylation and downstream signal transduction. Unlike HER1, -3 and -4, HER2 has no known ligand and assumes an open conformation, with its dimerization domain exposed for interaction with other ligand-activated HER receptors. (See, e.g., Herbst, *Int J. Radiat. Oncol. Biol. Phys.*, 59:21-6, 2004; Zhang et al, *J. Clin. Invest.* 117 (8): 2051-8, 2007.)

Approximately 30% of breast cancers have an amplification of the HER2 gene or overexpression of its protein product. HER2 overexpression also occurs in other cancer types, such as ovarian cancer, stomach cancer, and biologically aggressive forms of uterine cancer, such as uterine serous endometrial carcinoma. See, e.g., Santin et al, *Int J. Gynaecol. Obstet*, 102 (2): 128-31, 2008. HER2-containing homo- and hetero-dimers are transformation competent protein complexes. Trastuzumab, a humanized antibody that prevents HER2 homodimerization is used to treat certain HER2 overexpressing cancers, including breast cancer. Additionally, the level of HER2 expression in cancer tissue is predictive of patient response to HER2 therapeutic antibodies (e.g., Trastuzumab). Because of its prognostic role as well as its ability to predict response to Trastuzumab, tumors (e.g., tumors associated with breast cancer) are routinely checked for overexpression of HER2.

The HER pathway is also involved in ovarian cancer pathogenesis. Many ovarian tumor samples express all HER proteins. Co-expression of HER1 and HER2 is seen more frequently in ovarian cancer than in normal ovarian epithelium, and overexpression of both receptors correlates with poor prognosis. Preferred dimerization with HER2 (HER1/HER2, HER2/HER3) and subsequent pathway activation via receptor phosphorylation have also been shown to drive ovarian tumor cell proliferation, even in the absence of HER2 overexpression. pertuzumab, a humanized antibody that prevents HER2 dimerization (with itself and with HER3) has been shown to provide therapeutic benefit to patients with HER2 and/or HER3 expressing ovarian cancer.

Examples of HER1 amino acid sequence include NCBI/Genbank accession Nos. NP_005219, CAA25240, AAT52212, AAZ66620, BAF83041, BAH11869, ADZ75461, ADL28125, BAD92679, AAH94761, all of which are incorporated by reference herein as provided in Genbank on Oct. 27, 2011. Examples of, HER2, amino acid sequences include NCBI/Genbank accession BAJ17684, P04626, AAI67147, NP_001005862, NP_004439, AAA75493, AAO18082, all of which are incorporated by reference herein as provided in Genbank on Oct. 27, 2011. Examples of HER3 amino acid sequences include NCBI/Genbank accession Nos. NP_001973, P21860, AAH82992, AAH02706, AAA35979, all of which are incorporated by reference herein as provided in Genbank on Oct. 27, 2011. Examples of HER4 amino acid sequences include NCBI/Genbank accession Nos., AAI43750, Q15303, NP_005226, NP_001036064, AAI43748, all of which are incorporated by reference herein as provided in Genbank on Oct. 27, 2011.

Immune complex: The binding of antibody to a soluble antigen forms an immune complex. The formation of an immune complex can be detected through conventional methods known to the person of ordinary skill in the art, for instance immunohistochemistry, immunoprecipitation, flow cytometry, immunofluorescence microscopy, ELISA, immunoblotting (i.e., Western blot), magnetic resonance imaging, CT scans, X-ray and affinity chromatography. Immunological binding properties of selected antibodies may be quantified using methods well known in the art.

Linker: The two components of a conjugate are joined together either directly through a bond or indirectly through a linker. Typically, linkers are bifunctional, i.e., the linker includes a functional group at each end, wherein the functional groups are used to couple the linker to the two conjugate components, either covalently or non-covalently. The two functional groups may be the same, i.e., a homobifunctional linker, or different, i.e., a heterobifunctional linker, but more typically are heterobifunctional. Where linkers are employed, suitable functional groups are selected to allow attachment of the two components of the conjugate, while not impairing the functionality of the components. Linkers of interest may vary widely depending on the components in the conjugate. In many embodiments the linker, when present, is biologically inert.

Neoplasia, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant."

Tumors of the same tissue type are primary tumors originating in a particular organ (such as colon, skin, breast, prostate, bladder or lung). Tumors of the same tissue type may be divided into tumors of different sub-types. For example, lung carcinomas can be divided into an adenocarcinoma, small cell, squamous cell, or non-small cell tumors.

Examples of solid tumors, such as sarcomas (connective tissue cancer) and carcinomas (epithelial cell cancer), include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colorectal carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma).

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. It will be understood that when a nucleotide sequence is represented by a DNA sequence (i.e., A, T, G, C), this also includes an RNA sequence (i.e., A, U, G, C) in which "U" replaces "T."

Nucleotide: Term includes, but is not limited to, a base linked to a sugar, such as a pyrimidine, purine or synthetic analogs thereof, or a base linked to an amino acid, as in a peptide nucleic acid (PNA). A nucleotide is one unit in a polynucleotide. A nucleotide sequence refers to the sequence of bases in a polynucleotide.

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

Nucleic Acid Probe: A short sequence of nucleotides, such as at least 8, at least 10, at least 15, at least 20, at least 25, or at least 30 nucleotides in length, used to detect the presence of a complementary sequence by molecular hybridization. In particular examples, probes include a label that permits detection of probe:target sequence hybridization complexes. Typical labels include radioactive isotopes, enzyme substrates, co-factors, ligands, chemiluminescent or fluorescent agents, haptens, and enzymes. These labels may be directly attached to the probe or attached via a linker. Methods for labeling and guidance in the choice of labels appropriate for various purposes are discussed, for example, in Sambrook et al, Molecular Cloning: A Laboratory Manual, Cold Spring Harbor Laboratory Press (1989) and Ausubel et al., Current Protocols in Molecular Biology, Greene Publishing Associates and Wiley-Intersciences (1987). Methods suitable for attaching a linker to nucleic acid probe are well known to those of ordinary skill in the art. See, for example, U.S. Pat. No. 5,733,523, and Hermanson, "Bioconjugate Techniques," Academic Press, San Diego, 1996.

Probes are generally at least 10 nucleotides in length, such as at least 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 51, 52, 53, 54, 55, 56, 57, 58, 59, 60, or more contiguous nucleotides complementary to the target nucleic acid molecule, such as 10-60 nucleotides, 30-60 nucleotides, 20-50 nucleotides, 30-50 nucleotides, 20-40 nucleotides, or 10-40 nucleotides. Probes can also be of a maximum length, for example no more than 15, 25, 40, 50, 75 or 100 nucleotides in length. One of ordinary skill in the art will appreciate that the specificity of a particular probe increases with its length.

Oligonucleotide: A linear polynucleotide sequence of between 5 and 100 nucleotide bases in length.

Proximal: Refers to the qualitative or quantitative distance between two molecules; for example, the distance between two proteins in a tissue sample. In some embodiments, molecules that are proximal to each other are within at least about 100 nm, at least about 75 nm, at least about 50 nm, at least about 35 nm, at least about 30 nm, at least about 25 nm, at least about 20 nm, at least about 15 nm, at least about 10 nm, at least about 5 nm or less distance of each other. Proximal may also provide a functional relationship. For examples, two targets (e.g., two proteins) may be considered proximal if the first target is within sufficient distance of the second target for a biotin ligase associated with the first target to allow biotinylation of a substrate associated with a second target. Another functional definition of proximal is the dimerization of two proteins. Another functional definition of proximal is associated to a genetic translocation. Two portions of the genome may be considered proximal when they are adjacent to each other or within 500,000 bp, within 100,000 bp, within 50,000 bp within 25,000 bp, within 10,000 bp, or within 1,000 bp of each other. This contrast to two portions which are not proximal due to a translocation (either a move to another chromosome or an inversion).

Sample: Certain disclosed embodiments utilize biological samples. A biological sample is typically obtained from a mammalian subject of interest, such as a human. The sample can be any sample, including, but not limited to, tissue from biopsies, autopsies and pathology specimens. Biological samples also include sections of tissues, for example, frozen sections taken for histological purposes. Biological samples also include cell cultures or portions of cell cultures, for example, a cell culture grown from a biological sample taken from a subject.

Biological samples can be obtained from a subject using any method known in the art. For example, tissue samples can be obtained from breast cancer patients who have undergone tumor resection as a form of treatment. From these patients, both tumor tissue and surrounding non-cancerous tissue can be obtained. In some embodiments, the non-cancerous tissue sample used as a control is obtained from a cadaver. In some embodiments, biological samples are obtained by biopsy. Biopsy samples can be fresh, frozen or fixed, such as formalin-fixed and paraffin embedded. Samples can be removed from a patient surgically, by extraction (for example by hypodermic or other types of needles), by micro-dissection, by laser capture, or by any other means known in the art.

In some embodiments, the biological sample is a tissue sample, e.g., a tissue sample obtained from a subject diagnosed with a tumor, such as a malignant or benign breast cancer tumor. In some cases, the tissue samples are obtained from healthy subjects or cadaveric donors. A "sample" refers to part of a tissue that is either the entire tissue, or a diseased or healthy portion of the tissue. In some embodiments, malignant tumor tissue samples are compared to a control. In some embodiments, the control is a benign tumor tissue sample obtained from a different subject. In some embodiments, the control is non-cancerous tissue sample obtained from the same subject, such as a benign tumor adjacent to the tumor. In other embodiments, the control is non-cancerous tissue sample obtained from the same subject, such as non-cancerous tissue surrounding the malignant tumor. In other embodiments, the control is non-cancerous tissue sample from a cadaver. In other embodiments, the control is a reference sample, such as standard or reference value based on an average of historical values.

In some embodiments, the biological sample is obtained from a subject that has, is suspected of having, or is at risk of developing, a tumor, e.g., a carcinoma. For example, the subject has, is suspected of having, or is at risk of developing breast, ovarian, uterine or stomach cancer.

Sensitivity and specificity: Statistical measurements of the performance of a binary classification test. Sensitivity measures the proportion of actual positives which are correctly identified (e.g., the percentage of samples that are identified as including nucleic acid from a particular virus). Specificity measures the proportion of negatives which are correctly identified (e.g., the percentage of samples that are identified as not including a target nucleic acid, such as a nucleic acid from a particular virus or bacteria).

Sequence identity: The similarity between two nucleic acid sequences is expressed in terms of the similarity between the sequences, otherwise referred to as sequence identity. Sequence identity is frequently measured in terms of percentage identity, similarity, or homology; a higher percentage identity indicates a higher degree of sequence similarity.

The NCBI Basic Local Alignment Search Tool (BLAST), Altschul et al, J. Mol. Biol. 215:403-10, 1990, is available from several sources, including the National Center for Biotechnology Information (NCBI, Bethesda, Md.), for use in connection with the sequence analysis programs blastp, blastn, blastx, tblastn and tblastx. It can be accessed through the NCBI website. A description of how to determine sequence identity using this program is also available on the website.

When less than the entire sequence is being compared for sequence identity, homologs will typically possess at least 75% sequence identity over short windows of 10-20 amino acids, and can possess sequence identities of at least 85% or at least 90% or 95% depending on their similarity to the reference sequence. Methods for determining sequence identity over such short windows are described, for example on the NCBI website.

These sequence identity ranges are provided for guidance only; it is entirely possible that strongly significant homologs could be obtained that fall outside of the ranges provided.

An alternative indication that two nucleic acid molecules are closely related is that the two molecules hybridize to each other under stringent conditions. Stringent conditions are sequence-dependent and are different under different environmental parameters. Generally, stringent conditions are selected to be about 5° C. to 20° C. lower than the thermal melting point (Tm) for the specific sequence at a defined ionic strength and pH. The Tm is the temperature (under defined ionic strength and pH) at which 50% of the target sequence hybridizes to a perfectly matched probe. Conditions for nucleic acid hybridization and calculation of stringencies can be found in Sambrook et al; and Tijssen, *Hybridization With Nucleic Acid Probes, Part I: Theory and Nucleic Acid Preparation*, Laboratory Techniques in Biochemistry and Molecular Biology, Elsevier Science Ltd., 1993.

Specific binding moiety(ies): A member of a specific-binding pair. Specific binding pairs are pairs of molecules that are characterized in that they bind each other to the substantial exclusion of binding to other molecules (for example, specific binding pairs can have a binding constant that is at least $10^{-3}$ greater, $10^{-4}$ greater or $10^{-5}$ greater than a binding constant for either of the two members of the binding pair with other molecules in a biological sample). The specific binding moiety used to make the exemplary conjugates disclosed herein may be any of a variety of different types of molecules, so long as it exhibits the requisite binding affinity for the target.

The specific binding moiety may comprise a small molecule or large molecule. A small molecule will range in size from about 50 to about 10,000 daltons, more typically from about 50 to about 5,000 daltons, and even more typically from about 100 to about 1000 daltons. A large molecule is one whose molecular weight is typically greater than about 10,000 daltons. The small molecule may be any molecule, typically an organic molecule that is capable of binding with the requisite affinity to the target. The small molecule typically includes one or more functional groups allowing it to interact with the target, for example by hydrophobic, hydrophilic, electrostatic or covalent interactions. Where the target is a protein, lipid or nucleic acid, the small molecule typically will include functional groups allowing for structural interactions such as hydrogen bonding, hydrophobic-hydrophobic interactions, electrostatic interactions, etc. The small molecule ligand often includes an amine, amide, sulfhydryl, carbonyl, hydroxyl or carboxyl group, and preferably at least two of these functional groups.

The small molecules often comprise cyclic and/or heterocyclic non-aromatic structures, and/or aromatic or polyaromatic structures substituted with one or more of the above functional groups. Also useful small molecules include structures found among biomolecules, including peptides, saccharides, fatty acids, steroids, purines, pyrimidines, derivatives, structural analogs or combinations thereof.

The small molecule may be derived from a naturally occurring or synthetic compound that may be obtained from a wide variety of sources, including libraries of synthetic or natural compounds. For example, numerous methods are available for random and directed synthesis of a wide variety of organic compounds and biomolecules, including the preparation of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known small molecules may be subjected to directed or random chemical modifications, such as acylation, alkylation, esterification, amidification, etc., to produce structural analogs.

As such, the small molecule may be obtained from a library of naturally occurring or synthetic molecules, including a library of compounds produced through combinatorial means, i.e. a compound diversity combinatorial library. When obtained from such libraries, the small molecule employed will have demonstrated some desirable affinity for a target in a convenient binding affinity assay. Combinatorial libraries, as well as methods for their production and screening, are known in the art and are described in U.S. Pat. Nos. 5,741,713 and 5,734,018, the disclosures of which are incorporated herein by reference. Additional information concerning specific binding moieties is provided by assignee's U.S. Pat. No. 7,695,929, which also is incorporated herein by reference. The specific binding moiety may comprise a large molecule. Of particular interest as large molecule specific binding moieties are antibodies, as well as binding fragments and derivatives or mimetics thereof. As such, the specific binding moiety may be either a monoclonal or polyclonal antibody. Also of interest are antibody fragments or derivatives produced either recombinantly or synthetically, such as single chain antibodies or scFvs, or other antibody derivatives such as chimeric antibodies or CDR-grafted antibodies, where such recombinantly or synthetically produced antibody fragments retain the binding characteristics of the above antibodies. Such antibody fragments, derivatives or mimetics of the subject invention may be readily prepared using any convenient methodology, such as the methodology disclosed in U.S. Pat. Nos. 5,851,829 and 5,965,371, the disclosures of which are incorporated herein by reference.

Also suitable for use as large molecule specific binding moieties are polynucleic acid aptamers. Polynucleic acid aptamers may be RNA oligonucleotides that selectively bind proteins, much in the same manner as a receptor or antibody (Conrad et al., Methods Enzymol. (1996), 267(Combinatorial Chemistry), 336-367), or DNA oligomers that complement specific DNA target sequences.

In addition to antibody-based peptide/polypeptide or protein-based binding domains, the specific binding moiety may also be a lectin, a soluble cell-surface receptor or derivative thereof, an affibody or any combinatorially derived protein or peptide from phage display or ribosome display or any type of combinatorial peptide or protein library. Combinations of any specific binding moiety may be used.

Importantly, the specific binding moiety will be one that allows for coupling to the second component of the conjugate, or to a linker, without substantially affecting the binding affinity of the specific binding moiety to its target.

Particular examples of specific binding moieties include specific binding proteins (for example, antibodies, lectins, avidins such as streptavidins, and protein A). Specific binding moiety(ies) also includes the molecules (or portions thereof) that are specifically bound by such specific binding proteins.

Subject: Any mammal, such as humans, non-human primates, pigs, sheep, cows, rodents and the like. Thus, the term "subject" includes both human and veterinary subjects. In one example, a subject is one known or suspected of having a HER+ tumor. In another example, a subject is one who is being considered for treatment with an antibody that is specific for HER, such as pertuzumab or Trastuzumab.

Target: Any molecule for which the presence, location and/or concentration is or can be determined. Examples of target molecules include proteins and haptens, such as haptens covalently bonded to proteins. Target molecules are typically detected using one or more conjugates of a specific binding molecule and a detectable label. Examples of specific targets include proteins, carbohydrates, or nucleic acid molecules. Exemplary protein targets include p95, HER1, HER2, HER3 or HER4. Target nucleic acid molecules include those molecules whose proximity, rearrangement, amplification, deletion, detection, quantitation, qualitative detection, or a combination thereof, is sought. For example, the target can be a defined region or particular portion of a nucleic acid molecule, for example a portion of a genome (such as a gene or a region of DNA or RNA containing a gene (or portion thereof) of interest). The nucleic acid molecule need not be in a purified form. Various other nucleic acid molecules can also be present with the target nucleic acid molecule. For example, the target nucleic acid molecule can be a specific nucleic acid molecule (which can include RNA or DNA), the amplification of at least a portion thereof (such as a portion of a genomic sequence or cDNA sequence) is intended. In some examples, a target nucleic acid includes a viral nucleic acid molecule, or a bacterial nucleic acid molecule, such as a nucleic acid molecule from *Escherichia coli* or *Vibrio cholera*. Purification or isolation of the target nucleic acid molecule, if needed, can be conducted by methods known to those in the art, such as by using a commercially available purification kit or the like.

Treating or Treatment: A therapeutic intervention (e.g., administration of a therapeutically effective amount of an antibody that specifically binds HER2 or a conjugate thereof) that ameliorates a sign or symptom of a disease or pathological condition related to a disease (such as a tumor). Treatment can also induce remission or cure of a condition, such as cancer. In particular examples, treatment includes preventing a tumor, for example by inhibiting the full development of a tumor, such as preventing development of a metastasis or the development of a primary tumor. Prevention does not require a total absence of a tumor.

Reducing a sign or symptom associated with a tumor can be evidenced, for example, by a delayed onset of clinical symptoms of the disease in a susceptible subject (such as a subject having a tumor which has not yet metastasized), a reduction in severity of some or all clinical symptoms of the disease, a slower progression of the disease (for example by prolonging the life of a subject having tumor), a reduction in the number of relapses of the disease, an improvement in the overall health or well-being of the subject, or by other parameters well known in the art that are specific to the particular tumor.

Tumor burden: The total volume, number, metastasis, or combinations thereof of tumor or tumors in a subject.

Tyramide Signal Amplification (TSA): An enzyme-mediated detection method that utilizes the catalytic activity of a peroxidase (such as horseradish peroxidase) to generate high-density labeling of a target molecule (such as a protein or nucleic acid sequence) in situ. TSA typically involves three basic steps: (1) binding of a specific binding member (e.g., an antibody) to the target followed by secondary detection of the specific binding member with a second peroxidase-labeled specific binding member; (2) activation of multiple copies of a labeled tyramide derivative (e.g., a hapten-labeled tyramide) by the peroxidase; and (3) covalent coupling of the resulting highly reactive tyramide radicals to residues (e.g., the phenol moiety of protein tyrosine residues) proximal to the peroxidase-target interaction site, resulting in deposition of haptens proximally (diffusion and reactivity mediated) to the target. In some examples of TSA, more or fewer steps are involved; for example, the TSA method can be repeated sequentially to increase signal. Methods of performing TSA and commercial kits and reagents for performing TSA are available (see, e.g., Amp-Map Detection Kit with TSA™, Cat. No. 760-121, Ventana Medical Systems, Tucson, Ariz.; Invitrogen; TSA kit No. T-20911, Invitrogen Corp, Carlsbad, Calif.). In some embodiments, TSA is a component of the provided PTDM. Other enzyme-catalyzed, hapten or signaling linked reactive species can be alternatively used as they may become available.

Under conditions sufficient for: A phrase that is used to describe any environment that permits a desired activity. In one example the desired activity is formation of an immune complex. In another example, the desired activity is peroxidase-catalyzed formation of a covalent bond between a tyramide and a phenol moiety, for example catalysis that occurs in the presence of hydrogen peroxide.

3' end: The end of a nucleic acid molecule that does not have a nucleotide bound to it 3' of the terminal residue.

5' end: The end of a nucleic acid sequence where the 5' position of the terminal residue is not bound by a nucleotide.

II. General Description of Method

Certain disclosed embodiments concern detecting at least a first target, and typically two separately identifiable targets that are located sufficiently near, or proximal to, each other. The method is useful, for example, for detecting the presence or absence of proximal proteins or nucleic acids in a biological sample. A person of ordinary skill in the art will recognize that other biological targets, including combinations of nucleic acid targets, carbohydrate targets, and protein targets, can be detected using the disclosed detection methodology. In one embodiment, the method detects the presence or absence of hetero- and homo-dimerization of HER proteins in a biological sample, particularly FFPE samples, such as a cancer biopsy. Additionally disclosed are conjugates and kits for use with the method, and diagnostic and screening methods that utilize the provided proximal target detection method.

In several embodiments, a proximal target detection method uses a combination of novel reagents to selectively bind to proximal targets in a biological sample. Briefly, a first target of interest is labeled with a biotin ligase and a second target is labeled with a peptide substrate for the biotin ligase. The method may include determining the proximity of a first target and a second target in a biological sample. In some embodiments, the first target is a protein and the second target is a protein. In some embodiments, the first target is p95, HER1, HER2, HER3 or HER4 and the second target is p95, HER1, HER2, HER3 or HER4.

In some embodiments, the method determines that the first target is near to, or proximal to, the second target. For example, the first target may be within less than about 100 nm of the second target in the biological sample, such as within 75 nm, within 50 nm within 35 nm, within 25 nm, within 10 nm or within 5 nm of the second target, such as between 1 nm and 50 nm, 5 nm and 50 nm, or 5 nm and 25 nm, of the second target.

FIG. 1 is a schematic illustration of one disclosed embodiment for in situ proximity detection of a first target A and a second target B using a biotin ligase (e.g. from BirA) associated with a target A to biotinylate a peptide substrate, referred to generally herein as BTS, associated with target B. The BTS-biotin product can be subsequently detected as desired, such as by using Streptavidin-HRP or Streptavidin-AP, with or without signal amplification. Certain working embodiments of the method utilized biotin ligase, an enzyme from *E. coli*, and an 18 amino-acid long peptide substrate for sensitive and specific detection of protein-protein interactions in FFPE tissue. Biotin ligase can efficiently biotinylate BTS in the presence of biotin, but the reaction can only occur when the enzyme makes physical contact with BTS, as depicted in FIG. 1. Accordingly, in certain embodiments biotin ligase and BTS were conjugated separately to two antibodies that recognize targets of interest (A and B) respectively. When targets of interest are in close proximity, e.g. receptor dimerization on cell membrane that triggers a signaling relay, binding of specific binding moiety conjugates to their respective targets brings biotin ligase and BTS in close proximity, leading to biotinylation. Subsequently, the biotinylated product is detected.

Targets do not have to be proteins that are recognized by antibodies. Instead, any biomolecule e.g. lipid and nucleic acid, when modified and recognized by any affinity 'binder,' can be used for the disclosed proximity detection method. This approach provides a sensitive method for detecting proximal targets with roles in maladies such as cancer biology, thereby providing novel insights and diagnostic tests to empower clinicians to treat patients.

III. Conjugate Probes for Detection of Proximal Targets

For certain embodiments, a first conjugate is designed to detect a first target A, and a second conjugate is used to detect a second target B. The first conjugate comprises a specific binding moiety and an enzyme that attaches, typically covalently, a probe to a substrate molecule. The second conjugate comprises a specific binding moiety and a substrate for the enzyme. Examples of suitable enzymes, substrates and cofactors include: Biotin Ligase, using AP/Avi-Tag/BTS as a substrate, and biotin and ATP as cofactors; O6-alkylguanine-DNA-alkyltransferase, using a SNAP-tag substrate and O6-benzylguanine as a cofactor; and 4'-phosphopantetheinyl transferase, using ACP-tag as a substrate and CoA as a cofactor.

The method is illustrated herein with reference to biotin ligase and biotin ligase substrates. Accordingly, the biotin ligase conjugate probe comprises a specific binding moiety and an enzyme that biotinylates a substrate. For exemplary working embodiments, biotin ligase was covalently conjugated to a primary or secondary antibody selected for a particular target. A second probe, a biotin ligase substrate probe, specific for a target B that is located proximal to, or is a dimer or is otherwise spatially associated with target A, comprises a conjugate between a biotinylation substrate and a second specific binding moiety specific for associating, either directly or indirectly, with the second target B.

A. Biotin Ligase Conjugate Probes

Any enzyme capable of biotinylating a substrate can be used to form suitable biotin ligase probes according to disclosed embodiments of the present invention. Truncated protein forms also can be used, as long as the truncated protein retains enzymatic activity. For example, truncated forms of the protein lacking the DNA binding domain at the amino terminus retain biotin ligase activity and can be used. It currently is believed that at least 60 amino acids can be removed from biotin ligase from BirA and still retain enzymatic activity. Enzymatic biotinylation allows biotin to be linked, typically covalently at a particular residue, to a protein substrate to produce a biotinylated product detectable by streptavidin.

1. Biotin Ligase from *E. coli*

For certain disclosed embodiments, biotin ligase (from BirA) has been used to biotinylate an appropriate substrate in the presence of biotin and ATP. Biotin-[acetyl-CoA-carboxylase] ligase (EC 6.3.4.15) catalyzes the following reaction:

ATP+biotin+apo-[acetyl-CoA:carbon-dioxide ligase (ADP-forming)]⇌AMP+diphosphate+[acetyl-CoA:carbon-dioxide ligase (ADP-forming)

The systematic name of one exemplary class of enzymes useful for practicing disclosed embodiments is biotin:apo-[acetyl-CoA:carbon-dioxide ligase (ADP-forming)] ligase (AMP-forming). Other common names include biotin-[acetyl-CoA carboxylase] synthetase, biotin-[acetyl coenzyme A carboxylase] synthetase, acetyl coenzyme A holocarboxylase synthetase, acetyl CoA holocarboxylase synthetase, biotin:apocarboxylase ligase, biotin holoenzyme synthetase, and HCS.

Biotin ligase is available from various sources. Biotin ligase from *E. Coli* has been used for certain working embodiments. While this application proceeds substantially with reference to using biotin ligase from *E. coli*, a person of ordinary skill in the art will appreciate that biotin ligase from any source can be used. For certain embodiments, the Bir A gene from *E. coli* was amplified by PCR with DNA templates from plasmid pBIOTIN LIGASEcm (note any *E. coli* genomic DNA will serve the same purpose because biotin ligase is an essential gene). The 5' primer sequence is provided below as SEQ. ID No. 1:

SEQ. ID No. 1
CATATGGGAAGCGGCCATCACCACCACCATCACGGAGGCGGAGGTTCAG

GCTGCAGCAACCTGTCTACCTGTGTGTTGAAGGATAACACCGTGCCAC

This sequence include a poly-histidine tag, followed by a disulfide bridge (CSNLSTCVL) from salmon calcitonin. The poly-histidine tag facilitates purification by metal affinity purification and the disulfide bridge was used for chemical conjugation to antibodies. The 3' primer sequence is provided below as SEQ. ID No. 2:

SEQ. ID No. 2
GCTGTCGACTTATTTTTCTGCACTACGCAGGGATA

Biotin ligase gene from *E. coli* was used to produce biotin ligase according to the method of Example 1 below. Biotin ligase was purified on Ni-NTA column to yield about 25 milligrams from 1 liter culture. The fusion protein sequence for certain working embodiments is provided below as SEQ. ID No. 3:

SEQ. ID No. 3
MGSGHHHHHHGGGGSGCSNLSTCVLKDNTVPLKLIALLANGEFHSGEQLG

ETLGMSRAAINKHIQTLRDWGVDVFTVPGKGYSLPEPIQLLNAKQILGQL

DGGSVAVLPVIDSTNQYLLDRIGELKSGDACIAEYQQAGRGRRGRKWFSP

FGANLYLSMFWRLEQGPAAAIGLSLVIGIVMAEVLRKLGADKVRVKWPND

LYLQDRKLAGILVELTGKTGDAAQIVIGAGINMAMRRVEESVVNQGWITL

QEAGINLDRNTLAAMLIRELRAALELFEQEGLAPYLSRWEKLDNFINRPV

KLIIGDKEIFGISRGIDKQGALLLEQDGIIKPWMGGEISLRSAEK

A biotin ligase enzymatic assay was developed to assess the activity of purified protein and antibody conjugates as described in Example 2. The reaction product was analyzed and confirmed with MALDI-TOF by detecting the peptide substrate before and after biotinylation.

Additional examples of exemplary enzymes suitable for practicing the disclosed embodiments include those from *Thermococcus kodakarensis* KOD1, *Thermococcus zilligii* AN1, *Thermococcus gammatolerans* EJ3, *Pyrococcus abyssi* GE5, *Pyrococcus horikoshii* OT3, and *Clostridium botulinum* C str. The sequences of these additional examples of suitable enzymes are:

2. Biotin-protein ligase [*Thermococcus kodakarensis* KOD1]

SEQ. ID No. 4

MEWNVIRLDEVDSTNEYAKKLIPDVSEGTVVVAKRQTSGRGRKGRAWASPEGGLWMS

VILKPPMIDPRLVFVGALAVSDTLRDFGIGAWIKWPNDVWVGNRKISGVLTEVKGDFVIM

GVGLNVNNEIPDGLKETATSMMEALGEPVDIGEVLERLLEYLGRWYKTFLENPPLVVEE

VRGRTMLIGKEVRVLLDGNDLVGRVITISDDGSLILDVDGQTVKVVYGDVSVRINR

3. Biotin-protein ligase [*Thermococcus zilligii* AN1]

SEQ. ID No. 5

MWKIIHLDEVDSTNDYAKSIAEESPEGTVVIAKRQTAGKGRKGRSWASPEGGLWMSVIL

KPERTDPRLVFVGALAVVDTLADFGIKGWIKWPNDVWVEGKKIAGVLTEGKAEKFVVM

GIGLNVNNPVPEGLEREATSMIYHTGMELPLDSVLDRLLFHLGGWYGVYKERPELLVEK

LRQRTFILGKAVRVTEDDKTIIGRALDVLDDGSLLLEVGGELRRILYGDVSVRPL

4. Biotin-protein ligase [*Thermococcus gammatolerans* EJ3]

SEQ. ID No. 6

MEWNIITLDEVDSTNEYARRIAPTAPEGTVVVAKRQTAGRGRKGRRWASPEGGLWMT

VILKPKSGPEHVTKLVFVGALAVLDTLHEYGIRGELKWPNDVLVDGKKIAGILSECRLNHF

ALLGIGLNVNNEIPDELRESAVSMKEVLGRAIDLEEVLNRVLRNLSRWYGLFRNGRHGEI

LKAVKGSSAVLGKRVRIIEDGEIIAEGIAVDIDNSGALILKGEENTVRVLYGDVSLRFS

5. Biotin-protein ligase [*Pyrococcus abyssi* GE5]

SEQ. ID No. 7

MLGLKTSVIGRTIIYFQEVASTNDYAKAENLEEGTVIVADRQIKGHGRLERKWESPEGGL

WMSVVLTPRVSQEDLPKIVFLGALAVVETLREFSIDARIKWPNDVLVNYRKVAGVLVEAK

GEKVILGIGLNVNNKVPDGATSMKQELGSEIPMLNVFKTLVKTLDSLYLKFLESPGKILER

AKRSMILGVRVKVLSDGEVEAEGIAEDVDEFGRLIVRLDDGRVKKILYGDVSLRFL

6. Biotin-protein ligase [*Pyrococcus horikoshii* OT3]

SEQ. ID No. 8

MLGLKTSIIGRRVIYFQEITSTNEFAKTSYLEEGTVIVADKQTMGHGRLNRKWESPEGGL

WLSIVLSPKVPQKDLPKIVFLGAVGVVETLKEFSIDGRIKWPNDVLVNYKKIAGVLVEGKG

DKIVLGIGLNVNNKVPNGATSMKLELGSEVPLLSVFRSLITNLDRLYLNFLKNPMDILNLV

RDNMILGVRVKILGDGSFEGIAEDIDDFGRLIIRLDSGEVKKVIYGDVSLRFL

7. Biotin ligase bi-functional protein, putative
[*Clostridium botulinum* C str.]

SEQ. ID No. 9

MKEEIISLLKENKDNFISGEKISEKFGITRAAIWKYMKAIKNEGYKIESVSRKGYKLISSPDL

LTFQEINPYLTTNYIGKNIMYFNTIDSTNNKAKELGAKDILEGTVVISEEQTGGRGRLGRQ

WVSPKFKGIWMSIILRPNIEPMEAAKITQIAAAAVCSVIKELGIDVYIKWPNDIVLNNKKICG

ILTEMSGEINKINYIVLGIGINVNIDKEDFPEYIKDIATSIKIETGLNIQRKELIAKIFNKFEILYD

EFINEGTIKKSIEICKGNSALLGKEVKIIRKSTEVFAKALTIAEDGELIVEYDDGKVEKIVSG

EVSIRGMYGW

One embodiment of a method for making a suitable conjugate is illustrated schematically in FIG. 2. For example, a goat-anti-Rabbit:biotin ligase conjugate was made comprising a PEG linker having from about 2 to about 20 PEG units, more typically 2 to about 10 PEG units, and even more typically from 4 to 8 PEG units. Prior to reaction, the PEG linker had a maleimide functional group on one end and an NHS-ester on the other, thereby having a formula MAL-$PEG_8$-NHS. An antibody-linker conjugate was made by coupling the antibody to the linker through the NHS ester functionality. Biotin ligase-SS was reduced to form reactive sulfhydryl groups. The reduced biotin ligase enzyme was combined with the antibody-linker conjugate to form a goat-anti-Rabbit:biotin ligase conjugate by the reaction between the sulfhydryl group and the pendent maleimide group. The conjugate was purified on GE AKTA FPLC using Superdex 200 HR 10/30 gel. Protein was eluted using PBS (10 mM phosphate, pH=7.4). Additional details concerning this synthesis are provided in Example 3. This procedure typically resulted in coupling 1-3 biotin ligase:1 antibody.

Biotin ligase-anti-hapten antibody conjugates can be formed in a similar manner. A mouse anti-nitrophenyl:Bir A conjugate, for example, was formed in this manner using MAL-$PEG_8$-NHS. Conjugates with other IgGs were synthesized under the same or similar conditions.

Conjugates can be made by other suitable methods. For example, conjugates were made using 4FB-HyNic chemistry (Solulink), shown below.

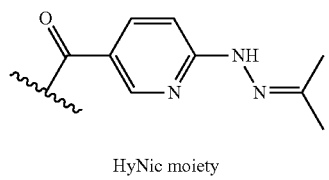 [SMILES: *C(=O)c1ccc(NN=C(C)C)nc1]

HyNic moiety

Usually, the antibody was modified using 4FB-NHS (Solulink), shown below.

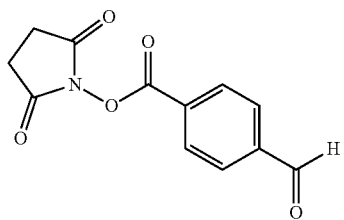

4-FB-NHS

Biotin ligase was modified with HyNic-NHS (Solulink). After removing excess reagent, 4FB-Ab was mixed with HyNic-Biotin ligase to form biotin ligase-Ab conjugates. The reaction was catalyzed using 10 mM aniline. The conjugation products were purified as above.

The enzymatic activity of the conjugates must be retained, or the conjugate is unsuitable for use in proximity target detection. Accordingly, the activity of conjugates was assayed, and the results of certain exemplary conjugate activity assays are provided in FIGS. 4-6.

B. Biotin Ligase Substrate Probes

Similarly, for the second probe to target B of the proximal pair, a biotin ligase substrate is conjugated to a specific binding moiety selected for its particular binding affinity for target B. Conjugation can be any method that effectively associates the biotin ligase substrate and the specific binding moiety, but most typically involves covalent conjugation.

For certain embodiments the peptide substrate biotin ligase target peptide sequence (BTS) was:

```
                                    SEQ. ID No. 10
GGSGLNDIFEAQKIEWHE.
```

A HyNic moiety was provided at the N-terminus to facilitate chemical conjugation by hydrazone chemistry. Other chemistries, e.g. sulfhydryl modification with maleimide chemistry, also are useful for forming suitable conjugates. The first three amino acids on BTS (GGS) serve as a linker for chemical conjugation.

In an exemplary method for making biotin ligase substrate conjugates, an antibody was combined with a 4FB-PEG-PFP active ester (Solulink S-1034). For these conjugates the PEG linker typically has from 2 to about 20 PEG units, more typically 2 to about 10 PEG units, and even more typically from 4 to 8 PEG units. For certain embodiments, the PEG linker was a $PEG_4$ linker. The mixture was purified, HyNic labeled BTS (from Biosynthesis, Inc.) was added to the purified 4FB-Ab and the resulting conjugate purified using a VIVASPIN filter. The ratio of BTS to antibody was determined by measuring the absorbance of 280 nm (Ab) and 350 nm (hydrazone bond formed from 4FB-HyNic reaction). Typically, this synthetic approach provided from 2 to about 5 BTS molecules per antibody. Examples of conjugates made according to this process include: goat anti-rabbit-BTS, goat anti-mouse-BTS, mouse anti-benzofurazan-BTS, and mouse antinitrophenyl-BTS.

C. Linker

For both the first and second probe the biotin ligase and the biotin ligase substrate can be directly coupled to the specific binding moiety without any intervening atoms. Conversely one or both of the first and second probes can also include a chemical linker that links the components, either biotin ligase or ligase peptide substrate, to a specific binding moiety. Linkers of different lengths can be selected to, for example, bring the substrate into sufficient proximity of the biotin ligase to allow biotinylation.

Typically, chemical linkers are bifunctional, i.e., the linker includes a functional group at each end, wherein the functional groups are used to couple the linker to the two conjugate components. The two functional groups may be the same, i.e., a homobifunctional linker, or different, i.e., a heterobifunctional linker, but more typically are heterobifunctional. Where linkers are employed, such groups may be chosen to allow for attachment of the two components of the conjugate, while not impairing their functionality. Such terminal functional groups, include by way of example and without limitation, amines, alcohols, thiols, hydrazides, carbonyl-reactive group (such as aldehydes, acids and esters), vinyl ketones, epoxides, isocyanates, maleimides), functional groups capable of cycloaddition reactions, forming disulfide bonds, binding to metals or photo-reactive groups. Specific examples include primary and secondary amines, hydroxamic acids, N-hydroxysuccinimidyl esters, N-hydroxysuccinimidyl carbonates, oxycarbonylimidazoles, nitrophenylesters, trifluoroethyl esters, glycidyl ethers, vinylsulfones, and maleimides. These groups facilitate coupling to the specific binding moieties and other desired compounds.

In some embodiments, the linker is generally at least about 50 daltons, but more particularly at least about 100 daltons and may be as large as 500 daltons or larger. A first class of linkers suitable for forming disclosed conjugates is the aliphatic compounds, such as aliphatic hydrocarbon chains having one or more sites of unsaturation, or alkyl chains. The length of the chain can vary, but typically has an upper practical limit of about 30 atoms. Chain lengths greater than about 30 carbon atoms have proved to be less effective than compounds having smaller chain lengths. Thus, aliphatic chain linkers typically have a chain length of from about 1 carbon atom to about 30 carbon atoms. However, a person of ordinary skill in the art will appreciate that, if a particular linker has greater than 30 atoms, and the conjugate still functions as desired, then such chain lengths are still within the scope of the present invention.

In one embodiment, the linker is a straight chain or branched alkyl chain functionalized with reactive groups, such as an amino- or mercapto-hydrocarbon, with more than two carbon atoms in the unbranched chain. Examples include aminoalkyl, aminoalkenyl and aminoalkynyl groups. Alternatively, the linker is an alkyl chain of 10-20 carbons in length, and may be attached through a Si—C direct bond or through an ester, Si—O—C, linkage (see U.S. Pat. No. 5,661,028 to Foote, incorporated herein by reference). Other linkers are available and known to a person of ordinary skill in the art (see, e.g., U.S. Pat. Nos. 5,306,518, 4,711,955 and 5,707,804; each of which is incorporated herein by reference).

A second class of linkers useful for practicing the present invention is the alkylene oxides. The alkylene oxides are represented herein by reference to glycols, such as ethylene glycols. Conjugates of the present invention have proved particularly useful if the hydrophilicity of the linker is increased relative to their hydrocarbon chains. A person of ordinary skill in the art will appreciate that, as the number of oxygen atoms increases, the hydrophilicity of the compound also may increase. Thus, linkers of the present invention typically have a formula of (—OCH2CH2—)n where n is from about 2 to about 20, but more particularly n is from about 2 to about 10, and even more typically from about 4 to about 8, which can be represented as $PEG_4$ to $PEG_8$.

Linkers, such as heterobifunctional polyalkyleneglycol linkers, useful for practicing certain disclosed embodiments of the present invention are described in assignee's co-pending applications, including "Nanoparticle Conjugates," U.S. patent application Ser. No. 11/413,778, filed Apr. 28, 2006; "Antibody Conjugates," U.S. application Ser. No. 12/381,638, filed Mar. 13, 2009; and "Molecular Conjugate," U.S. patent application Ser. No. 12/687,564, filed Jan. 14, 2010, and U.S. Pat. No. 7,695,929; each of which is incorporated herein by reference. The linkers disclosed in these applications can be used to link specific binding moieties, biotin ligases, biotin ligase substrates, signal generating moieties and haptens in any and all desired combinations to form conjugates for use with disclosed embodiments of the present invention.

Other examples of linkers include, but are not limited to, peptides, including natural and non-natural polypeptides, carbohydrates, cyclic or acyclic systems that may possibly contain heteroatoms. Linker groups also may comprise ligands that bind to metals such that the presence of a metal ion coordinates two or more ligands to form a complex. In another embodiment, the linker is a pair of molecules, having high affinity for one another. Such high-affinity molecules include, for example, streptavidin and biotin, histidine and nickel (Ni), and GST and glutathione.

Specific exemplary linkers include: ethylene glycol, polyalkylene glycols such as $PEG_2$, $PEG_3$, $PEG_4$, $PEG_5$, $PEG_6$, $PEG_7$, $PEG_8$, $PEG_9$, $PEG_{10}$, $PEG_{11}$, $PEG_{12}$, $PEG_{13}$, $PEG_{14}$, $PEG_{15}$, $PEG_{16}$, $PEG_{17}$, $PEG_{18}$, $PEG_{19}$, $PEG_{20}$, 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine, succinimidyl-6-hydrazinonicotinamide (S-HyNic, HyNic-NHS), N-succinimidyl-4-formylbenzoate (S-4FB, 4-FB-NHS), maleimide HyNic (MHPH), maleimide 4FB (MTFB), succinimidyl-[(N-maleimidopropionamido)-octaethyleneglycol]ester (Mal-$PEG_8$-NHS), succinimidyl-[(N-maleimidopropionamido)-tetraethyleneglycol]ester (Mal-$PEG_4$-NHS), 4-FB-$PEG_4$-PFP, azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl]aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), 4-(N-maleimidomethyl)-cyclohexane-1-carboxylic acid N-hydroxysuccinimide ester (SMCC), and the like.

D. Fusion Proteins

Instead of chemical linkers, the enzyme or peptide substrate can be coupled to the specific binding moiety at the gene level. For example, fusion proteins can be used in which the biotin ligase and/or the biotin peptide substrate are fused to an antibody rather than conjugated using a linker.

Fusion proteins that encode a biotin ligase and a sequence for a specific binding moiety can be used. For example, the following DNA nucleotide sequence was made by a combination of gene synthesis, PCR and Gibson assembly.

SEQ ID. No. 11
```
ACATATGCGTGGTAGCCACCACCACCATCATCACGGTAGCGATTTGGGTA
AGAAATTGCTGGAGGCAGCACGCGCAGGTCAGGATGACGAAGTGCGTATC
CTGATGGCGAATGGCGCGGACGTGAACGCTAAAGACGAATACGGCCTGAC
GCCGCTGTATCTGGCAACCGCCCATGGCCACCTGGAAATCGTTGAAGTCC
TGTTGAAAAACGGTGCCGACGTTAATGCTGTTGATGCGATTGGTTTCACC
CCGCTGCATCTGGCCGCGTTTATCGGTCACCTGGAGATTGCGGAGGTGCT
GCTGAAACACGGTGCGGATGTCAACGCACAGGATAAGTTTGGCACCGCGT
TCGACATCAGCATTGGCAACGGCAATGAGGACCTGGCGGAGATTCTGCAA
AAGCTGATGAAGGATAACACCGTGCCACTGAAATTGATTGCCCTGTTAGC
GAACGGTGAATTTCACTCTGGCGAGCAGTTGGGTGAAACGCTGGGAATGA
GCCGGGCGGCTATTAATAAACACATTCAGACACTGCGTGACTGGGGCGTT
GATGTCTTTACCGTTCCGGGTAAAGGATACAGCCTGCCTGAGCCTATCCA
GTTACTTAATGCTAAACAGATATTGGGTCAGCTGGATGGCGGTAGTGTAG
CCGTGCTGCCAGTGATTGACTCCACGAATCAGTACCTTCTTGATCGTATC
GGAGAGCTTAAATCGGGCGATGCTTGCATTGCAGAATACCAGCAGGCTGG
CCGTGGTCGCCGGGGTCGGAAATGGTTTTCGCCTTTTGGCGCAAACTTAT
ATTTGTCGATGTTCTGGCGTCTGGAACAAGGCCCGGCGGCGGCGATTGGT
TTAAGTCTGGTTATCGGTATCGTGATGGCGGAAGTATTACGCAAGCTGGG
TGCAGATAAAGTTCGTGTTAAATGGCCTAATGACCTCTATCTGCAGGATC
GCAAGCTGGCAGGCATTCTGGTGGAGCTGACTGGCAAAACTGGCGATGCG
GCGCAAATAGTCATTGGAGCCGGGATCAACATGGCAATGCGCCGTGTTGA
AGAGAGTGTCGTTAATCAGGGGTGGATCACGCTGCAGGAAGCGGGGATCA
ATCTCGATCGTAATACGTTGGCGGCCATGCTAATACGTGAATTACGTGCT
GCGTTGGAACTCTTCGAACAAGAAGGATTGGCACCTTATCTGTCGCGCTG
GGAAAAGCTGGATAATTTTATTAATCGCCCAGTGAAACTTATCATTGGTG
ATAAAGAAATATTTGGCATTTCACGCGGAATAGACAAACAGGGGCTTTA
TTACTTGAGCAGGATGGAATAATAAAACCCTGGATGGGCGGTGAAATATC
CCTGCGTAGTGCAGAAAAATAACTCGAG
```

This sequence encodes a fusion protein with the following amino acid sequence:

SEQ. ID NO. 12
```
MRGSHHHHHHGSDLGKKLLEAARAGQDDEVRILMANGADVNAKDEYGLTP
LYLATAHGHLEIVEVLLKNGADVNAVDAIGFTPLHLAAFIGHLEIAEVLL
```

KHGADVNAQDKFGTAFDISIGNGNEDLAEILQKLMKDNTVPLKLIALLAN

GEFHSGEQLGETLGMSRAAINKHIQTLRDWGVDVFTVPGKGYSLPEPIQL

LNAKQILGQLDGGSVAVLPVIDSTNQYLLDRIGELKSGDACIAEYQQAGR

GRRGRKWFSPFGANLYLSMFWRLEQGPAAAIGLSLVIGIVMAEVLRKLGA

DKVRVKWPNDLYLQDRKLAGILVELTGKTGDAAQIVIGAGINMAMRRVEE

SVVNQGWITLQEAGINLDRNTLAAMLIRELRAALELFEQEGLAPYLSRWE

KLDNFINRPVKLIIGDKEIFGISRGIDKQGALLLEQDGIIKPWMGGEISL

RSAEK#

With reference to SEQ. ID No. 12, the bold letters identify the biotin ligase coding sequence. The non-bold letters are the sequence of an anti-Her2 DARPin known to bind the HER2 antigen in formalin-fixed paraffin embedded tissue samples. The hexahistidine sequence at the amino terminus facilitates protein purification. Zahnd et at J. Mol. Boil. (2007) 369, 1015-1028.

Another example is DNA with the following nucleotide sequence, which was made by gene synthesis, PCR and Gibson assembly.

SEQ. ID NO. 13
ATGGCTCAAGTACAACTGCAGCAATCTGGTACAGAGGTAGTTAAACCTGG

CGCCTCTGTCAAATTGAGTTGCAAGGCTAGTGGTTACATTTTCACCTCTT

ATGACATTGACTGGGTTCGTCAAACTCCAGAACAAGGATTGGAATGGATT

GGGTGGATCTTTCCTGGTGAGGGCTCTACGGAATACAACGAGAAGTTTAA

GGGTAGAGCTACACTTAGTGTCGATAAGTCCTCCTCAACTGCTTACATGG

AGCTTACGAGACTTACATCAGAAGATTCAGCCGTGTATTTCTGTGCTAGA

GGAGATTACTACCGAAGGTACTTCGACTTATGGGCCAGGGTACTACTGT

GACAGTCAGTTCCGGAGGAGGAGGTTCCGGGGGTGGTGGTTCTGGCGGTG

GTGGATCTGATATTGAGTTGACTCAATCACCCACTATCATGTCCGCTTCT

CCTGGTGAAAGAGTTACCATGACATGTTCAGCATCTAGTTCAATCAGATA

CATCTATTGGTACCAGCAGAAGCCCGGCTCCTCCCCACGTTTACTGATAT

ACGACACCTCAAATGTTGCATCTGGTGTTCCATCAAGATTTTCTGGATCA

GGATCCGGAACAAGTTATTCCCTAACCATAAACAGGATGGAAGCAGAGGA

TGCTGCCACGTATTACTGTCAAGAGTGGTCTGGCTATCCTTACACCTTTG

GTGGTGGGACTAAGTTGGAATTGAAACAGGCCGCTGCAGGGCCCCGTCAA

AAGGGCGACACAAAATTTATTCTAAATGCAGGTGGCGGTCTGAACGACAT

CTTCGAGGCTCAGAAAATCGAATGGCACGAATAA

This sequence encodes a fusion protein with the following amino acid sequence:

SEQ. ID NO. 14
MAQVQLQQSGTEVVKPGASVKLSCKASGYIFTSYDIDWVRQTPEQGLEWI

GWIFPGEGSTEYNEKFKGRATLSVDKSSSTAYMELTRLTSEDSAVYFCAR

GDYYRRYFDLWGQGTTVTVSSGGGGSGGGGSGGGGSDIELTQSPTIMSAS

PGERVTMTCSASSSIRYIYWYQQKPGSSPRLLIYDTSNVASGVPSRFSGS

GSGTSYSLTINRMEAEDAATYYCQEWSGYPYTFGGGTKLELKQAAAGPRQ

KGDTKFILNAGGGLNDIFEAQKIEWHE#

The bold letters indicate the BTS amino acid sequence that can be biotinylated by biotin ligase. The sequence that is not in bold is for a mouse anti-rabbit SCFV derived from the monoclonal antibody A10B. Shen et at Anal. Chem. 2005, 77, 6834-6842.

Similarly, a fusion protein in which the anti-rabbit SCFV is fused to the biotin ligase has been made and the sequence is provided below:

SEQ. ID NO. 15
MAQVQLQQSGTEVVKPGASVKLSCKASGYIFTSYDIDWVRQTPEQGLEWI

GWIFPGEGSTEYNEKFKGRATLSVDKSSSTAYMELTRLTSEDSAVYFCAR

GDYYRRYFDLWGQGTTVTVSSGGGGSGGGGSGGGGSDIELTQSPTIMSAS

PGERVTMTCSASSSIRYIYWYQQKPGSSPRLLIYDTSNVASGVPSRFSGS

GSGTSYSLTINRMEAEDAATYYCQEWSGYPYTFGGGTKLELKQAAAGPRQ

KGDTKFILNAMKDNTVPLKLIALLANGEFHSGEQLGETLGMSRAAINKHI

QTLRDWGVDVFTVPGKGYSLPEPIQLLNAKQILGQLDGGSVAVLPVIDST

NQYLLDRIGELKSGDACIAEYQQAGRGRRGRKWFSPFGANLYLSMFWRLE

QGPAAAIGLSLVIGIVMAEVLRKLGADKVRVKWPNDLYLQDRKLAGILVE

LTGKTGDAAQIVIGAGINMAMRRVEESVVNQGWITLQEAGINLDRNTLAA

MLIRELRAALELFEQEGLAPYLSRWEKLDNFINRPVKLIIGDKEIFGISR

GIDKQGALLLEQDGIIKPWMGGEISLRSAEK

Biotin Ligase is indicated by bold letters, whereas the anti-rabbit SCFV is not bold.

A DARPin fusion protein having the following amino acid sequence also has been made, where the BTS sequence, in bold, is fused to the C terminus of the DARPin.

SEQ. ID NO. 16
MRGSHHHHHHGSDLGKKLLEAARAGQDDEVRILMANGADVNAKDEYGLTP

LYLATAHGHLEIVEVLLKNGADVNAVDAIGFTPLHLAAFIGHLEIAEVLL

KHGADVNAQDKFGTAFDISIGNGNEDLAEILQKLGGGLNDIFEAQKIEWH

E#

A person of ordinary skill in the art also will appreciate that the biotin ligase and/or the biotin ligase peptide substrate can be at the N terminus or the C terminus, in a single chain variable fragment (SCFV), such as in the spacer between the heavy and light chain coding regions. A person of ordinary skill in the art also will appreciate that the biotin ligase and/or the biotin ligase peptide substrate could be present as more than one copy at either or both ends.

E. Chemical Formulas for Exemplary Conjugates

Conjugates of the present invention typically comprise a specific binding moiety (SBM) conjugated to a biotin ligase or biotin ligase substrate. A first general formula describing certain embodiments of the present disclosure is SBM-(ligase or substrate). Such compounds also optionally include a linker. Embodiments having a linker satisfy the formula SBM-linker-(ligase or substrate). A combined general formula for certain disclosed conjugates therefore is SBM-([linker]$_m$-(biotin ligase or biotin ligase substrate)]$_n$ where m is 0 to 5 and n is 1 to 10. More particularly, m is 0 to 2 and n is 1 to 5. When m is greater than 1 the linker includes plural different subcomponents. For example, both a SBM and a biotin ligase can include attached linkers, wherein the linkers can then be reacted to couple the SBM and the ligase together.

In a particular embodiment, a conjugate according to the disclosure has the general structure SBM-(linker)$_m$-biotin ligase, where m=0 to 10, and more typically m=0 to 2. In one example, the linker comprises a PEG linker, such as PEG$_2$, PEG$_3$, PEG$_4$, PEG$_5$, PEG$_6$, PEG$_7$, PEG$_8$, PEG$_9$, PEG$_{10}$, PEG$_{11}$, PEG$_{12}$, PEG$_{13}$, PEG$_{14}$, PEG$_{15}$, PEG$_{16}$, PEG$_{17}$, PEG$_{18}$, PEG$_{19}$ or PEG$_{20}$. For these embodiments, a PEG$_4$ is considered a single linker, as opposed to a linker comprising 4 separate subunits. In more particular embodiments, the SBM is an antibody. In still more particular embodiments, the biotin ligase is from BirA.

In a specific example Goat anti Rabbit (GAR) was conjugated to biotin ligase with a PEG$_8$ linker. This satisfies the formula SBM-(linker)$_m$-biotin ligase, where the SBM is GAR, the linker is PEG$_8$, m=1 and the ligase is from BirA.

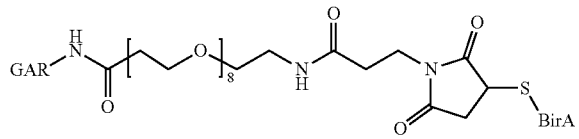

The PEG$_8$ group is attached to the GAR through an amide linkage formed between a carboxylic acid functional group on one end of the PEG chain and an amine on the GAR. The other end of the PEG chain includes an active maleimide (MAL) group, which couples to an active sulfhydryl group on the biotin ligase.

Another example of a biotin ligase-antibody conjugate is an anti-hapten antibody:biotin ligase conjugate, such as mouse anti-nitrophenyl-PEG$_8$-biotin ligase.

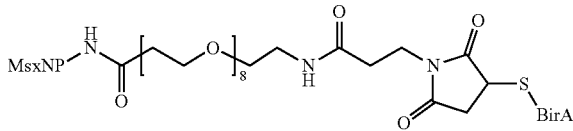

As in the previous example, the linker was coupled via an amide bond to the antibody and to the biotin ligase through a MAL group.

Yet another example is mouse anti nitrophenyl (MsxNP)-4FB-HyNic-biotin ligase.

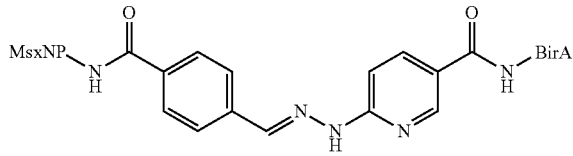

In this example the linker is 4FB-HyNic, formed by activating an amine on the MsxNP with 4-formylbenzoate, and activating an amine on the biotin ligase with a HyNic group. These two groups then couple to form the conjugate.

In another example, a conjugate according to disclosed embodiments of the present invention has the general structure SBM-(linker)$_m$-biotin ligase substrate, where m=0 to 10, and more particularly m=0 to 2. In one example, the linker comprises a PEG linker, such as PEG$_2$, PEG$_3$, PEG$_4$, PEG$_5$, PEG$_6$, PEG$_7$, PEG$_8$, PEG$_9$, PEG$_{10}$, PEG$_{11}$, PEG$_{12}$, PEG$_{13}$, PEG$_{14}$, PEG$_{15}$, PEG$_{16}$, PEG$_{17}$, PEG$_{18}$, PEG$_{19}$ or PEG$_{20}$. In more particular embodiments, the substrate is BTS.

In a specific example goat anti Rabbit (GAR) is conjugated to BTS through a PEG$_4$ linker. This satisfies the formula SBM-(linker)$_m$-substrate, where the SBM is GAR, the linker is PEG$_4$, m=1, and the substrate is BTS.

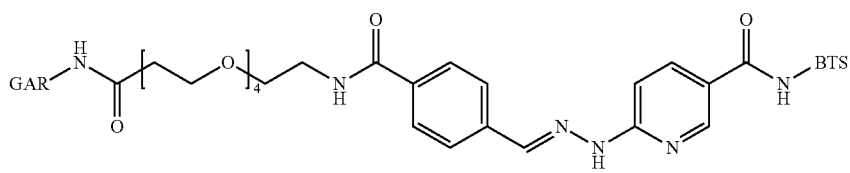

The PEG$_4$ group is attached to the GAR through an amide linkage formed between a carboxylic acid functional group on one end of the PEG chain and an amine on the GAR. The other end of the PEG chain has been activated with a 4FB group which is coupled to a HyNic group attached to the BTS.

Another example is an anti-antibody:biotin ligase substrate conjugate, such as goat anti mouse (GAM)-PEG$_4$-BTS.

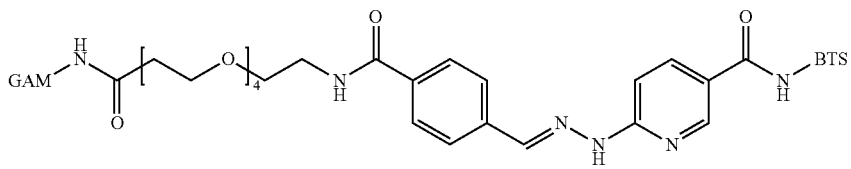

As in the previous example the GAM is coupled to the PEG₄ via an amide bond. The PEG₄ is then attached to the BTS through 4FB-HyNic chemistry.

Another example is an anti-hapten antibody:biotin ligase substrate conjugate, such as mouse anti BF (MsxBF)-PEG₄-BTS.

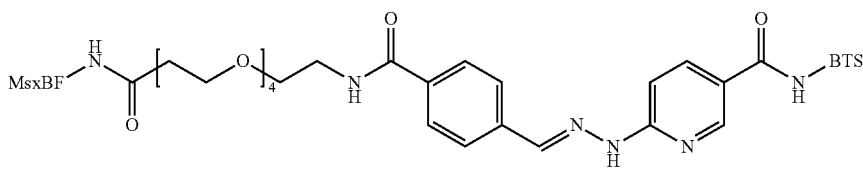

Yet another example of an anti-hapten antibody:biotin ligase substrate conjugate is mouse anti-nitrophenyl-PEG₄-BTS.

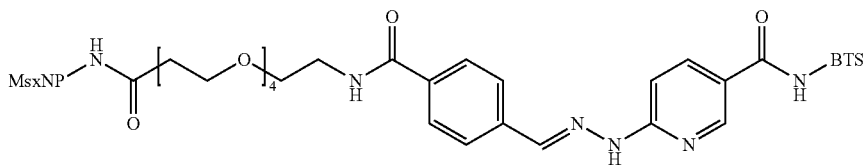

IV. Method for Detecting Targets

A. General Discussion

FIG. 1 illustrates schematically one embodiment of a method according to the present invention for detecting two proximal targets. Two targets, A and B, are located potentially in close proximity in a sample. The sample is contacted with a first probe conjugate comprising a biotin ligase and an anti-A antibody under conditions that allow the conjugate to associate with target A. The sample is contacted, either simultaneously or sequentially, with a second probe conjugate comprising a biotin ligase substrate and an anti-B antibody coupled under conditions that allow the conjugate to associate with target B. Following association of the probes with the respective targets, biotin ligase has to be within a reactive distance proximity to the biotin ligase substrate in order for biotinylation to occur. The biotinylation reaction is biotin and ATP dependent. Upon addition of these reagents, and if the biotin ligase and biotin ligase substrate are in sufficiently close proximity, the biotin ligase substrate is biotinylated.

B. Model Systems

Force proximity assays were conducted for biotin ligase and BTS conjugates by binding the conjugates to the same molecule, or different molecules linked to the same molecule. These assays served as model systems for testing the activity of various biotin ligase conjugates on tissue slides, as well as to demonstrate the feasibility of biotin ligase-based in situ detection of protein proximity in FFPE tissue. Three model systems were used: Model System 1—Single Antibody Forced Proximity; Model System 2—Haptenylated-Antibody Forced Proximity; and Model System 3—Hapten Labeled BSA.

Figure 3:
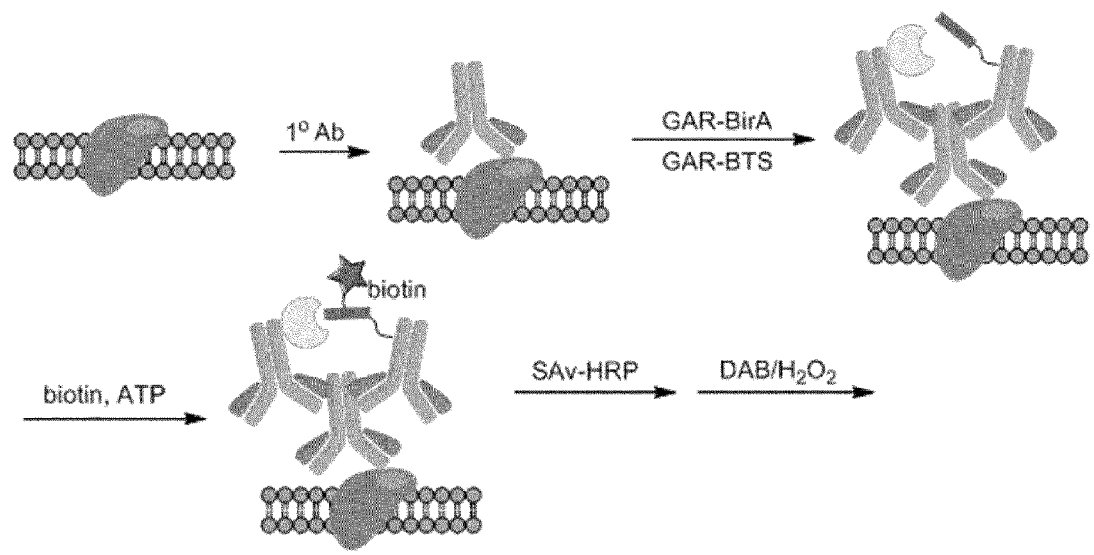
FIG. 3 schematically illustrates one embodiment of a forced proximity model system using biotin ligase and BTS conjugates associated with a single primary antibody that is associated with a target.

Model system 1 is illustrated schematically in FIG. 3. A single target in a sample was associated with a primary antibody, such as a rabbit antibody selected for associating with a target. Two conjugates were then made: the first conjugate was a goat-anti-rabbit antibody:biotin ligase conjugate; the second conjugate was a goat anti-rabbit antibody:BTS conjugate. The sample was contacted with these two conjugates, and the conjugate associated with the rabbit primary antibody. Binding both biotin ligase and a biotin ligase substrate to the same molecule on tissue induced close proximity, allowing physical contact of the biotin ligase active site with BTS. This resulted in biotinylation of BTS upon addition of biotin and ATP. The presence of biotin following the reaction was a positive indication that the biotin ligase and BTS were in sufficiently close reaction proximity to allow biotinylation.

Biotin can be detected by any known process. FIG. 3 illustrates using a streptavidin-horseradish peroxidase (HRP) conjugate that forms the specific binding pair between biotin and streptavidin. The presence of HRP was detected using diaminobenzidine (DAB)/H₂O₂ staining.

This process has been used on FFPE tissue. For example, Ki-67 detection in tonsil tissue has been accomplished using a single antibody forced proximity assay. Tonsil tissue was contacted with a rabbit-anti-Ki-67 antibody. The sample was then contacted with a first probe conjugate comprising a goat-anti-rabbit antibody:biotin ligase conjugate, as well as a goat anti-rabbit antibody:BTS conjugate. The addition of ATP resulted in staining; indicating the presence of a biotinyated substrate, whereas no such staining was seen in the absence of ATP.

Figure 4:
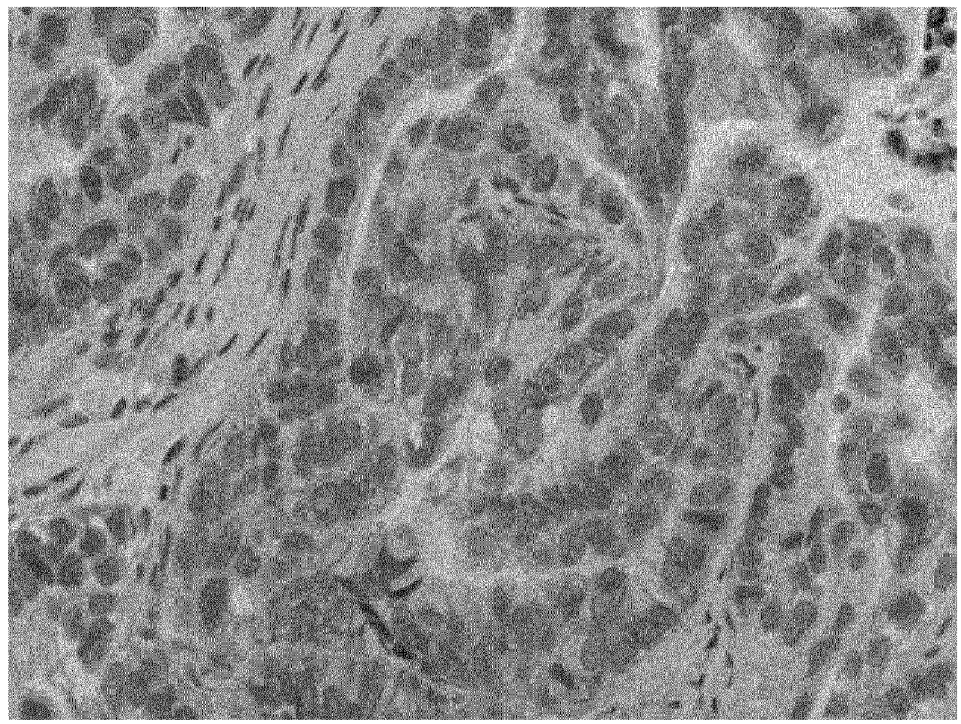
FIG. 4 is a photomicrograph illustrating HER2 detection using single antibody forced proximity.

Similarly, HER2 was detected using a single-antibody forced proximity assay. More specifically, HER2 was detected using biotin ligase-BTS biotinylation in a Calu-3 xenograft. Again, both a goat-anti-rabbit antibody:biotin ligase conjugate and a goat anti-rabbit antibody:BTS conjugate associated with rabbit-anti-HER2 (4B5) were used to enable HER2 detection. FIG. 4 is a photomicrograph of the staining resulting from using this detection protocol. These results provide an additional example demonstrating the utility of a biotin ligase-based in situ proximity assay.

Figure 5:
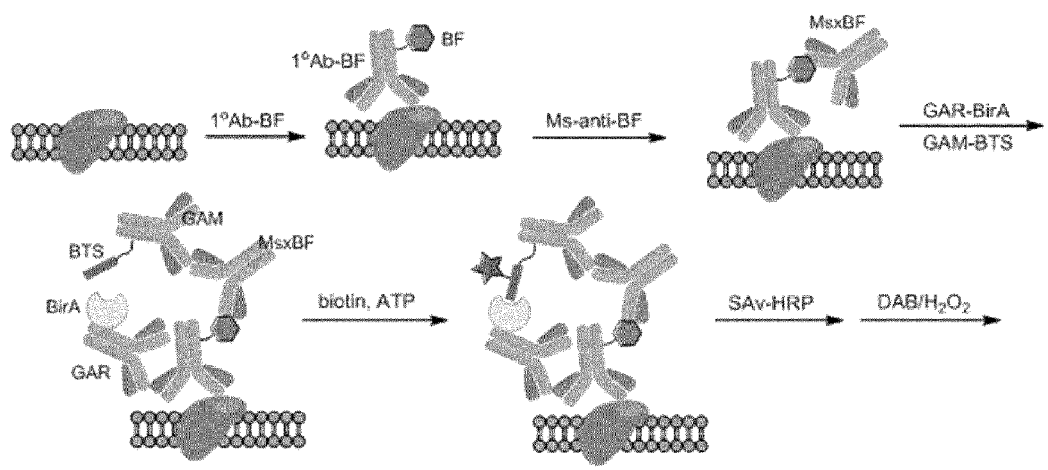
FIG. 5 is a schematic drawing illustrating a second model system that establishes the utility of a haptenylated-antibody proximity detection.

FIG. 5 is a schematic drawing illustrating a second model system used to establish the utility of a haptenylated-antibody embodiment. Close proximity was achieved using anti-hapten and anti-species conjugates, allowing successful biotinylation of BTS by biotin ligase.

With reference to FIG. 5, a single target in a sample was associated with a primary (1°) antibody conjugate selective for the desired target. The primary antibody conjugate comprised a rabbit antibody conjugated to a hapten, such as a benzofurazan hapten. The sample was then contacted with an anti-hapten antibody, such as a mouse anti-benzofurazan antibody, followed by a probe comprising a goat anti-rabbit antibody:biotin ligase conjugate. Finally, the sample was contacted with a probe comprising a goat anti-mouse antibody:BTS conjugate. This process forced both biotin ligase and BTS to bind to the same target and induced close proximity between the two, resulting in biotinylation of BTS upon addition of biotin and ATP. Biotin was detected using a streptavidin-horseradish peroxidase conjugate, followed by DAB/$H_2O_2$ staining. The utility of using a haptenylated-antibody in combination with a biotin ligase conjugate and a biotin ligase substrate conjugate to facilitate biotinylation of BTS was established by observation of positive staining.

Figure 6A:
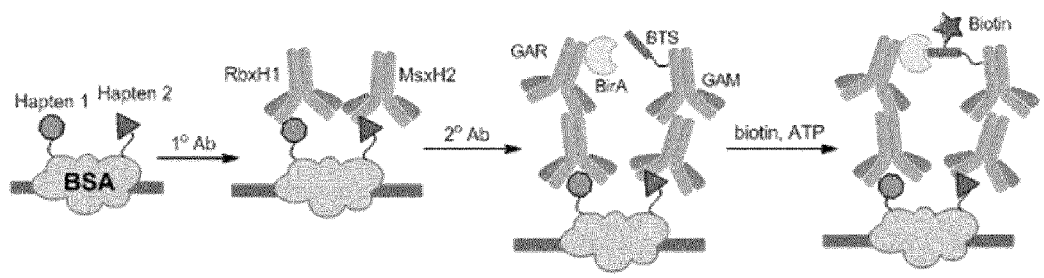
FIGS. 6A and 6B schematically illustrate an embodiment using a biotin ligase anti-antibody conjugate and biotin ligase substrate anti-antibody conjugate for detecting a dual hapten labeled target on a single substrate versus on two separate substrates, establishing target proximity effects.
Figure 6B:
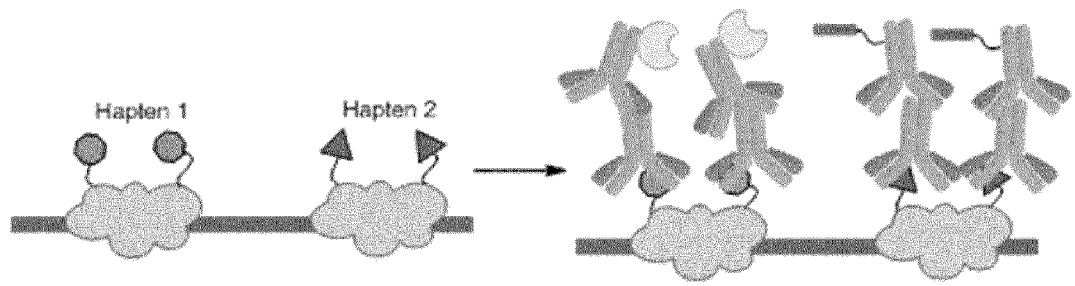

FIGS. 6A and 6B illustrate yet a third embodiment establishing the utility of using antibody-mediated detection of haptens, in combination with a biotin ligase conjugate and a biotin ligase substrate conjugate, to allow detection of proximally located targets by biotinylation. In the exemplary embodiment of FIG. 6A, BSA was simultaneously labeled with two haptens (hapten 1 and hapten 2) to position the two haptens in close proximity. FIG. 6A illustrates contacting a single target in a sample with a first hapten 1 and a second hapten 2. The sample was then contacted with a primary rabbit anti-hapten 1 antibody, and a primary mouse anti-hapten 2 antibody. The sample was then contacted with a goat anti-rabbit antibody:biotin ligase conjugate and a goat anti-mouse antibody:BTS conjugate. This process forced both biotin ligase and BTS to bind to the proximally located hapten 1 and hapten 2 on the sample, thereby inducing close proximity between biotin ligase and BTS, resulting in biotinylation of BTS upon addition of biotin and ATP.

FIG. 6B schematically illustrates a control for the embodiment illustrated in FIG. 6A. FIG. 6B illustrates contacting a first BSA molecule with hapten 1, and contacting a second BSA molecule with hapten 2. The BSA-hapten 1 sample was contacted with a rabbit anti-hapten 1 antibody, followed by a goat anti-rabbit antibody:biotin ligase conjugate. The BSA-hapten 2 sample was contacted with a mouse anti-hapten 2 antibody, followed by a goat anti-mouse antibody:BTS conjugate. No biotinylation was detected following the addition of biotin and ATP to this sample. In the method of FIG. 6B, BSA was modified with a single hapten separately and thus the two haptens were not on the same BSA molecule, leading to a much larger target separation distance than in FIG. 6A. Even by mixing the two types of hapten-modified BSA molecules together and using the same detection methodology as illustrated for FIG. 6A, the distance between bound biotin ligase and BTS was still too large to allow biotinylation, therefore resulting in negative staining.

C. Formalin Fixed Paraffin Embedded Samples

Figure 7:
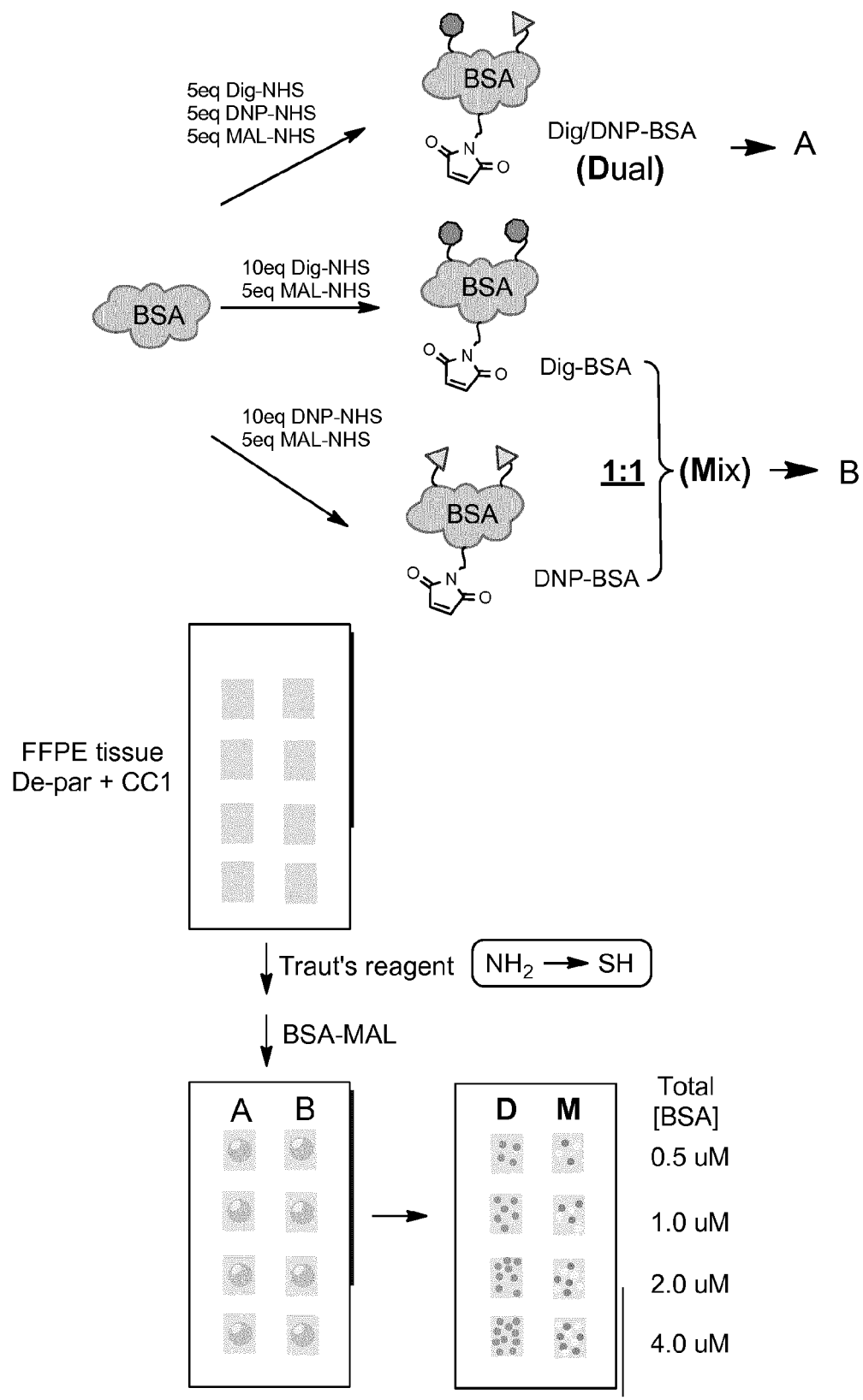
FIG. 7 is a schematic diagram illustrating the synthesis of hapten-labeled BSA, cross linking of BSA to thiolated tissue, and successful staining of hapten-BSA modified slides.

Certain disclosed embodiments of the present invention are particularly intended for use with formalin fixed paraffin embedded samples, such as are typically used with automated staining platforms. Accordingly, a model system was developed to establish the utility of disclosed embodiments of the present invention for use with formalin fixed paraffin embedded samples as illustrated by FIG. 7. With reference to FIG. 7, three different BSA-hapten conjugates were formed: a first conjugate comprised a hapten 1 and a hapten 2 located proximally on the same BSA molecule; a second comprised BSA-hapten 1 conjugate; and the third comprised a BSA-hapten 2 conjugate, thereby forming three conjugates similar to those described with reference to FIGS. 6A and 6B. A formalin fixed paraffin embedded sample on a slide was then contacted with these three conjugates. For dual hapten labeling with dinitrophenyl as a first hapten and digoxigenin as the second hapten, the first BSA-hapten 1/hapten 2 conjugate was made using excess Dig-NHS (Roche), excess DNP-$PEG_8$-NHS (Quanta Biodesign), and excess MAL-$PEG_8$-MAL (Quanta). This product is labeled Dig/DNP-BSA in FIG. 7. For mono-hapten labeling, an excess of Dig-NHS or DNP-$PEG_8$-NHS each with MAL-$PEG_8$-MAL (Quanta) was added. These products are labeled as Dig-BSA or DNP-BSA in FIG. 7 according to the hapten used. All three reaction products producing modified BSA were purified using Zeba mini spin columns.

Formalin fixed paraffin embedded placenta tissue slides were de-paraffinized and antigen retrieval was performed using standard conditioning on a Benchmark® XT (Ventana Medical Systems, Inc.) staining platform. Eight non-contacting tissue sections on each slide were created by removing portions of the tissue. The slides were then treated with Traut's reagents to convert disulfide groups on the tissue samples to thiols and the thiolated slides were used immediately.

The next step was to contact the thiolated tissue samples with the BSA conjugates. Four BSA concentrations (4 µM, 2 µM, 1 µM, and 0.5 µM) were used, either with the dual-labeled BSA or a 1:1 mixture of the mono-hapten labeled BSA. For all concentrations, 0.5 mg/mL of un-modified BSA was added to inhibit non-specific binding. Dual labeled BSA was then added to each tissue section in the left column of the slide. Mixtures of the mono-labeled BSA of the four total concentrations were added to the right column of the slide and labeled as "M". Free residual thiol groups on the tissue sample were quenched and the slide was rinsed thoroughly with water to remove any unbound molecules.

The slide was then contacted with primary antibody conjugates comprising mouse anti-digoxigenin and rabbit anti-dinitrophenyl antibodies. The sample was then contacted with secondary probes comprising a goat anti-rabbit antibody:biotin ligase conjugate and a goat anti-mouse antibody:BTS conjugate, followed by addition of biotin and ATP. Biotinylation was detected by streptavidin-HRP and DAB/$H_2O_2$ staining. Positive staining was observed for dual-hapten labeled BSA at all four concentrations, while only very faint staining was seen for the mixed mono-hapten labeled BSA even at the highest BSA concentration. At very high BSA total concentration, two mono-labeled BSA molecules might be in close proximity and detected. The probability of such event decreases dramatically with decreases in protein concentration as observed in this model system.

For the dual-labeled BSA, close proximity of two BSA molecules was not required since each and every BSA molecule included the necessary haptens to induce extremely high close proximity, leading to a substantially reduced BSA concentration dependency. These results further demonstrated distance stringency as well as feasibility for the biotin ligase mediated biotinylation for in situ detection of protein proximity in tissue.

D. E-Cadherin and β-Catenin

E-cadherin and its cytoplasmic binding proteins, catenins and p120 form a major inter-cellular adhesion complex. The complex is involved in cell migration, proliferation, and survival (e.g. signaling of Wnt and Rho pathways). β-Catenin is a multi-functional protein, i.e. it can serve as transcriptional co-activator by migrating to the cell nucleus. E-Cadherin and β-catenin, which are known to form complexes in polarized epithelia cell junctions, were used to confirm in situ detection of protein interaction in formalin fixed paraffin embedded samples according to disclosed embodiments of the present invention.

Three in situ biotin ligase proximity assays were tested. The first two embodiments were based on antibody and antibody-conjugate scaffoldings and the maximum distance between two targets in proximity was determined by the number of antibody and antibody-conjugates in the scaffold. The third embodiment used tyramide amplification to (1) amplify one of the target signals, which may be important for detecting low expressing targets, and (2) limiting diffusion of the activated-tyramide species from the TSA reaction prior to covalently linking to tissue proteins. Tyramide therefore serves as a reagent that allows selective distance bridging between targets of interest. Since the biotin ligase-BTS reaction requires physical contact between the enzyme active site with the peptide substrate, detecting fixed protein targets in FFPE tissue cannot always be achieved due to the distance and unknown orientation of the target molecules. The flexibility achieved by the tyramide deposition process is useful in these situations. While certain embodiments of the disclosure concern using a covalent or specific binding bridge to form between the first target and the second target, the use of the TSA reagents extends the signaling sphere of at least one of the targets (according to the diffusion of the tyramide reactive species). As such, the amplified target is replaced by a plurality of tertiary targets (e.g. haptens). Some of the tertiary targets are bound to the tissue on a tissue location closer to the first target such that the effective distance between the targets is reduced. This enables the proximity assay described herein to be used on targets that are at larger distances.

Figure 8A:
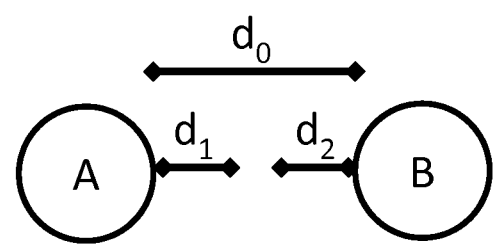
FIG. 8 is a schematic representation of a proximity assay with (8A) and without (8B) tyramide signal amplification or the like, where a first target (A) and a second target (B) are separated by a distance $d_0$.
Figure 8B:
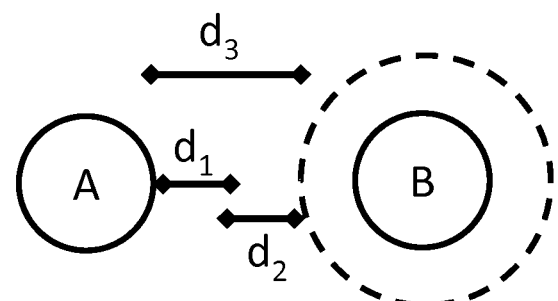

FIG. 8A is a schematic representation of one embodiment of a proximity assay without (FIG. 8A) and with (FIG. 8B) tyramide signal amplification or the like. FIG. 8A shows a first target (A) and a second target (B) separated by a distance $d_0$. The length of a first conjugate (e.g. a biotin ligase conjugate) is shown as $d_1$ and the length of a second conjugate (e.g. a BTS conjugate) is shown as $d_2$. When $d_0$ is larger than the sum of $d_1$ and $d_2$, the conjugates do not interact, and as a result no signal is observed. Referring to FIG. 8(B), amplification (e.g. tyramide signal amplification) can be used to increase the effective size of one of the targets (shown as a dotted line around (B)). With amplification, tertiary targets are deposited in the vicinity of the second target, with some of those tertiary targets being closer to the first target than the second target. As a result of the amplification, the effective distance, $d_3$, between the first and second target is reduced. When the effective distance, $d_3$, is smaller than the sum of $d_1$ and $d_2$, the conjugates can effectively interact and a signal will be observed.

A first in situ approach was performed in which E-cadherin in a sample was contacted with a rabbit anti-E-cadherin antibody. β-catenin in the sample was contacted with a mouse anti-β-catenin antibody. The sample was then contacted with a goat-anti-rabbit antibody:biotin ligase conjugate, and a goat anti-mouse antibody:BTS conjugate. Biotin and ATP were added to the sample. The presence of biotin was assayed using a streptavidin-horseradish peroxidase (HRP) conjugate, followed by diaminobenzidine (DAB)/$H_2O_2$ staining. No E-cadherin and β-catenin dimer signal was detected using this embodiment, indicating that the distance between the epitopes recognized by the primary antibodies is too large for the antibody scaffold to bring biotin ligase and BTS into direct contact.

It is understood that this result may be related to p120 and other membrane proteins being located between E-Cadherin and β-catenin. Accordingly, a second detection scheme was performed. A sample comprising E-Cadherin and β-catenin was first contacted with a mouse anti-β-catenin antibody, followed by a rabbit anti-E-Cadherin antibody. An anti-antibody-hapten conjugate was then used to detect the mouse anti-β-Catenin antibody. Specifically, the sample was contacted with a goat anti-mouse antibody:benzofurazan conjugate. The sample was then contacted with an anti-antibody biotin ligase conjugate and an anti-hapten-BTS conjugate. More particularly, the sample was contacted with a goat anti-rabbit antibody:biotin ligase conjugate and an anti-benzofurazan antibody:BTS conjugate. Biotin and ATP were added, followed by a streptavidin-horseradish peroxidase (HRP) conjugate, and diaminobenzidine (DAB)/$H_2O_2$ staining. Thus, the difference between this scheme and the first scheme was the addition of a hapten labeled anti-antibody.

Figure 9A:
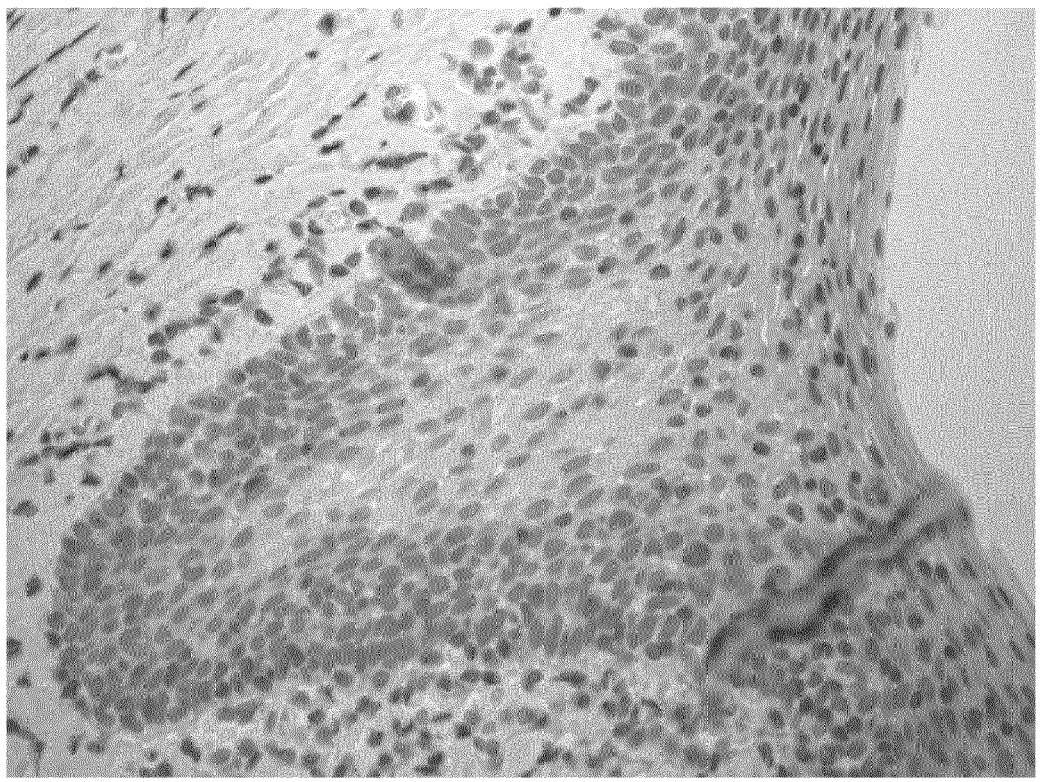
FIGS. 9A and 9B are photomicrographs illustrating the detection on tonsil of Ecad and β-catenin using one embodiment of the disclosed method further illustrating the ATP dependence of the reaction by no staining in the absence of ATP (FIG. 9A) and staining in the presence of ATP (FIG. 9B).
Figure 9B:
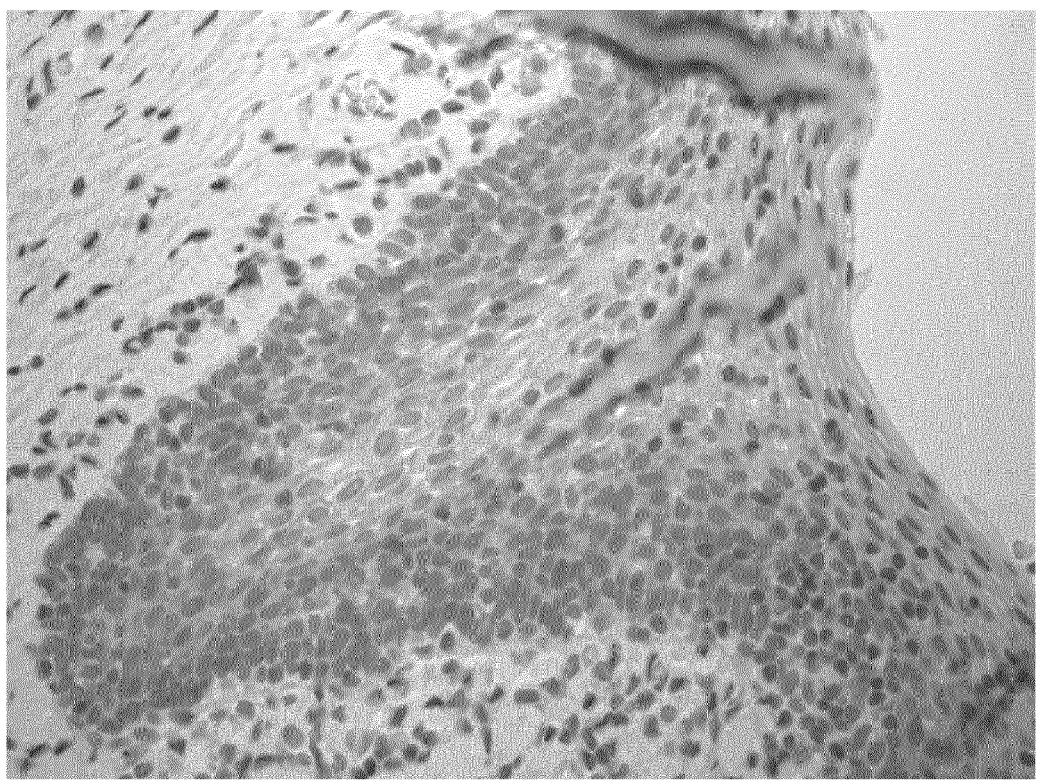

FIGS. 9A and 9B are photomicrographs of staining results achieved illustrating using this embodiment to detect E-Cadherin and β-Catenin on a tonsil sample and the dependence of detection on the addition of ATP. The specific detection of E-Cadherin and β-Catenin complex with this embodiment, compared to the previously discussed embodiment, establishes that one additional antibody (approximately a 10-20 nm distance) bridged the distance between biotin ligase and BTS, allowing biotinylation and detection of proximally located E-Cadherin and β-Catenin.

Figure 10A:
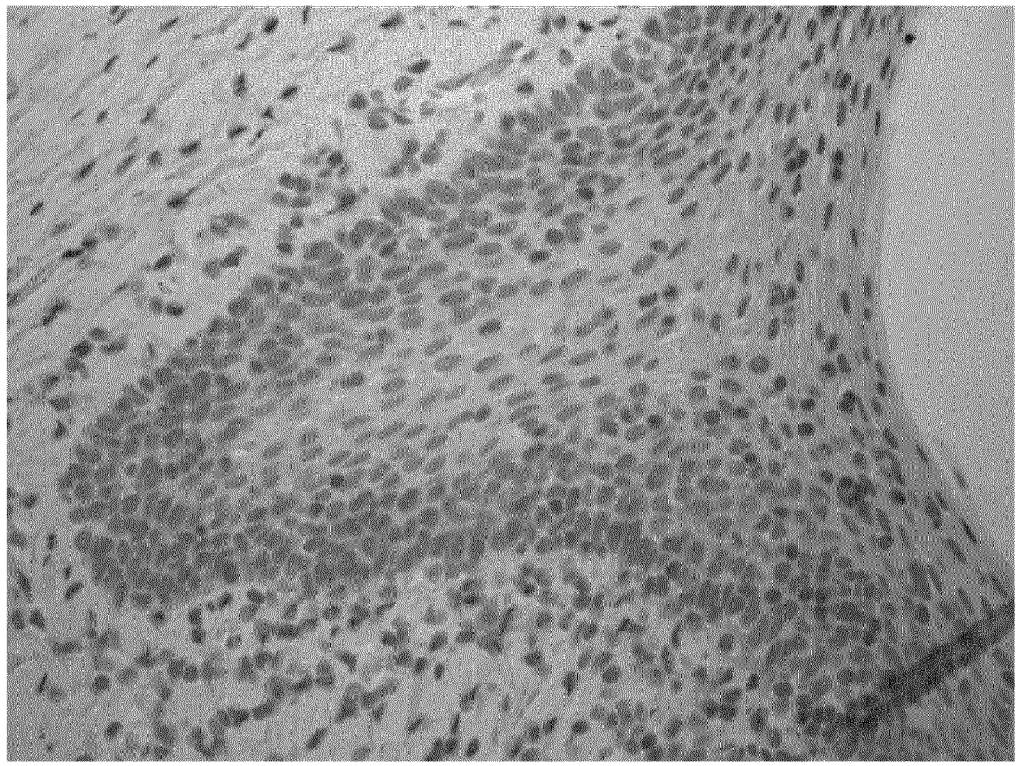
FIGS. 10A and 10B are photomicrographs illustrating the results of using TSA amplification.
Figure 10B:
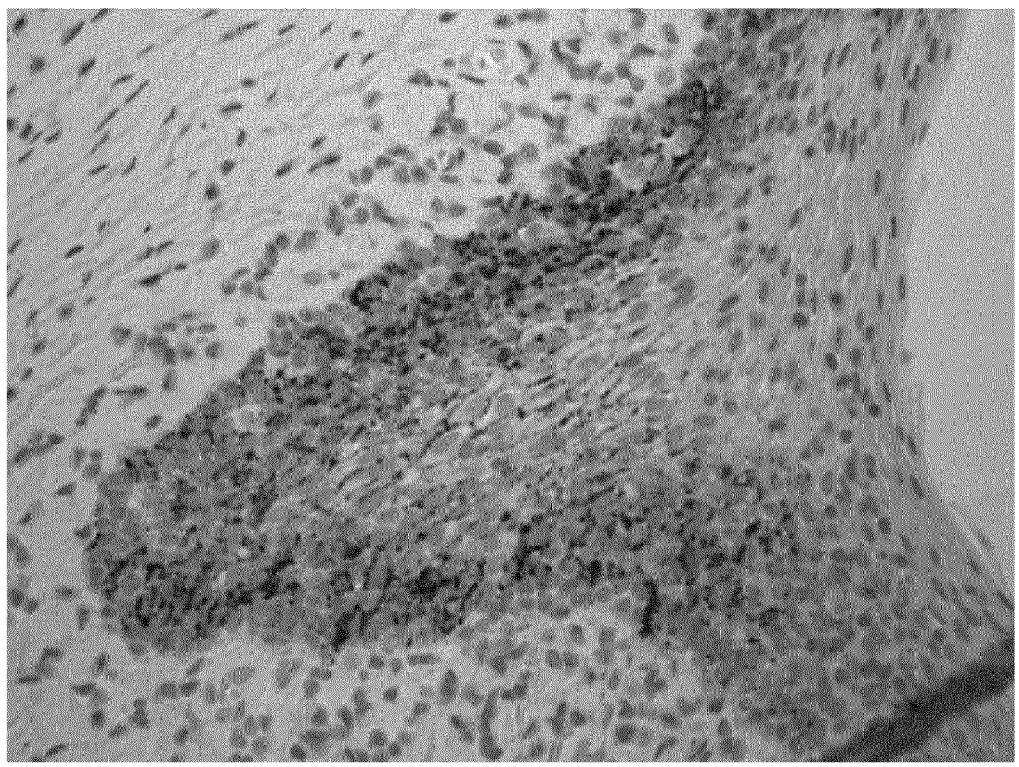

This same assay also was performed using TSA amplification (OPTIVIEW Amplification Kit, Ventana Medical Systems, Inc.) after biotin ligase biotinylation but prior to DAB detection. As illustrated by FIGS. 10A and 10B, specific biotinylation was observed while no increased background signal was observed on the slide without ATP. Thus, FIGS. 10A and 10B further demonstrate the high specificity of the biotin ligase reaction embodiments of the present invention. Moreover, this embodiment further establishes that E-Cadherin and β-Catenin are effectively closer as a result of TSA, as schematically illustrated in FIGS. 8A and 8B.

A first control system also was used to show that the detected signal was specific to E-Cadherin and β-Catenin. The control was used to establish that biotinylation did not occur as a result of affinity binding of a non-target associated biotin ligase with a peptide substrate. A sample comprising E-Cadherin and β-catenin was first contacted with a mouse anti-β-catenin antibody. However, the sample was not contacted with a rabbit anti-E-Cadherin antibody. An anti-antibody:hapten conjugate was then used to detect the mouse anti-β-Catenin antibody. Specifically, the sample was contacted with a goat anti-mouse antibody:benzofurazan conjugate. The sample was then contacted with an anti-antibody:biotin ligase conjugate and an anti-hapten:BTS conjugate. More particularly, the sample was contacted with a goat anti-rabbit antibody:biotin ligase conjugate and an anti-benzofurazan antibody:BTS conjugate. Biotin and ATP were added, followed by a streptavidin-horseradish peroxidase (HRP) conjugate, and diaminobenzidine (DAB)/$H_2O_2$ staining. The removal of one primary antibody (anti-E-Cadherin) was used as a negative control and no staining resulted.

Figure 11:
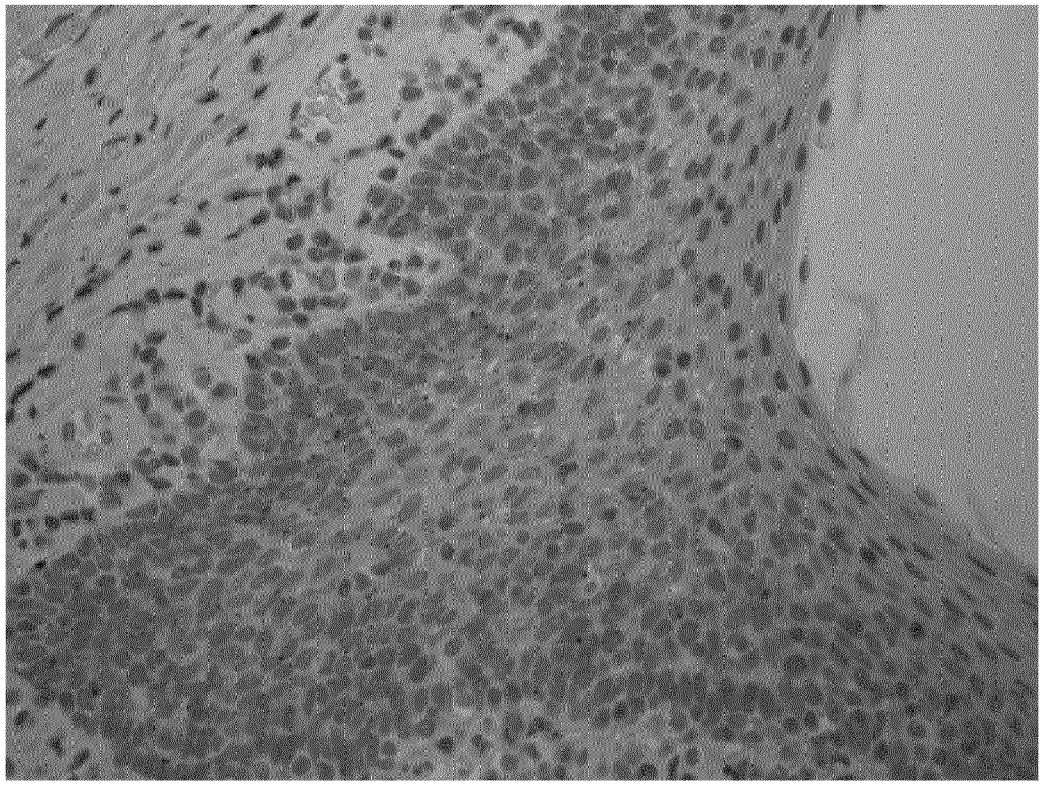
FIG. 11 is a photomicrograph of a second control utilizing competitive blocking of GAR-biotin ligase binding to anti-E-cadherin using excess GAR, resulting in attenuated signal with reduced amounts of biotin ligase bound to the target, thereby confirming that the detected signal was specific to E-cadherin and β-catenin.

A second control system included competitive blocking of goat anti-rabbit:biotin ligase conjugate to the sample to confirm that the detected signal was specific to E-Cadherin and β-Catenin. A sample comprising E-Cadherin and β-catenin was first contacted with a mouse anti-β-catenin antibody, followed by a rabbit anti-E-Cadherin antibody. The sample was then contacted with a goat-anti-mouse:benzofurazan conjugate. Next, the sample was contacted with (1) a goat anti-rabbit:biotin ligase conjugate, (2) an excess of goat anti-rabbit antibody to act as a competitive blocker, and (3) a goat anti-mouse:benzofurazan conjugate. An anti-antibody:hapten conjugate was then used to detect the mouse anti-β-catenin antibody. Biotin and ATP were added, followed by a streptavidin-horseradish peroxidase (HRP), and diaminobenzidine (DAB)/$H_2O_2$ staining. Competitive blocking of GAR-biotin ligase binding to anti-E-Cadherin with excess GAR was expected to attenuate the detection signal because less biotin ligase would bind to the target. The staining is shown in FIG. 11. Goat anti-rabbit competitive binding did produce a much weaker signal than the positive control.

TSA amplification was used to deposit haptens adjacent to a target to amplify target signal and simultaneously bridge the distance between E-Cadherin and β-catenin. In a first approach, a sample comprising E-Cadherin and β-catenin was contacted with a mouse anti-β-catenin antibody and a rabbit anti-E-Cadherin antibody. The sample was then contacted with a goat anti-mouse:HRP conjugate. TSA was then performed using a tyramide-benzofurazan conjugate. In a second approach, a sample comprising E-Cadherin and β-catenin was contacted with a mouse anti-β-catenin antibody and a rabbit anti-E-Cadherin antibody. TSA was then performed. The sample was then contacted with a goat anti-rabbit:biotin ligase conjugate, followed by an anti-benzofurazan:BTS conjugate. Biotin and ATP were added, the sample was contacted with a streptavidin:HRP conjugate, and DAB/$H_2O_s$ staining was performed.

Figure 12:
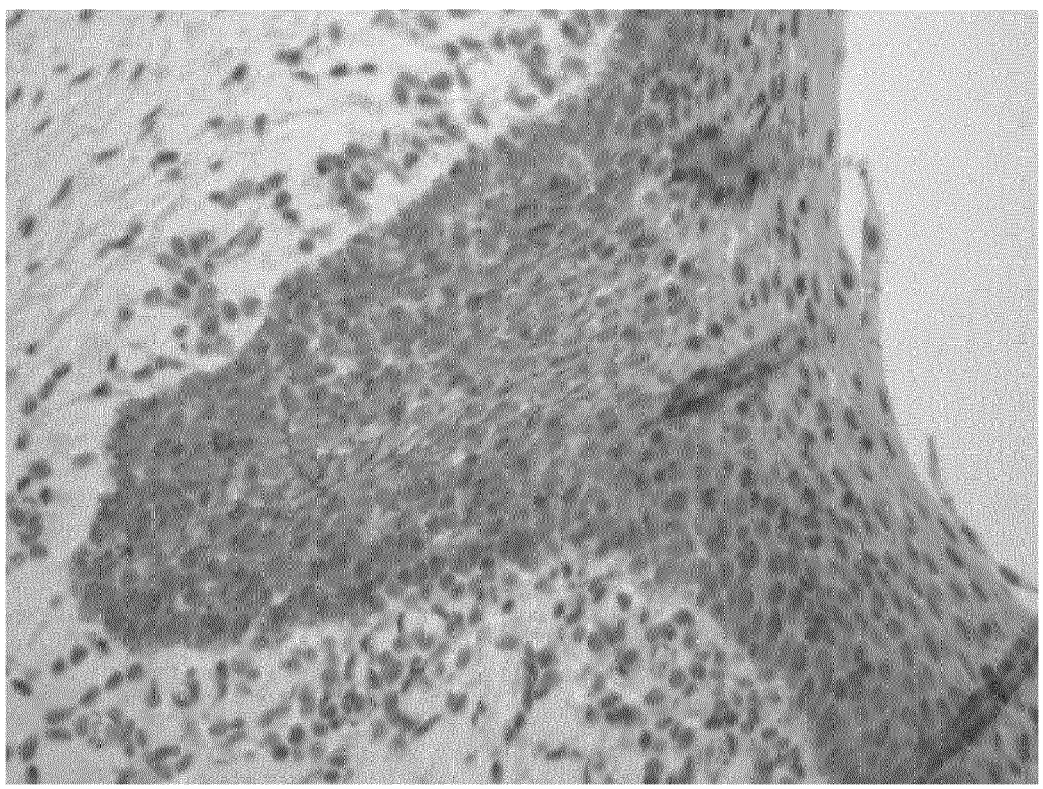
FIG. 12 is a photomicrograph illustrating the staining results obtained for a third disclosed embodiment of in situ proximity detection scheme for E-cadherin and β-catenin proximity assays comprising using TSA both as a bridge and to amplify the target signal.

The staining results in the presence of ATP are provided by FIG. 12. This embodiment successfully detected proximally located E-cadherin and β-catenin. Slides were produced using TSA with tyramide-benzofurazan and 16 minutes incubation as well as 8-minute Tyr-BF incubation. Shorter incubation times produced visible but weaker staining. No post-biotinylation amplification was used, although it could be so used to further amplify the signal. A time dependence of signal strength was observed for the amplification step. The signal associated with an 8 minute incubation was weaker than the signal associated with a 16 minute incubation. Essentially, it was observed that longer incubation times produced more intense signals. While not being limited to a particular theory, it is understood that the longer incubation time increases the number of tertiary targets and increases the signaling sphere, thereby reducing the effective distance between the two targets. The tyramide signal amplification is understood to nearly deplete the protein in the vicinity of the target of available groups to react with the reactive tyramide species. As such, the diffusion distance of the reactive tyramide species is expected to be increase over time as the number of available tissue reaction sites is depleted.

Proximity signals were detected between E-Cadherin and β-catenin with embodiments 2 and 3, but not with embodiment 1. The negative result from embodiment 1 indicated that the antibody and antibody conjugate scaffold did not bring biotin ligase and BTS into direct contact because of the distance between the two targets. However, by extending the scaffold, biotin ligase-mediated biotinylation was achieved and detected.

E. HER Receptor Tyrosine Kinases

Some human cancers are characterized by amplification and over expression of the human epidermal growth factor-2 (HER2) oncogene. HER2 has been best studied in the context of breast cancers. HER2 overexpression is associated with approximately 25% of all breast cancers and is correlated with aggressive forms of the disease. This suggests that HER2-driven breast cancers could be effectively treated through the pharmacological inactivation of tumor HER2 in patients. However, tyrosine kinase inhibitors (TKIs) that target the HER family show only limited clinical activity in patients with HER2-amplified breast cancer, producing only partial short-lived responses in a subset of patients.

HER2 is a member of the HER (or epidermal growth Factor Receptor; EGFR) family of receptor tyrosine kinases comprised of HER1 (EGFR), HER2 (ErbB2), HER3 (ErbB3), and HER4 (ErbB4). These homologous receptors share a common structure consisting of an extracellular ligand-binding domain, an intracellular tyrosine kinase domain, and a carboxyl-terminal signaling tail. The intracellular signal is generated as a consequence of receptor dimerization and trans-phosphorylation. With the exception of HER2, the extracellular domains do not permit dimerization unless they are structurally reconfigured by ligand binding. Dimerization among different members constitutes the principle mode of signaling in this family.

This interdependence is best exemplified by HER2 and HER3. HER2 has the strongest catalytic kinase activity and its extracellular domain permits dimerization without ligand binding. HER2 is the preferred dimerization partner for most other family members. The HER3 kinase domain lacks catalytic activity. HER3 depends on a heterodimeric partner for signaling. The functions of HER2 and HER3 are complementary to one another. The HER2-HER3 heterodimer forms a strong signaling dimer. The interdependent functions of HER2 and HER3 are evident from their behavior in cancer models. HER2 can transform cells by overexpression alone. Although HER3 cannot transform cells by itself, its co-expression synergistically enhances HER2 transformation. HER3 expression is rate-limiting for transformation in HER2-amplified breast cancers. The knockdown of HER3 reverses transformation in HER2-amplified tumors and induces tumor apoptosis.

A sample comprising HER2 and HER3 was first contacted with a primary rabbit anti-HER2 antibody and a primary mouse anti-HER3 antibody. An anti-antibody:hapten conjugate was then used to detect one of the primary antibodies. Specifically, the sample was contacted with a goat anti-mouse antibody:benzofurazan conjugate for detecting the primary antibody for HER3. The sample was then contacted with a goat anti-rabbit:biotin ligase conjugate for detecting the HER2 primary antibody, and an anti-benzofurazan:BTS conjugate. Biotin and ATP were added, followed by a streptavidin-horseradish peroxidase (HRP) conjugate, and diaminodenzidine (DAB)/$H_2O_2$ staining. This embodiment failed to detect HER2:HER3 dimers, suggesting that the distance was beyond the reach of the biotin ligase and BTS conjugate probe systems used in this embodiment.

A third embodiment was used to detect HER2:HER3 dimers. A sample comprising HER2 and HER3 was first contacted with a primary rabbit anti-HER2 antibody and a primary mouse anti-HER3 antibody. An anti-antibody:enzyme conjugate was then used to detect one of the primary antibodies. Specifically, the sample was contacted with a goat anti-mouse antibody:horseradish peroxidase conjugate for detecting the primary antibody for HER3, followed by TSA and benzofurazan deposition. The sample was next contacted with a goat anti-rabbit:biotin ligase conjugate for detecting the HER2 primary antibody, and an anti-benzofurazan:BTS conjugate. Biotin and ATP were added, followed by treatment with a streptavidin:alkaline phosphatase conjugate and alkaline phosphatase red.

Figure 13A:
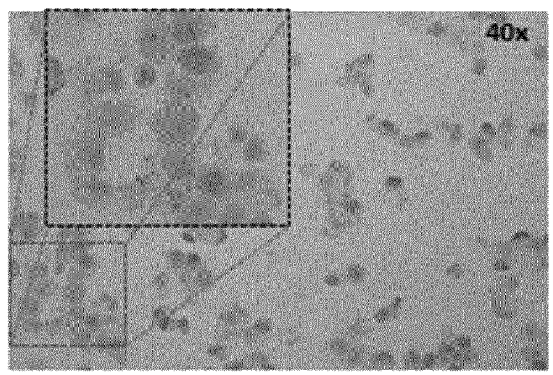
FIGS. 13A and 13B are photographs illustrating specific punctate HER2:HER3 dimer signals in the presence of ATP (FIG. 13A) and in the absence of ATP (FIG. 13B) on MDA-175.
Figure 13B:
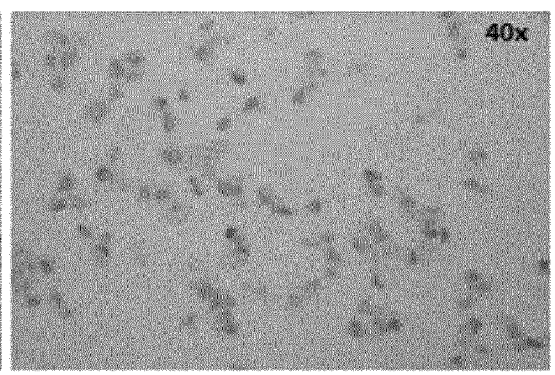
Figure 14A:
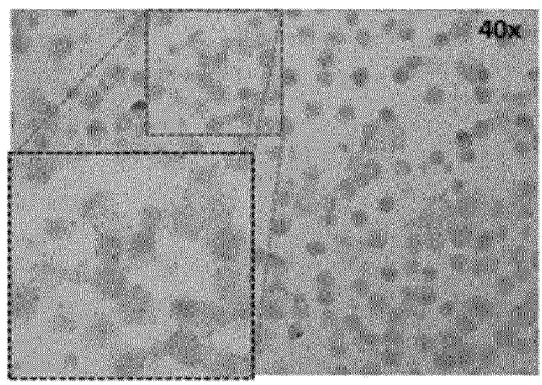
FIGS. 14A and 14B are photographs illustrating the staining results for HER:HER3 in situ proximity detection according to an embodiment of the present invention in the presence of ATP (FIG. 14A) and in the absence of ATP (FIG. 14B) on MCF-7.
Figure 14B:
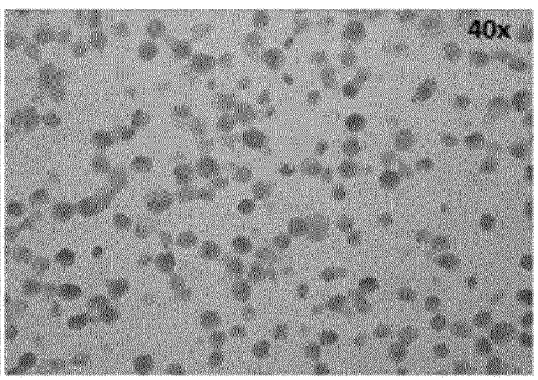

The results obtained using this detection methodology are illustrated in FIGS. 13-14. FIGS. 13A and 13B are photomicrographs illustrating specific punctate HER2:HER3 dimer signals in the presence of ATP (FIG. 13A) and in the absence of ATP (FIG. 13B) on formalin-fixed paraffin-embedded (FFPE) MDA-175 cancer cell line. FIGS. 14A and 14B are photomicrographs illustrating the staining results for HER:HER3 in situ proximity detection in the presence of ATP (FIG. 14A) and in the absence of ATP (FIG. 14B) on FFPE MCF-7 cancer cell lines. These results demonstrate that using TSA to deposit haptens around one target both amplifies the HER2 signal and bridges the distance between two membrane receptors.

V. Tyramide Signal Amplification (TSA)

Some embodiments include TSA, which is a peroxidase-based signal amplification system that is compatible with in situ hybridization (ISH), immunocytochemical, and immunohistochemical (IHC) detection schemes. TSA utilizes the catalytic activity of a peroxidase enzyme to "activate" a phenol moiety, such as provided by tyramine. Some peroxidase enzymes (e.g., horseradish peroxidase), in the presence of a peroxide, catalyze the dimerization of phenolic compounds. Thus, in some embodiments, peroxidase catalyzed activation forms a putative free radical tyramine derivative that will covalently bind to other phenol moieties, thereby covalently binding the tyramine, or tyramine derivative, residue to a solid phase. The solid phase may be, for example, protein components of cells or cellular structures that are immobilized on a substrate such as a microscope slide. Thus, if tyramine is added to a protein-containing sample in the presence of horseradish peroxidase and peroxide (e.g., hydrogen peroxide), the tyramine phenol group can form a dimer with the phenol moiety of a tyrosine amino acid. It is desirable, however, to specifically bind the tyramine at, or in close proximity to, a desired target with the sample. This objective can be achieved by immobilizing the enzyme on a target in the sample, as described herein.

Tyramine molecules activated by the immobilized enzyme will react and form dimers with phenol moieties (e.g., tyrosine residues or another tyramine moiety) proximal to the immobilized enzyme. For example, studies indicate that most activated tyramine molecules are deposited within 10 nm of the activating peroxidase, with rapid reduction in the number of molecules deposited past the 10 nm radius from the point that they were generated (Bendayan and Meyer, *J. Histo Chem. Cytochem.*, 421-429, 1999). Thus, in some embodiments, the activated tyramine (or tyramide conjugate) is deposited proximal to the immobilized enzyme, such as within about 50 nm, within 40 nm, within 30 nm within 20 nm, within 10 nm, or within 5 nm of the immobilized enzyme.

Suitable conditions for TSA as well as reagents and kits for use for TSA are known to a person of ordinary skill in the art (see, e.g., Bobrow et al, *J. Immuno. Meth.*, 125:279-285, 1989; AmpMap Detection Kit with TSA™, Cat. No. 760-121, Ventana Medical Systems, Inc., Tucson, Ariz.). For example, suitable conditions include a reaction buffer, or solution, that includes a peroxide (e.g., hydrogen peroxide), and has a salt concentration and pH that enable the enzyme to perform its desired function. The reaction is performed at a temperature that is suitable for the enzyme. For example, if the enzyme is horseradish peroxidase, the reaction may be performed at 35-40° C. Under such conditions, the tyramide reacts with the peroxide and the enzyme, converting the tyramide to an active form that covalently binds to phenol moieties in the sample. While the working examples use tyramide conjugates as enzyme substrates for amplification, other enzyme catalyzed reactive species may be substituted without loss of efficacy. In substituting other enzyme-catalyzed reactive species, the reactivity of the generated species is of particular importance. In particular, species with lower reactivities permit greater diffusion prior to reaction, thus resulting in a larger region which may be considered as proximal. Likewise, species with higher reactivities may react more closely to the target.

VI. Automated Method

Certain disclosed embodiments of the present invention are particularly adapted for use with automated staining platforms, and particularly automated staining platforms that dispense reagents in a series of steps to formalin fixed paraffin embedded tissue samples. For example, certain of the disclosed embodiments are particularly useful in combination with BenchMark® XT staining platform available from Ventana Medical Systems, Inc., the assignee of the present application. More specifically, the automated staining protocols are intended for use with the current BenchMark® XT IHC/ISH Staining Module. Information concerning automated staining platforms from Ventana Medical Systems, Inc. can be found in U.S. Pat. Nos. 7,410,753 and 7,615,371. These patents are incorporated herein by reference to provide information concerning using automated systems to practice embodiments of staining protocols, such as the biotinylation embodiments described herein.

One exemplary automated protocol for the BenchMark® XT staining platform utilized an anti-antibody:biotin ligase conjugate, such as a goat anti-rabbit-biotin ligase conjugate, and an anti-hapten:BTS conjugate, such as an anti-benzofurazan-BTS substrate. TSA amplification also was employed using a tyramide-benzofurazan conjugate. The automated steps were as follows: 1. Start Timed Steps, 2. Select EZ Prep, 3. Extra RB washes added; LCS depar, TSA start twice; 2nd TSA blocker washed, 4. Warmup Slide to 60° C., 5. Apply Coverslip, 6. Incubate for 4 Minutes, 7. Apply EZPrep Volume Adjust, 8. Warmup Slide to 75° C., and Incubate for 4 Minutes, 9. Rinse Slide, 10. Apply Coverslip, 11. Incubate for 4 Minutes, 12. Apply EZPrep Volume Adjust. 13. Warmup Slide to 75° C., and Incubate for 4 Minutes, 14 Rinse Slide, 15. Apply Coverslip, 16. Incubate for 4 Minutes, 17. Apply EZPrep Volume Adjust, 18. Warmup Slide to 75° C., and Incubate for 4 Minutes, 19. Rinse Slide, 20. Apply Depar Volume Adjust, 21. Apply Coverslip, 22. Disable Slide Heater, 23. Short—8 Minute Conditioning, 24. Rinse Slide, 25. Apply Long Cell Conditioner #1, 26. Apply CC Coverslip Long, 27. Select SSC Wash, 28. Warmup Slide to 95° C., and Incubate for 8 Minutes, 29. Mild—30 Minute Conditioning, 30. Apply Cell Conditioner #1, 31. Apply CC Medium Coverslip No BB, 32. Warmup Slide to 100° C., and Incubate for 4 Minutes, 33. Apply CC Medium Coverslip No BB, 34. Apply Cell Conditioner #1, 35. Apply CC Medium Coverslip No BB, 36. Apply Cell Conditioner #1, 37. Apply CC Medium Coverslip No BB, 38. Apply Cell Conditioner #1, 39. Apply CC Medium Coverslip No BB, 40. Apply Cell Conditioner #1, 41. Apply CC Medium Coverslip No BB, 42. Apply Cell Conditioner #1, 43. Apply CC Medium Coverslip No BB, 44. Standard—60 Minute Conditioning, 45. Apply Cell Conditioner #1, 46. Apply CC Medium Coverslip No BB, 47. Apply Cell Conditioner #1, 48. Apply CC Medium Coverslip No BB, 49. Apply Cell Conditioner #1, 50. Apply CC Medium Coverslip No BB, 51. Apply Cell Conditioner #1, 52. Apply CC Medium Coverslip No BB, 53. Apply Cell Conditioner #1, 54. Apply CC Medium Coverslip No BB, 55. Apply Short Cell Conditioner #1, 56. Apply CC Medium Coverslip No BB, 57. Apply Cell Conditioner #1, 58. Apply CC Medium Coverslip No BB, 59. Disable Slide Heater, 60. Incubate for 8 Minutes, 61. Rinse Slide With Reaction Buffer, 62. Adjust Slide Volume With Reaction Buffer, 63. Apply Coverslip, 64. Rinse Slide With Reaction Buffer, 65. Adjust Slide Volume With Reaction Buffer, 66. Apply Coverslip, 67. Warmup Slide to 37° C., and Incubate for 4 Minutes, 68. Apply One Drop of UV INHIBITOR, and Incubate for 8 Minutes, 69. Rinse Slide With Reaction Buffer, 70. Adjust Slide Volume With Reaction Buffer, 71. Apply Coverslip, 72. Rinse Slide With Reaction Buffer, 73. Adjust Slide Volume With Reaction Buffer, 74. Apply One Drop of Streptavidin at 100 mg/L to block endogenous biotin on tissue, Apply Coverslip, and Incubate for [32 Minutes], 75. Rinse Slide With Reaction Buffer, 76. Adjust Slide Volume With Reaction Buffer, 77. Apply Coverslip, 78. Warmup Slide to 37° C., and Incubate for 4 Minutes, 79. Rinse Slide With Reaction Buffer, 80. Adjust Slide Volume With Reaction Buffer, 81. Apply Coverslip, 82. Titration with primary antibodies that bind to targets, and Incubate for 32 Minutes, 83. Rinse Slide With Reaction Buffer, 84. Adjust Slide Volume With Reaction Buffer, 85. Apply Coverslip, 86. Rinse Slide With Reaction Buffer, 87. Adjust Slide Volume With Reaction Buffer, 88. Apply Coverslip, 89. Use GAM-HRP for Tyramide Hapten#1, 90. Rinse Slide With Reaction Buffer, 91. Adjust Slide Volume With Reaction Buffer, 92. Apply Coverslip, 93. Rinse Slide With Reaction Buffer, 94. Adjust Slide Volume With Reaction Buffer, 95. Ab here is GAM-HRP for TSA, 96. Apply One Drop of [ANTIBODY 6] (DS Antibody), Apply Coverslip, and Incubate for 16 Minutes, 97. Rinse Slide With Reaction Buffer, 98. Apply 900 ul of Reaction Buffer, 99. Apply Coverslip, 100. Rinse Slide With Reaction Buffer, 101. Adjust Slide Volume With Reaction Buffer, 102. Apply Coverslip. 103. Rinse Slide With Reaction Buffer, 104. Adjust Slide Volume With Reaction Buffer, 105. Apply Coverslip, 106. Rinse Slide With Reaction Buffer, 107. Adjust Slide Volume With Reaction Buffer, 108. Options 2 and 3<- -> Ty-Fluo/Hapten+H2O2 here, 109. Apply One Drop of a tyramide-hapten conjugate e.g. Tyramide-BF, Apply Coverslip, and Incubate for 4 Minutes, 110. Apply One Drop of H2O2 for tyramide reaction, and Incubate for 16 Min, 111. Rinse Slide With Reaction Buffer, 112. Apply 900 ul of Reaction Buffer, 113. Apply Coverslip, 114. Rinse Slide With Reaction Buffer, 115. Adjust Slide Volume With Reaction Buffer, 116. Apply Coverslip, 117. Rinse Slide With Reaction Buffer, 118. Adjust Slide Volume With Reaction Buffer, 119. Apply Coverslip, 120. Kill GAM-HRP if use DAB detection, do not select if AP detection without 2nd TSA, 121. GAR-HRP for TSA hapten #2, 122. If Research Fork 1 is selected, hand apply reagent, 123. Rinse Slide With Reaction Buffer, 124. Adjust Slide Volume With Reaction Buffer, 125. Apply Coverslip, 126. Warmup Slide to 37° C., and Incubate for 4 Minutes, 127. Titration of biotin ligase conjugate and BTS conjugate, e.g. anti-BF-BTS and goat anti rabbit-biotin ligase, and Incubate for 32 Minutes, 128. Rinse Slide With Reaction Buffer, 129. Adjust Slide Volume With Reaction Buffer, 130. Apply Coverslip, 131. Rinse Slide With Reaction Buffer, 132. Adjust Slide Volume With Reaction Buffer, 133. Apply Coverslip, 134. If Research Fork #2 selected, hand apply reagent, 135. If Research Fork #3 selected, hand apply reagent, long incubation time, 136. Rinse Slide With Reaction Buffer, 137. Adjust Slide Volume With Reaction Buffer, 138. Apply Coverslip, 139. Warmup Slide to 37° C., and Incubate for 4 Minutes, 140. Titration of biotin ligase enzymatic reaction buffer onto the tissue slide, which contains buffer, ATP, and biotin, and Incubate for 1 Hour, 141. Rinse Slide With Reaction Buffer, 142. Apply 900 ul of Reaction Buffer, 143. Apply Coverslip, 144. Rinse Slide With Reaction Buffer, 145. Adjust Slide Volume With Reaction Buffer, 146. Apply Coverslip, 147. Rinse Slide With Reaction Buffer, 148. Adjust Slide Volume With Reaction Buffer, 149. Apply Coverslip, 150. If Research Fork #4 selected, hand apply reagent, 151. If Research Fork #5 selected, hand apply reagent Gly/SDS 50C, 152. If Research Fork #6 selected, dispense Option 6 or hand apply, 153. Warmup Slide to 37° C., and Incubate for 4 Minutes, 154. Rinse Slide With Reaction Buffer, 155. Adjust Slide Volume With Reaction Buffer, 156. Option 6 is the SAv-HRP or SAv-AP, 157. Option 6 incubation time, 158. Apply One Drop of OPTION 6, Apply Coverslip, and Incubate for 0 Hr 24 Min, 159. Rinse Slide With Reaction Buffer, 160. Apply 900 ul of Reaction Buffer, 161. Apply Coverslip, 162. Rinse Slide With Reaction Buffer, 163. Adjust Slide Volume With Reaction Buffer, 164. Apply Coverslip, 165. If Research Fork #7 selected, hand apply reagent, 166. AP Red Detection, 167. Rinse Slide With Reaction Buffer, 168. Adjust Slide Volume With Reaction Buffer, 169. Apply One Drop of UV Red Enhancer, Apply Coverslip, and Incubate for 4 Minutes, 170. Apply One Drop of UV Fast Red A and One Drop of UV Red Naphthol, and Incubate for 8 Minutes, 171. Apply One Drop of UV Fast Red B, and Incubate for 8 Minutes, 172. Rinse Slide With Reaction Buffer, 173. Adjust Slide Volume With Reaction Buffer, 174. Apply Coverslip, 175. Rinse Slide With Reaction Buffer, 176. Adjust Slide Volume With Reaction Buffer, 177. Apply One Drop of HEMATOXYLIN II (Counterstain), Apply Coverslip, and Incubate for 4 Minutes, 178. Rinse Slide With Reaction Buffer, 179. Adjust Slide Volume With Reaction Buffer, 180. Apply Coverslip, 181. Rinse Slide With Reaction Buffer, 182. Adjust Slide Volume With Reaction Buffer, 183. Apply One Drop of [BLUING REAGENT] (Post Counterstain), Apply Coverslip, and Incubate for 4 Minutes, 184. Rinse Slide With Reaction Buffer, 185. Adjust Slide Volume With Reaction Buffer, 186. Apply Coverslip, 187. Disable Slide Heater, 188. Mixers Off, 189. Rinse Slide With Reaction Buffer, 190. Jet Drain With Reaction Buffer, 191. Rinse Slide With Reaction Buffer, 192. Adjust Slide Volume With Reaction Buffer, 193. Apply Coverslip.

Accordingly, a method for analyzing a sample to determine whether a first target is proximal to a second target comprises labeling the first target with a biotin ligase, labeling the second target with a biotin ligase substrate, contacting the sample with biotin and ATP so that the biotin ligase biotinylates the biotin ligase substrate if the first target is proximal to the second target; detecting the biotin if the first target is proximal to the second target. In one embodiment, labeling the first target includes contacting the sample with a first primary antibody specific to the first target and labeling the second target includes contacting the sample with a second primary antibody specific to the second target. In another embodiment, the first primary antibody is labeled with a first hapten and labeling the first target includes contacting the sample with a first secondary antibody specific to the first hapten. In another embodiment, the second primary antibody is labeled with a second hapten and labeling the second target includes contacting the sample with a second secondary antibody specific to the second hapten. In yet another embodiment, the first primary antibody is derived from a first species and labeling the first target includes contacting the sample with a first secondary anti-species antibody specific to the first species. In another embodiment, the second primary antibody is derived a first species and labeling the second target includes contacting the sample with a second secondary anti-species antibody specific to the second species. In one embodiment, labeling the first target includes contacting the sample with a first amplification reagent selected from a tyramide conjugate or a quinone methide precursor conjugate. In another embodiment, labeling the second target includes contacting the sample with an amplification reagent selected from a tyramide conjugate or a quinone methide precursor conjugate.

In further illustrative embodiments, the first target and the second target are dimerized proteins. In one embodiment, the first target is a first nucleic acid target, wherein labeling the first target comprises contacting the sample with a first nucleic acid probe. In another embodiment, the second target is a second nucleic acid target, wherein labeling the second target comprises contacting the sample with a second nucleic acid probe. In another embodiment, the first nucleic acid probe is labeled with a third hapten, wherein labeling the first target comprises contacting the sample with a third secondary antibody specific to the third hapten. In yet another embodiment, detecting the biotin comprises contacting the sample with a conjugate comprising a streptavidin or avidin conjugated to one or more enzymes. In another embodiment, detecting the biotin comprises contacting the sample with a chromogen. In one embodiment, detecting the biotin comprising contacting the sample with an amplification reagent selected from a tyramide conjugate or a quinone methide precursor conjugate. In another embodiment, the sample is a formalin fixed paraffin embedded tissue. In another embodiment, the first target is proximal to a second target if is less than about 100 nm, less than about 50 nm, less than about 20 nm apart, less than about 10 nm, less than about 5 nm, or less than about 2 nm apart.

In further illustrative embodiments, an automated method comprises using an automated staining apparatus to perform one or more steps associated with a method of testing a formalin fixed paraffin embedded tissue sample for the presence of a first target and a second target in close proximity. The method includes contacting the sample with a first set of reagents so that the first target is recognized by a first specific binding moiety and that results in the conjugation or deposition of a biotin ligase proximally to the first target; contacting the sample with a second set of reagents so that the second target is recognized by a second specific binding moiety and that results in the conjugation or deposition of a biotin ligase substrate proximally to the second target; contacting the sample with biotin and biotinylation reagents so that the biotin ligase biotinylates the biotin ligase substrate if the first target and the second target are in close proximity; and detecting the biotin. In another embodiment, the method includes administering a therapeutic to the subject according to whether the first target and the second target are proximal.

VII. Method for Treating a Subject

Further embodiments include a method of treating a subject with a tumor expressing a protein complex as determined using disclosed embodiments of the present invention. In general, the method comprised using a disclosed embodiment of a detection method to detect the occurrence of a first target located proximal to, forming a dimer with, or otherwise in close spatial relationship to, a second target. The positive result associated with the detection methodology is an indication that a subject is a candidate for treatment with known or hereafter developed therapeutics for the particular malady.

For example, the method may be exemplified with reference to a first HER protein and a second HER protein. The method comprises selecting a subject with a tumor expressing a protein complex including a first HER protein and a second HER protein as determined according to disclosed embodiments of the present invention. A therapeutically effective amount of an agent that disrupts the HER protein complex is administered to the subject, wherein disruption of the HER protein complex treats the tumor in the subject. In some such embodiments, the first HER protein is HER2 and the second HER protein is HER2 and the agent comprises trastuzumab. In some embodiments, the first HER protein is HER3 and the second HER protein is HER2 or the first HER protein is HER2 and the second HER protein is HER3 and the agent comprises pertuzumab. In some embodiments, the first HER protein is p95 or the second HER protein is p95 and the agent comprises a chemotherapeutic agent.

VIII. Kits

Certain disclosed embodiments concern kits having at least one conjugate, reagent, buffer solution, staining reagents, etc. useful for practicing disclosed embodiments of the present invention. For example, one embodiment of a disclosed kit comprises at least one conjugate selected from a first conjugate comprising biotin ligase and a specific binding moiety and a second conjugate comprising a biotin ligase substrate and a specific binding moiety. For certain embodiments the specific binding moiety is an antibody; the biotin ligase is from BirA; and/or the substrate is BTS. The kit may further include biotin and ATP. Staining reagents also may be included, such as streptavidin; a streptavidin:enzyme conjugate, such as a streptavidin:horseradish peroxidase conjugate or a streptavidin:alkaline phosphatase; diaminobenzidine and hydrogen peroxide; and/or alkaline phosphatase red.

IX. Working Examples

The following examples are provided to illustrate certain features of working embodiments of the disclosed invention. A person of ordinary skill in the art will appreciate that the invention is not limited to those features exemplified by these working embodiments.

Example 1: Biotin Ligase Protein Expression

Biotin ligase gene from *E. coli* was amplified by PCR (Phusion Hot Start II High-Fidelity DNA Polymerase, Thermo Scientific) with DNA template from plasmid pBIOTIN LIGASEcm (note any *E. coli* genomic DNA will serve the same purpose because biotin ligase is an essential gene). The 5' primer sequence used was SEQ. ID. No. 1 which incorporated the sequences for a poly-histidine tag, followed by a disulfide bridge (CSNLSTCVL) from salmon calcitonin. The poly-histidine tag facilitates biotin ligase purification by metal affinity purification and the disulfide bridge is used for chemical conjugation to antibodies. The 3' primer sequence used was SEQ. ID. No. 2.

The PCR fragment was purified from 1% agarose gel (Qiagen Gel Extraction Kit) and cloned into Ptac based expression vector pJExpress 404 (DNA 2.0) and DNA sequence was verified by sequencing (Eurofin/Operon). The verified plasmid construct was transformed in *E. coli* 5-alpha F'I$^q$ competent cells (New England Biolabs) for protein expression. All *E. coli* strains were grown in Terrific Broth supplemented with 100 mg/mL ampicillin (Sigma). Expression of biotin ligase was induced with 0.5 mM isopropyl β-D-1-thiogalactopyranoside (IPTG) (Sigma) when overnight subculture reaches $A_{260}$ around 0.5 and induction proceeds for 4 to 5 hours at 37° C. Culture media were centrifuged at 4000 g for 10 minutes and cell pellets were stored at −80° C. Purification of biotin ligase on Ni-NTA column followed the instructions from manufacturer (Thermo Scientific HisPur Ni-NTA Spin Columns, 3 mL). Typical yield of biotin ligase from 1 liter culture was about 25 mg. Ni-NTA column purified biotin ligase was further purified on GE AKTA FPLC with Superdex 200 HR 10/30 25 cm column and fractions were collected and run on 10% PAGE gel, and fractions with expected size of 35 KDa were pooled and concentrated with Vivaspin sample concentrator (GE Healthcare Life Science) with molecular cutoff of 10 KDa.

Example 2: Biotin Ligase Activity Assay

Biotin ligase substrate target peptide sequence (BTS) HYNIC-GGSGLNDIFEAQKIEWHE-COOH, was synthesized by Biosynthesis Inc. (Lewisville, Tex.) with HyNic moiety at the N-terminus.

A mixture of 20 nM biotin ligase and BTS (10 μM) in 100 uL of biotin ligase reaction buffer (0.1 M KCl, 5.5 mM $MgCl_2$, 50 mM Tris.HCl (pH=8.0), 0.05% Brij-35, 0.1 mM dithiothreitol (DTT), 3 mM ATP, and 60 μM biotin) was incubated at 37° C. for 20 to 60 minutes. 10 μL of reaction mixture aliquot was purified using ZipTip (Millipore) following standard procedure and the purified peptide was eluted with CHCA (10 mg/mL in acetonitrile/water). MALDI analysis was performed using a Bruker Autoflex III MALDI-TOF spectrometer in positive ion mode.

The molecular weight of un-modified peptide substrate BTS is 2205 and the product of the biotinylated peptide BTS-biotin is 2431 (Mw of biotin is 244).

To further confirm that the peptide was indeed biotinylated, after 1 hour incubation Streptavidin coated magnetic beads (Pierce) were added to the reaction mixture. After incubation and separation of the beads, the supernatant was analyzed by MALDI-TOF as previously described. The absence of BTS-biotin peak (Mw=2431) further confirmed the biotinylation of BTS.

Biotin ligase activity in biotin ligase-antibody conjugates was analyzed following the same protocol.

Example 3: Synthesis of Goat Anti Rabbit (GAR) Biotin Ligase Conjugate

One embodiment of a method for making a goat anti-rabbit biotin ligase conjugate is shown below in Scheme 1.

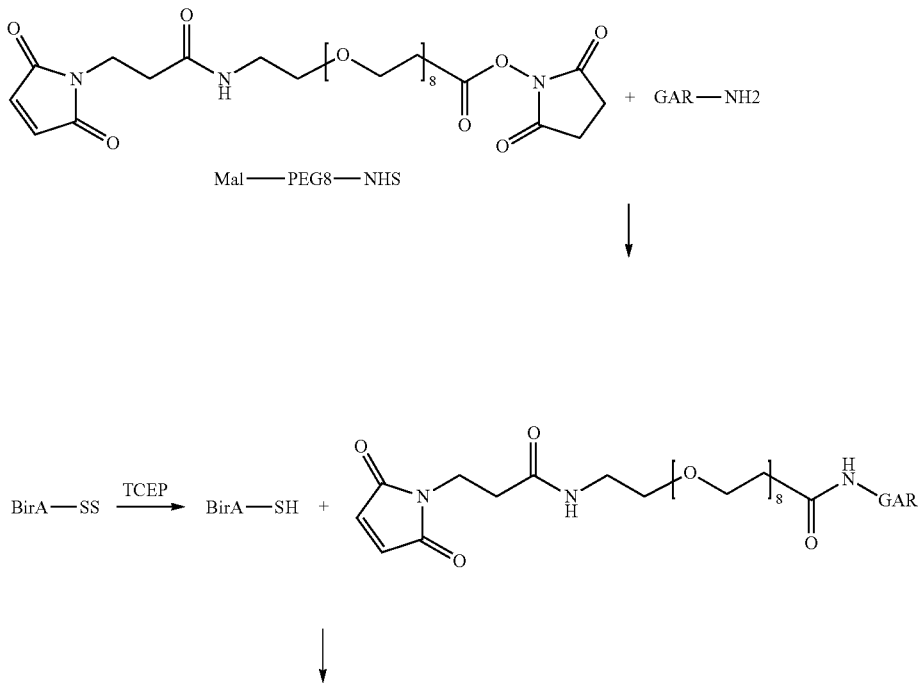

Scheme 1

-continued

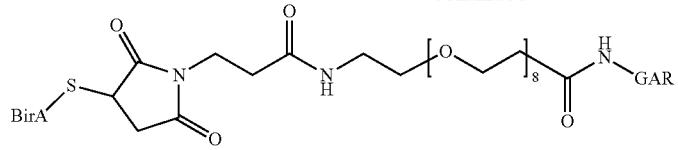

1 mg of GAR was diluted in 400 μL of PBS (100 mM phosphate, pH=7.2) to give a concentration of 2.5 mg/mL. To this solution was added MAL-PEG8-NHS in DMSO (10 mM stock) (15 or 30 equivalents to GAR) and incubated at room temperature for two hours. Meanwhile, 1 mg of biotin ligase-SS (3 equivalents to GAR) was reduced using tris(2-carboxyethyl)phosphine (TCEP) (1.5 equivalents to biotin ligase) at room temperature for two hours. Both modified proteins were purified using Zeba Spin Desalting Columns (Pierce, 7K MWCO, 2 mL), following manufactory instruction. The proteins were eluted in PBS (0.1 M, pH=6.5 with 1 mM EDTA). The purified proteins were combined and incubated at room temperature overnight. The conjugate was purified on GE AKTA FPLC using Superdex 200 HR 10/30 gel. Protein was eluted using PBS (10 mM phosphate, pH=7.4). The biotin ligase activity in the conjugate was analyzed using the protocol in Example 2, with a reaction incubation time of 60 minutes.

Example 4: Synthesis of Mouse Anti NP (MsxNP) Biotin Ligase Conjugate

The conjugate was synthesized using the method from Example 3, with the following molar ratios: MAL-PEG8-NHS/MsxNP 10/1; TCEP/biotin ligase 1.5/1; biotin ligase/MsxNP 3/1. The enzyme was purified on GE AKTA FPLC using Superdex 200 HR 10/30 gel. Protein was eluted using PBS (10 mM phosphate, pH=7.4). The biotin ligase activity in the conjugate was analyzed using the protocol in Example 2, with a reaction incubation time of 60 minutes.

Example 5: Synthesis of MsxNP Biotin Ligase Conjugate Using Hydrazine Chemistry

The synthesis strategy for making a MsxNP biotin ligase conjugate is illustrated below in Scheme 2.

Scheme 2

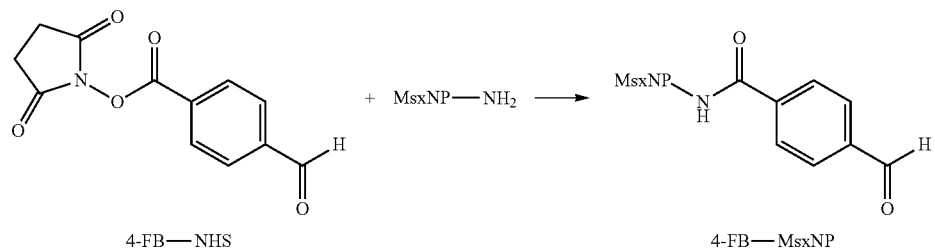

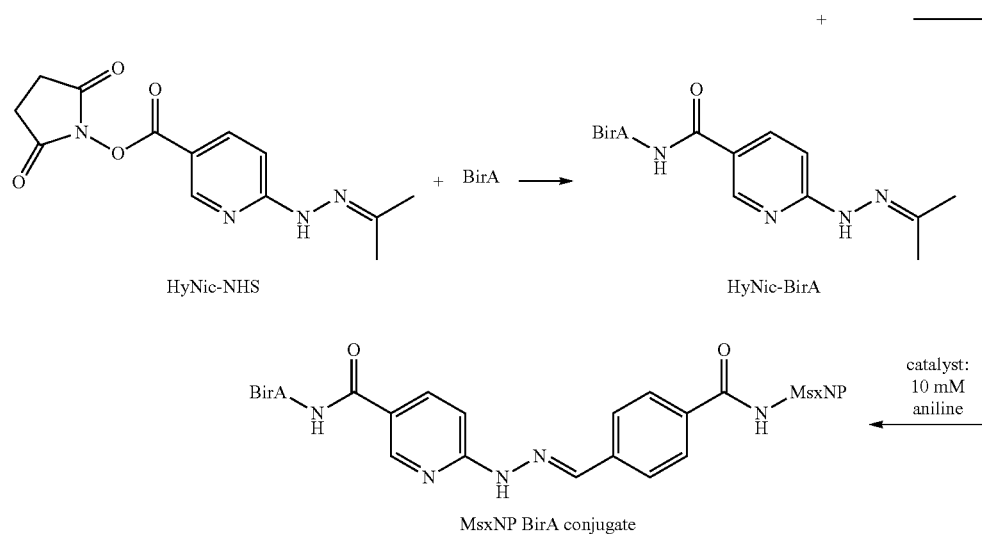

1 mg of MsxNP was diluted in 400 μL of PBS (100 mM phosphate, pH 7.2) to give a concentration of 2.5 mg/mL. To this solution, 5 equivalents of 4FB-NHS (Solulink) in DMSO (10 mM stock) was added and incubated at room temperature for two hours. Meanwhile, biotin ligase (3 equivalents to MsxNP) was activated using S-HyNic (3 equivalents to biotin ligase) at room temperature for two hours. Both modified proteins were purified using Zeba Spin Desalting Columns (Pierce, 7K MWCO, 2 mL), following manufactory instruction. The proteins were eluted in PBS (0.1 M, pH=6.5 with 1 mM EDTA). The purified proteins were combined and incubated at room temperature overnight, with 10 mM aniline added as a catalyst. The conjugate was purified on GE AKTA FPLC using Superdex 200 HR 10/30 gel. Protein was eluted using PBS (10 mM phosphate, pH=7.4). The biotin ligase activity in the conjugate was analyzed using the protocol in Example 2, with a reaction incubation time of 60 minutes.

Example 6: Chemical Conjugation of Biotin Ligase Target Sequence (BTS) to Antibodies One embodiment of a method for making a BTS antibody conjugate is illustrated below in Scheme 3.

purified by using a VIVASPIN filter (GE) with MWCO=50 KDa. Five rounds of wash using PBS (0.1 M, pH=7.2) were performed and the conjugate was collected. The ratio of BTS to antibody was determined by measuring the absorbance of 280 nm (GAR) and 350 nm (hydrazone bond formed from 4FB-HyNic reaction). Typically, 2-5 BTS per GAR was achieved.

Example 7: Chemical Conjugation of Goat Anti Mouse (GAM)-BTS 0.25 mg of GAM at ~2 mg/mL in 0.1 M PBS (pH=7.2) was added 4FB-PEG4-PFP active ester (Solulink S-1034) (15 equivalents to GAM) from a 10 mM stock solution in DMSO. The mixture was incubated at room temperature for 2 hours and the 4FB modified GAM was purified using a Zeba spin column (Pierce), buffer exchanged to PBS (0.1 M, pH=6). HyNic labeled BTS (from Biosynthesis, Inc.) (10 equivalents) was added to the purified 4FB-GAM and incubated at room temperature overnight. The conjugate was purified by using a VIVASPIN filter (GE) with MWCO=50 KDa. Five rounds of wash using PBS (0.1 M, pH=7.2) were performed and the conjugate was collected. The ratio of BTS to antibody was determined by measuring the absorbance of

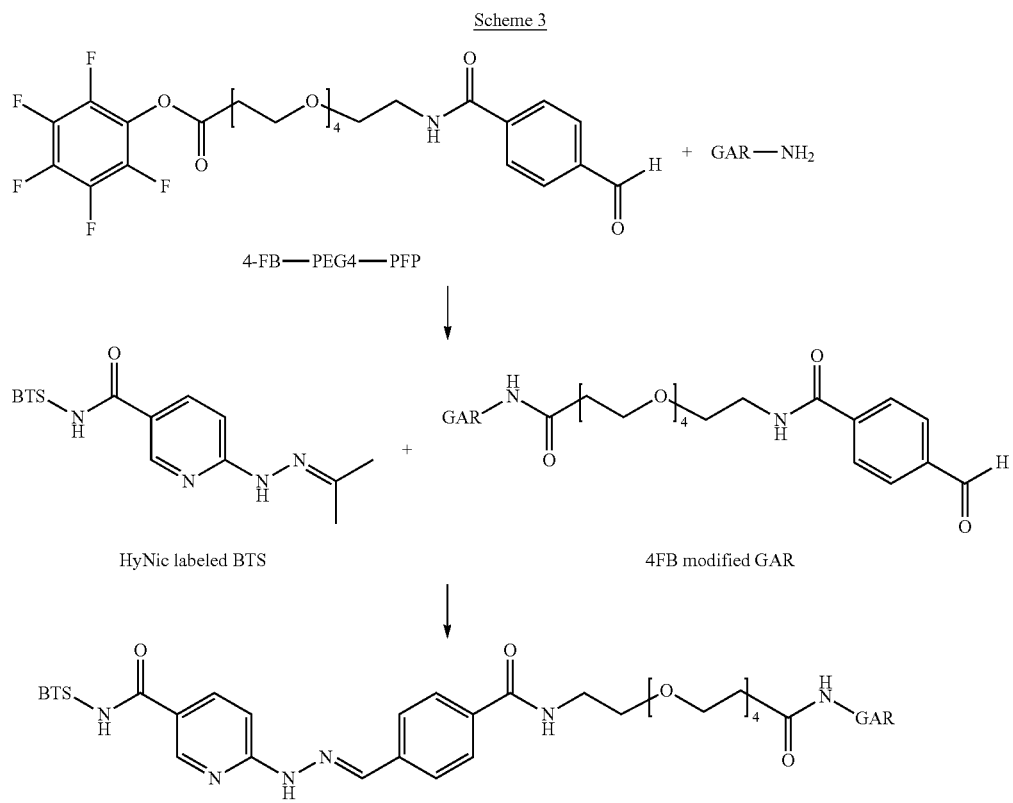

0.25 mg of GAR at ~2 mg/mL in 0.1 M PBS (pH=7.2) was added 4FB-PEG4-PFP active ester (Solulink S-1034) (15 equivalents to GAR) from a 10 mM stock solution in DMSO. The mixture was incubated at room temperature for 2 hours and the 4FB modified GAR was purified using a Zeba spin column (Pierce), buffer exchanged to PBS (0.1 M, pH=6). HyNic labeled BTS (from Biosynthesis, Inc.) (10 equivalents) was added to the purified 4FB-GAR and incubated at room temperature overnight. The conjugate was 280 nm (GAM) and 350 nm (hydrazone bond formed from 4FB-HyNic reaction). Typically, 2-5 BTS per GAM was achieved.

Example 8: Chemical Conjugation of MsxBF-BTS 0.25 mg of MsxBF at ~2 mg/mL in 0.1 M PBS (pH=7.2) was added 4FB-PEG4-PFP active ester (Solulink S-1034) (15 equivalents to MsxBF) from a 10 mM stock solution in DMSO. The mixture was incubated at room temperature for 2 hours and the 4FB modified MsxBF was purified using a Zeba spin column (Pierce), buffer exchanged to PBS (0.1 M, pH=6). HyNic labeled BTS (from Biosynthesis, Inc.) (10 equivalents) was added to the purified 4FB-MsxBF and incubated at room temperature overnight. The conjugate was purified by using a VIVASPIN filter (GE) with MWCO=50 KDa. Five rounds of wash using PBS (0.1 M, pH=7.2) were performed and the conjugate was collected. The ratio of BTS to antibody was determined by measuring the absorbance of 280 nm (MsxBF) and 350 nm (hydrazone bond formed from 4FB-HyNic reaction). Typically, 2-5 BTS per MsxBF was achieved.

Example 9: Chemical Conjugation of MsxNP-BTS 0.25 mg of MsxNP at ~2 mg/mL in 0.1 M PBS (pH=7.2) was added 4FB-PEG4-PFP active ester (Solulink S-1034) (15 equivalents to MsxNP) from a 10 mM stock solution in DMSO. The mixture was incubated at room temperature for 2 hours and the 4FB modified MsxNP was purified using a Zeba spin column (Pierce), buffer exchanged to PBS (0.1 M, pH=6). HyNic labeled BTS (from Biosynthesis, Inc.) (10 equivalents) was added to the purified 4FB-MsxNP and incubated at room temperature overnight. The conjugate was purified by using a VIVASPIN filter (GE) with MWCO=50 KDa. Five rounds of wash using PBS (0.1 M, pH=7.2) were performed and the conjugate was collected. The ratio of BTS to antibody was determined by measuring the absorbance of 280 nm (MsxNP) and 350 nm (hydrazone bond formed from 4FB-HyNic reaction). Typically, 2-5 BTS per MsxNP was achieved.

Example 10: Synthesis of Dual-Hapten-Labeled BSA (Dig/DNP-BSA)

5 equivalents of Dig-NHS (Roche), 5 equivalents of DNP-PEG8-NHS (Quanta Biodesign) and 5 equivalents of MAL-PEG8-MAL (Quanta) was added to 30 μL of 1 mg/mL solution of BSA in 0.1 PBS (pH=7.2) (30 μg of BSA). The reaction was incubated at room temperature for 2 hours and the modified BSA was purified using Zeba mini spin columns, buffer exchanged to PBS (pH=6.5, with 1 mM EDTA).

Example 11: Synthesis of Dig-Labeled BSA (Dig-BSA)

10 equivalents of Dig-NHS (Roche) and 5 equivalents of MAL-PEG8-MAL (Quanta) was added to 30 μL of 1 mg/mL solution of BSA in 0.1 PBS (pH=7.2) (30 μg of BSA). The reaction was incubated at room temperature for 2 hours and the modified BSA was purified using Zeba mini spin columns, buffer exchanged to PBS (pH=6.5, with 1 mM EDTA).

Example 12: Synthesis of DNP-Labeled BSA (DNP-BSA)

10 equivalents of DNP-PEG8-NHS (Quanta Biodesign) and 5 equivalents of MAL-PEG8-MAL (Quanta) was added to 30 μL of 1 mg/mL solution of BSA in 0.1 PBS (pH=7.2) (30 μg of BSA). The reaction was incubated at room temperature for 2 hours and the modified BSA was purified using Zeba mini spin columns, buffer exchanged to PBS (pH=6.5, with 1 mM EDTA).

Example 13: Introducing Thiol Groups on Tissue

FFPE Placenta tissue slides were de-paraffinized and antigen retrieved using standard CC1 condition on a Benchmark XT (Ventana). Eight non-contacting tissue sections on each slide were created by removal of portions of the tissue by using a razor blade. The slides were then treated with 3 mg/mL of Traut's reagents (Pierce) in 0.1 M PBS (pH=7.2) for 1 hour to convert amino groups on tissue to thiols. The slides were thoroughly washed with water and briefly dried under a nitrogen stream. The thiolated slides were used immediately.

Example 14: Crosslinking of BSA to Thiolated Tissue

Four BSA concentrations (4 μM, 2 μM, 1 μM, and 0.5 μM) were used, either with the dual-labeled BSA or a 1:1 mixture of the mono-hapten labeled BSA. For all concentrations, 0.5 mg/mL of un-modified BSA was added to inhibit non-specific binding. To each tissue section was then added 3 ml of the BSA solution. To the four sections in the left column was added dual-labeled BSA of the four concentrations and labeled as "D". To the four sections in the right column was added mixture of the mono-labeled BSA of the four total concentrations and labeled as "M". The slide was placed in a humidity box and incubated at room temperature for 4 hours. The slide was rinsed thoroughly with water and the free residual thiol groups on the tissue were quenched by adding 1 mL of 40 mM N-ethyl-maleimide in 0.1 M PBS (pH=6.5) followed by incubation for 15 minutes. The slide was rinsed thoroughly with water to remove any unbound molecules.

The modified slide was stained on a Benchmark XT (Ventana) with MsxDig+RbxDNP as primary antibody, GAM-BTS and GAR-biotin ligase as secondary antibody, followed by addition of biotin and ATP for enzymatic reaction. The biotinylation was detected by streptavidin-HRP and DAB staining.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims

The invention claimed is:

1. A method for analyzing a sample to determine whether a first target is proximal to a second target, the method comprising:
   contacting a sample with a first conjugate comprising a biotin ligase and a first binding moiety specific for the first target;
   contacting the sample with a second conjugate comprising a biotin ligase peptide substrate and a second binding moiety specific for the second target;
   contacting the sample with biotin and ATP so that the biotin ligase labels the biotin ligase peptide substrate with biotin if the first target is proximal to the second target; and
   detecting the biotin label;
   wherein the first and second binding moieties are selected from an antibody, an antibody fragment, or an antibody derivative or an antibody mimetic.

2. The method according to claim 1, wherein labeling the first target includes contacting the sample with a first primary antibody specific to the first target and labeling the second target includes contacting the sample with a second primary antibody specific to the second target.

3. The method according to claim 2, wherein the first primary antibody is labeled with a first hapten and labeling the first target includes contacting the sample with a first secondary antibody specific to the first hapten.

4. The method according to claim 3, wherein the second primary antibody is labeled with a second hapten and labeling the second target includes contacting the sample with a second secondary antibody specific to the second hapten.

5. The method according to claim 2, wherein the first primary antibody is derived from a first species and labeling the first target includes contacting the sample with a first secondary anti-species antibody specific to the first species.

6. The method according to claim 5, wherein the second primary antibody is derived a second species and labeling the second target includes contacting the sample with a second secondary anti-species antibody specific to the second species.

7. The method according to claim 2, wherein labeling the first target includes contacting the sample with a first amplification reagent selected from a tyramide conjugate or a quinone methide precursor conjugate.

8. The method according to claim 2, wherein labeling the second target includes contacting the sample with an amplification reagent selected from a tyramide conjugate or a quinone methide precursor conjugate.

9. The method of according to claim 1, wherein the first target and the second target are dimerized proteins.

10. The method of according to claim 1, wherein the first target is a first nucleic acid target, wherein labeling the first target comprises contacting the sample with a first nucleic acid probe.

11. The method according to claim 10, wherein the second target is a second nucleic acid target, wherein labeling the second target comprises contacting the sample with a second nucleic acid probe.

12. The method according to claim 10, wherein the first nucleic acid probe is labeled with a third hapten, wherein labeling the first target comprises contacting the sample with a third secondary antibody specific to the third hapten.

13. The method of according to claim 1, wherein detecting the biotin comprises contacting the sample with a conjugate comprising a biotin binding antibody, avidin, or streptavidin conjugated to one or more enzymes.

14. The method of claim 13, wherein detecting the biotin comprises contacting the sample with a chromogen.

15. The method of according to claim 1, wherein detecting the biotin comprising contacting the sample with an amplification reagent selected from a tyramide conjugate or a quinone methide precursor conjugate.

16. The method of according to claim 1, wherein the sample is a formalin fixed paraffin embedded tissue.

17. The method of according to claim 1, wherein the first target is proximal to a second target if is less than about 100 nm, less than about 50 nm, less than about 20 nm apart, less than about 10 nm, less than about 5 nm, or less than about 2 nm apart.

18. The method according to claim 1, wherein labeling the first target or labeling the second target includes contacting the sample with a reagent comprising a linker.

19. The method according to claim 18, wherein the linker has from about 2 to about 20 PEG units.

20. The method according to claim 18, wherein the linker is selected from $PEG_2$, $PEG_3$, $PEG_4$, $PEG_5$, $PEG_6$, $PEG_7$, $PEG_8$, $PEG_9$, $PEG_{10}$, $PEG_{11}$, $PEG_{12}$, $PEG_{13}$, $PEG_{14}$, $PEG_{15}$, $PEG_{16}$, $PEG_{17}$, $PEG_{18}$, $PEG_{19}$, $PEG_{20}$, 1,4-diaminohexane, xylylenediamine, terephthalic acid, 3,6-dioxaoctanedioic acid, ethylenediamine-N,N-diacetic acid, 1,1'-ethylenebis(5-oxo-3-pyrrolidinecarboxylic acid), 4,4'-ethylenedipiperidine, succinimidyl-6-hydrazino-nicotinamide(S-HyNic, HyNic-NHS), N-succinimidyl-4-formylbenzoate (S-4FB, 4-FB-NHS), maleimide HyNic (MHPH), maleimide 4FB (MTFB), succinimidyl-[(N-maleimidopropionamido)-octaethyleneglycol] ester (Mal-$PEG_8$-NHS), succinimidyl-[(N-maleimidopropionamido)-tetraethyleneglycol] ester (Mal-$PEG_4$-NHS), 4-FB-$PEG_4$-PFP, azidobenzoyl hydrazide, N-[4-(p-azidosalicylamino)butyl]-3'-[2'-pyridyldithio]propionamid), bis-sulfosuccinimidyl suberate, dimethyladipimidate, disuccinimidyltartrate, N-maleimidobutyryloxysuccinimide ester, N-hydroxy sulfosuccinimidyl-4-azidobenzoate, N-succinimidyl[4-azidophenyl]-1,3'-dithiopropionate, N-succinimidyl[4-iodoacetyl]aminobenzoate, glutaraldehyde, and succinimidyl-4-[N-maleimidomethyl]cyclohexane-1-carboxylate, 3-(2-pyridyldithio)propionic acid N-hydroxysuccinimide ester (SPDP), and 4-(N-maleimidomethyl)-cyclohexane-1-carboxylic acid N-hydroxysuccinimide ester (SMCC).

21. An automated method, comprising using an automated staining apparatus to perform one or more steps associated with a method of testing a formalin fixed paraffin embedded tissue sample for the presence of a first target and a second target in close proximity, the method comprising:
   contacting the sample with a first set of reagents so that the first target is recognized by a first binding moiety specific for the first target and that results in the conjugation or deposition of a biotin ligase proximally to the first target;
   contacting the sample with a second set of reagents so that the second target is recognized by a second binding moiety specific for the second target and that results in the conjugation or deposition of a biotin ligase substrate proximally to the second target;
   contacting the sample with biotin and biotinylation reagents so that the biotin ligase biotinylates the biotin ligase substrate if the first target and the second target are in close proximity; and
   detecting the biotin;
   wherein the first and second binding moieties are selected from an antibody, an antibody fragment, an antibody derivative or an antibody mimetic.

* * * * *